(12) United States Patent
Kovarik

(10) Patent No.: US 12,279,989 B2
(45) Date of Patent: *Apr. 22, 2025

(54) METHOD AND SYSTEM FOR INCREASING BENEFICIAL BACTERIA AND DECREASING PATHOGENIC BACTERIA IN THE ORAL CAVITY

(71) Applicant: Seed Health Inc., Venice, CA (US)

(72) Inventor: Joseph E. Kovarik, Englewood, CO (US)

(73) Assignee: Seed Health, Inc., Venice, CA (US)

( * ) Notice: Subject to any disclaimer, the term of this patent is extended or adjusted under 35 U.S.C. 154(b) by 378 days.

This patent is subject to a terminal disclaimer.

(21) Appl. No.: 17/738,771

(22) Filed: May 6, 2022

(65) Prior Publication Data

US 2022/0257410 A1 Aug. 18, 2022

Related U.S. Application Data

(63) Continuation-in-part of application No. 16/904,056, filed on Jun. 17, 2020, now Pat. No. 11,523,934,
(Continued)

(51) Int. Cl.
*A61F 5/56* (2006.01)
(52) U.S. Cl.
CPC .................................. *A61F 5/566* (2013.01)
(58) Field of Classification Search
CPC ...................................................... A61F 5/566
See application file for complete search history.

(56) References Cited

U.S. PATENT DOCUMENTS

| 1,492,600 A | 5/1924 | Laskey |
| 3,178,341 A | 4/1965 | Hamill et al. |

(Continued)

FOREIGN PATENT DOCUMENTS

| DE | 4412190 | 10/1995 |
| EP | 410696 | 1/1991 |

(Continued)

OTHER PUBLICATIONS

Fila et al.: Blue light treatment of Pseudomonas aeruginosa: Strong bactericidal activity, synergism with antibiotics and inactivation of virulence factors, Virulence, 2017, vol. 8, No. 6, 938-958 https://doi.org/10.1080/21505594.2016.1250995. (Year: 2017).*

(Continued)

*Primary Examiner* — Hong Yu
(74) *Attorney, Agent, or Firm* — Sheridan Ross P.C.

(57) ABSTRACT

A method and system for increasing beneficial bacteria populations in a subject's oral cavity and decreasing pathogenic bacteria to address a variety of diseases and conditions, thereby enhancing a person's oral and overall health, including through the use of oral strips that adhere to surfaces in the oral cavity and that include at least one of xylitol, *Lachnospira, Veillonella, Faecalibacterium* and/or *Rothia* bacteria, including bacteria transformed via a CRISPR system. Certain embodiments employ light to modify oral cavity bacterial populations, including the use of bioluminescent oral strips that promote the growth of beneficial bacteria and decrease pathogenic bacteria populations.

15 Claims, 4 Drawing Sheets

Related U.S. Application Data which is a continuation-in-part of application No. 15/983,250, filed on May 18, 2018, now Pat. No. 10,687,975, which is a continuation-in-part of application No. 15/384,716, filed on Dec. 20, 2016, now Pat. No. 9,987,224, and a continuation-in-part of application No. 15/270,034, filed on Sep. 20, 2016, now Pat. No. 9,750,802, and a continuation-in-part of application No. 15/228,454, filed on Aug. 4, 2016, now Pat. No. 9,585,920, said application No. 15/270,034 is a continuation-in-part of application No. 14/954,074, filed on Nov. 30, 2015, now Pat. No. 9,457,077, and a continuation-in-part of application No. 14/752,192, filed on Jun. 26, 2015, now Pat. No. 9,549,842, and a continuation-in-part of application No. 14/611,458, filed on Feb. 2, 2015, now Pat. No. 10,398,209, said application No. 14/954,074 is a continuation-in-part of application No. 14/574,517, filed on Dec. 18, 2014, now Pat. No. 9,408,880, said application No. 14/611,458 is a continuation of application No. 14/502,097, filed on Sep. 30, 2014, now Pat. No. 9,010,340, which is a continuation of application No. 14/307,651, filed on Jun. 18, 2014, now Pat. No. 8,936,030, said application No. 14/752,192 is a continuation-in-part of application No. 14/225,503, filed on Mar. 26, 2014, now Pat. No. 9,445,936, said application No. 14/307,651 is a continuation-in-part of application No. 14/079,054, filed on Nov. 13, 2013, now Pat. No. 8,757,173, which is a continuation of application No. 13/425,913, filed on Mar. 21, 2012, now Pat. No. 8,584,685, said application No. 14/225,503 is a continuation of application No. 13/367,052, filed on Feb. 6, 2012, now Pat. No. 8,701,671.

(60) Provisional application No. 62/275,341, filed on Jan. 6, 2016, provisional application No. 62/274,550, filed on Jan. 4, 2016, provisional application No. 62/387,404, filed on Dec. 24, 2015, provisional application No. 62/387,405, filed on Dec. 24, 2015, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013, provisional application No. 61/556,023, filed on Nov. 4, 2011, provisional application No. 61/467,767, filed on Mar. 25, 2011, provisional application No. 61/439,652, filed on Feb. 4, 2011.

(56) References Cited

U.S. PATENT DOCUMENTS

| | | |
|---|---|---|
| 3,640,741 A | 2/1972 | Etes |
| 3,832,460 A | 8/1974 | Kosti |
| 3,996,934 A | 12/1976 | Zaffaroni |
| 4,136,145 A | 1/1979 | Fuchs et al. |
| 4,136,162 A | 1/1979 | Fuchs et al. |
| 4,163,777 A | 8/1979 | Mitra |
| 4,226,848 A | 10/1980 | Nagai et al. |
| 4,250,163 A | 2/1981 | Nagai et al. |
| 4,285,934 A | 8/1981 | Tinnell |
| 4,286,592 A | 9/1981 | Chandrasekaran |
| 4,292,299 A | 9/1981 | Suzuki et al. |
| 4,381,296 A | 4/1983 | Tinnell |
| 4,517,173 A | 5/1985 | Kizawa et al. |
| 4,518,721 A | 5/1985 | Dhabhar et al. |
| 4,568,639 A | 2/1986 | Lew |
| 4,572,832 A | 2/1986 | Kigasawa et al. |
| 4,668,232 A | 5/1987 | Cordes et al. |
| 4,687,841 A | 8/1987 | Spilburg et al. |
| 4,713,243 A | 12/1987 | Schiraldi et al. |
| 4,715,369 A | 12/1987 | Susuki et al. |
| 4,720,486 A | 1/1988 | Spilburg et al. |
| 4,740,365 A | 4/1988 | Yukimatsu et al. |
| 4,765,983 A | 8/1988 | Takayanagi et al. |
| 4,830,008 A | 5/1989 | Meer |
| 4,849,246 A | 7/1989 | Schmidt |
| 4,867,970 A | 9/1989 | Newsham et al. |
| 4,889,720 A | 12/1989 | Konishi |
| 4,894,232 A | 1/1990 | Reul et al. |
| 4,900,554 A | 2/1990 | Yanagibashi et al. |
| 4,906,463 A | 3/1990 | Cleary et al. |
| 4,915,948 A | 4/1990 | Gallopo et al. |
| 4,937,078 A | 6/1990 | Mezei et al. |
| 4,995,555 A | 2/1991 | Woodruff |
| 5,002,970 A | 3/1991 | Eby, III |
| 5,059,189 A | 10/1991 | Cilento et al. |
| 5,064,654 A | 11/1991 | Berner et al. |
| 5,081,157 A | 1/1992 | Pomerantz |
| 5,081,158 A | 1/1992 | Pomerantz |
| 5,116,621 A | 5/1992 | Oji et al. |
| 5,137,729 A | 8/1992 | Kuroya et al. |
| 5,158,789 A | 10/1992 | DuRoss |
| 5,166,233 A | 11/1992 | Kuroya et al. |
| 5,190,053 A | 3/1993 | Meer |
| 5,192,802 A | 3/1993 | Rencher |
| 5,196,202 A | 3/1993 | Konishi |
| 5,277,877 A | 1/1994 | Jeffrey et al. |
| 5,284,161 A | 2/1994 | Karell |
| 5,298,258 A | 3/1994 | Akemi et al. |
| 5,314,915 A | 5/1994 | Rencher |
| 5,332,576 A | 7/1994 | Mantelle |
| 5,462,749 A | 10/1995 | Rencher |
| 5,465,734 A | 11/1995 | Alvarez et al. |
| 5,466,465 A | 11/1995 | Royds et al. |
| 5,505,956 A | 4/1996 | Kim et al. |
| 5,518,733 A | 5/1996 | Lamothe et al. |
| 5,578,315 A | 11/1996 | Chien et al. |
| 5,585,098 A | 12/1996 | Coleman |
| 5,614,501 A | 3/1997 | Richards |
| 5,629,003 A | 5/1997 | Horstmann et al. |
| 5,643,603 A | 7/1997 | Bottenberg et al. |
| 5,700,478 A | 12/1997 | Biegajski et al. |
| 5,713,852 A | 2/1998 | Anthony et al. |
| 5,718,702 A | 2/1998 | Edwards |
| 5,719,196 A | 2/1998 | Uhari |
| 5,792,067 A | 8/1998 | Karell |
| 5,800,832 A | 9/1998 | Tapolsky et al. |
| 5,804,211 A | 9/1998 | Robertson et al. |
| 5,843,021 A | 12/1998 | Edwards et al. |
| 5,855,872 A | 1/1999 | Libin |
| 5,876,995 A | 3/1999 | Bryan |
| 5,895,804 A | 4/1999 | Lee et al. |
| 5,900,245 A | 5/1999 | Sawhney et al. |
| 5,948,430 A | 9/1999 | Zerbe et al. |
| 5,988,171 A | 11/1999 | Sohn et al. |
| 6,054,143 A | 4/2000 | Jones |
| 6,072,100 A | 6/2000 | Mooney et al. |
| 6,139,861 A | 10/2000 | Friedman |
| 6,161,541 A | 12/2000 | Woodson |
| 6,174,546 B1 | 1/2001 | Therriault et al. |
| 6,210,699 B1 | 4/2001 | Acharya |
| 6,250,307 B1 | 6/2001 | Conrad et al. |
| 6,284,235 B1 | 9/2001 | Foreman et al. |
| 6,287,610 B1 | 9/2001 | Bowling et al. |
| 6,352,711 B1 | 3/2002 | Campbell |
| 6,375,963 B1 | 4/2002 | Repka et al. |
| 6,390,096 B1 | 5/2002 | Conrad et al. |
| 6,431,174 B1 | 8/2002 | Knudson et al. |
| 6,432,986 B2 | 8/2002 | Levin |
| 6,439,238 B1 | 8/2002 | Brenzel et al. |
| 6,453,905 B1 | 9/2002 | Conrad et al. |
| 6,458,380 B1 | 10/2002 | Leaderman |
| 6,458,777 B1 | 10/2002 | Sonis et al. |
| 6,467,485 B1 | 10/2002 | Schmidt |

(56) References Cited

U.S. PATENT DOCUMENTS

| | | |
|---|---|---|
| 6,502,574 B2 | 1/2003 | Stevens et al. |
| 6,509,028 B2 | 1/2003 | Williams et al. |
| 6,523,542 B2 | 2/2003 | Knudson et al. |
| 6,552,024 B1 | 4/2003 | Chen et al. |
| 6,555,125 B2 | 4/2003 | Campbell |
| 6,569,474 B2 | 5/2003 | Clayton et al. |
| 6,578,580 B2 | 6/2003 | Conrad et al. |
| 6,585,997 B2 | 7/2003 | Moro et al. |
| 6,599,883 B1 | 7/2003 | Romeo |
| 6,620,846 B1 | 9/2003 | Jonn et al. |
| 6,713,463 B2 | 3/2004 | Sonis et al. |
| 6,722,577 B2 | 4/2004 | Dobyns, III |
| 6,726,920 B1 | 4/2004 | Theeuwes et al. |
| 6,734,157 B2 | 5/2004 | Radwanski et al. |
| 6,748,951 B1 | 6/2004 | Schmidt |
| 6,794,318 B2 | 9/2004 | Anderson et al. |
| 6,803,420 B2 | 10/2004 | Cleary et al. |
| 6,916,480 B2 | 7/2005 | Anderson et al. |
| 6,919,373 B1 | 7/2005 | Lam et al. |
| 6,923,981 B2 | 8/2005 | Leung et al. |
| 7,001,609 B1 | 2/2006 | Matson et al. |
| 7,067,116 B1 | 6/2006 | Bess et al. |
| 7,087,249 B2 | 8/2006 | Burrelll |
| 7,097,853 B1 | 8/2006 | Garbe et al. |
| 7,122,198 B1 | 10/2006 | Singh et al. |
| 7,138,135 B2 | 11/2006 | Chen et al. |
| 7,143,709 B2 | 12/2006 | Brennan et al. |
| 7,146,981 B2 | 12/2006 | Knudson et al. |
| 7,267,975 B2 | 9/2007 | Strobel et al. |
| 7,276,246 B2 | 10/2007 | Zhang |
| 7,287,646 B2 | 10/2007 | Gierskcky |
| 7,306,812 B2 | 12/2007 | Zhang |
| 7,332,230 B1 | 2/2008 | Krumme |
| 7,353,194 B1 | 4/2008 | Kerker et al. |
| 7,357,891 B2 | 4/2008 | Yang et al. |
| 7,425,292 B2 | 9/2008 | Yang et al. |
| 7,441,559 B2 | 10/2008 | Nelson et al. |
| 7,470,397 B2 | 12/2008 | Meathrel et al. |
| 7,500,484 B2 | 3/2009 | Nelson et al. |
| 7,540,432 B2 | 6/2009 | Majerowski et al. |
| 7,566,310 B2 | 7/2009 | Badr et al. |
| 7,575,739 B2 | 8/2009 | Tamarkin et al. |
| 7,579,019 B2 | 8/2009 | Tapolsky et al. |
| 7,579,078 B2 | 8/2009 | Hartmann et al. |
| 7,615,235 B2 | 11/2009 | Rademacher et al. |
| 7,632,525 B2 | 12/2009 | Dodds et al. |
| 7,645,803 B2 | 1/2010 | Tamarkin et al. |
| 7,648,712 B2 | 1/2010 | Bess et al. |
| 7,650,848 B2 | 1/2010 | Brennan |
| 7,666,502 B2 | 2/2010 | Magill et al. |
| 7,669,603 B2 | 3/2010 | Knudson et al. |
| 7,686,021 B2 | 3/2010 | Knudson et al. |
| 7,704,518 B2 | 4/2010 | Tamarkin et al. |
| 7,727,466 B2 | 6/2010 | Meathrel et al. |
| 7,799,337 B2 | 9/2010 | Levin |
| 7,820,145 B2 | 10/2010 | Tamarkin et al. |
| 7,820,420 B2 | 10/2010 | Whitlock |
| 7,824,588 B2 | 11/2010 | Yang et al. |
| 7,824,704 B2 | 11/2010 | Anderson et al. |
| 7,845,356 B2 | 12/2010 | Paraschac et al. |
| 7,862,808 B2 | 1/2011 | Isolauri et al. |
| 7,901,925 B2 | 3/2011 | Bojrab |
| 7,906,140 B2 | 3/2011 | Bromley et al. |
| 7,937,159 B2 | 5/2011 | Lima et al. |
| 7,984,714 B2 | 7/2011 | Hausmann et al. |
| 7,992,566 B2 | 8/2011 | Pflueger et al. |
| 7,997,266 B2 | 8/2011 | Frazier et al. |
| 8,030,457 B2 | 10/2011 | Jackson et al. |
| 8,034,601 B2 | 10/2011 | Boileau et al. |
| 8,034,606 B2 | 10/2011 | Park et al. |
| 8,104,478 B2 | 1/2012 | Pflueger et al. |
| 8,110,215 B2 | 2/2012 | Koenig et al. |
| 8,197,872 B2 | 6/2012 | Mills et al. |
| 8,349,313 B2 | 1/2013 | Smith et al. |
| 8,357,368 B2 | 1/2013 | Dudek et al. |
| 8,362,206 B2 | 1/2013 | Wallach et al. |
| 8,383,201 B2 | 2/2013 | Berry et al. |
| 8,420,074 B2 | 4/2013 | Rehberger et al. |
| 8,454,729 B2 | 6/2013 | Mittelmark et al. |
| 8,481,299 B2 | 7/2013 | Gueniche |
| 8,496,914 B2 | 7/2013 | Bonfiglio |
| 8,584,685 B2 | 11/2013 | Kovarik et al. |
| 8,585,588 B2 | 11/2013 | Kovarik et al. |
| 8,591,412 B2 | 11/2013 | Kovarik et al. |
| 8,657,879 B2 | 2/2014 | Shalon et al. |
| 8,685,389 B2 | 4/2014 | Baur |
| 8,701,671 B2 | 4/2014 | Kovarik |
| 8,716,327 B2 | 5/2014 | Zhao |
| 8,757,173 B2 | 6/2014 | Kovarik et al. |
| 8,758,764 B2 | 6/2014 | Masignani et al. |
| 8,815,538 B2 | 8/2014 | Lanzalaco et al. |
| 8,829,165 B2 | 9/2014 | Jackson et al. |
| 8,859,741 B2 | 10/2014 | Jackson et al. |
| 8,865,211 B2 | 10/2014 | Tzannis |
| 8,936,030 B2 | 1/2015 | Kovarik et al. |
| 8,945,839 B2 | 2/2015 | Zhang et al. |
| 8,951,775 B2 | 2/2015 | Castiel |
| 8,999,372 B2 | 4/2015 | Davidson |
| 9,010,340 B2 | 4/2015 | Kovarik et al. |
| 9,011,834 B1 | 4/2015 | McKenzie et al. |
| 9,016,221 B2 | 4/2015 | Brennan et al. |
| 9,017,718 B2 | 4/2015 | Tan |
| 9,028,841 B2 | 5/2015 | Henn et al. |
| 9,044,420 B2 | 6/2015 | Dubensky, Jr |
| 9,045,547 B2 | 6/2015 | Jackson et al. |
| 9,056,912 B2 | 6/2015 | Grandi et al. |
| 9,095,704 B2 | 8/2015 | McGuire et al. |
| 9,131,884 B2 | 9/2015 | Holmes |
| 9,149,429 B2 | 10/2015 | Kovacs et al. |
| 9,234,204 B2 | 1/2016 | Qvit-Raz et al. |
| 9,254,295 B2 | 2/2016 | Adams et al. |
| 9,288,981 B2 | 3/2016 | Gandhi et al. |
| 9,295,682 B2 | 3/2016 | Nunes et al. |
| 9,314,489 B2 | 4/2016 | Kelly et al. |
| 9,457,077 B2 | 10/2016 | Kovarik et al. |
| 9,549,842 B2 | 1/2017 | Kovarik |
| 9,585,920 B2 | 3/2017 | Kovarik et al. |
| 9,730,967 B2 | 8/2017 | Kovarik et al. |
| 9,750,802 B2 | 9/2017 | Kovarik et al. |
| 9,795,641 B2 | 10/2017 | Nardelli et al. |
| 9,987,224 B2 | 6/2018 | Kovarik |
| 10,085,938 B2 | 10/2018 | Kovarik et al. |
| 10,086,018 B2 | 10/2018 | Kovarik |
| 10,111,913 B2 | 10/2018 | Kovarik |
| 10,195,273 B2 | 2/2019 | Clube |
| 10,245,288 B2 | 4/2019 | Kovarik |
| 10,314,865 B2 | 6/2019 | Kovarik |
| 10,314,866 B2 | 6/2019 | Kovarik |
| 10,512,661 B2 | 12/2019 | Kovarik |
| 10,548,761 B2 | 2/2020 | Kovarik |
| 10,555,976 B2 | 2/2020 | Kovarik |
| 10,668,014 B2 | 6/2020 | Kovarik et al. |
| 10,683,323 B2 | 6/2020 | Prakash et al. |
| 10,687,975 B2 | 6/2020 | Kovarik et al. |
| 10,716,815 B2 | 7/2020 | Kovarik et al. |
| 10,730,827 B2 | 8/2020 | Wortmann et al. |
| 10,760,075 B2 | 9/2020 | Sommer et al. |
| 10,835,560 B2 | 11/2020 | Kovarik |
| 10,940,169 B2 | 3/2021 | Kovarik et al. |
| 11,026,982 B2 | 6/2021 | Kovarik |
| 11,083,760 B2 | 8/2021 | Han |
| 11,213,552 B2 | 1/2022 | Kovarik |
| 11,357,722 B2 | 6/2022 | Kovarik et al. |
| 11,529,379 B2 | 12/2022 | Kovarik |
| 11,833,177 B2 | 12/2023 | Simmons et al. |
| 11,839,632 B2 | 12/2023 | Tye et al. |
| 11,844,720 B2 | 12/2023 | Tye et al. |
| 11,951,140 B2 | 4/2024 | Kovarik |
| 11,969,445 B2 | 4/2024 | Kovarik |
| 11,980,643 B2 | 5/2024 | Simmons et al. |
| 11,998,479 B2 | 6/2024 | Simmons et al. |
| 11,998,574 B2 | 6/2024 | Simmons et al. |
| 12,005,085 B2 | 6/2024 | Simmons et al. |
| 2002/0009429 A1 | 1/2002 | Bostwick |

(56) References Cited

U.S. PATENT DOCUMENTS

| | | |
|---|---|---|
| 2002/0009520 A1 | 1/2002 | Clayton et al. |
| 2002/0022057 A1 | 2/2002 | Battey et al. |
| 2002/0037310 A1 | 3/2002 | Jonn et al. |
| 2002/0044988 A1 | 4/2002 | Fuchs et al. |
| 2003/0031737 A1 | 2/2003 | Rosenbloom |
| 2003/0062050 A1 | 4/2003 | Schmidt |
| 2003/0083287 A1 | 5/2003 | Burgess et al. |
| 2003/0104041 A1 | 6/2003 | Hsu et al. |
| 2003/0106243 A1 | 6/2003 | Tucker |
| 2003/0124178 A1 | 7/2003 | Haley |
| 2003/0140930 A1 | 7/2003 | Knudson et al. |
| 2003/0149387 A1 | 8/2003 | Barakat et al. |
| 2003/0149445 A1 | 8/2003 | Knudson et al. |
| 2003/0206995 A1 | 11/2003 | Bowling et al. |
| 2004/0053352 A1 | 3/2004 | Ouyang et al. |
| 2004/0057962 A1 | 3/2004 | Timmerman |
| 2004/0062757 A1 | 4/2004 | Finegold |
| 2004/0096569 A1 | 5/2004 | Barkalow et al. |
| 2004/0110111 A1 | 6/2004 | Wasylucha |
| 2004/0115223 A1 | 6/2004 | Follansbee |
| 2004/0120991 A1 | 6/2004 | Schobel |
| 2004/0136923 A1 | 7/2004 | Davidson et al. |
| 2004/0142463 A1 | 7/2004 | Walker et al. |
| 2004/0166501 A1 | 8/2004 | Azimzai et al. |
| 2004/0170617 A1 | 9/2004 | Finegold |
| 2004/0180080 A1 | 9/2004 | Furasawa et al. |
| 2004/0224007 A1 | 11/2004 | Zhang |
| 2004/0228804 A1 | 11/2004 | Jones et al. |
| 2005/0004417 A1 | 1/2005 | Nelson et al. |
| 2005/0159637 A9 | 1/2005 | Nelson et al. |
| 2005/0118655 A1 | 6/2005 | Weinstock et al. |
| 2005/0137109 A1 | 6/2005 | Quan et al. |
| 2005/0196358 A1 | 9/2005 | Georglades et al. |
| 2005/0197495 A1 | 9/2005 | Naidu |
| 2005/0260544 A1 | 11/2005 | Jones et al. |
| 2006/0018843 A1 | 1/2006 | Fine |
| 2006/0035008 A1 | 2/2006 | Virgalli et al. |
| 2006/0064903 A1 | 3/2006 | Tucker |
| 2006/0127330 A1 | 6/2006 | Tsuchida et al. |
| 2006/0188813 A1 | 8/2006 | Shimada |
| 2006/0204591 A1 | 9/2006 | Burrel et al. |
| 2006/0207721 A1 | 9/2006 | Slominski et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0093420 A1 | 4/2007 | Yeomans |
| 2007/0098744 A1 | 5/2007 | Knorr et al. |
| 2007/0102010 A1 | 5/2007 | Lemperle et al. |
| 2007/0122455 A1 | 5/2007 | Myers et al. |
| 2007/0123448 A1 | 5/2007 | Kaplan et al. |
| 2007/0148136 A1 | 6/2007 | Whitlock |
| 2007/0202057 A1 | 8/2007 | Fankhauser et al. |
| 2007/0207955 A1 | 9/2007 | Tanihara et al. |
| 2007/0218114 A1 | 9/2007 | Sorousch |
| 2007/0227545 A1 | 10/2007 | Conrad et al. |
| 2007/0231923 A1 | 10/2007 | Cumberland et al. |
| 2007/0246052 A1 | 10/2007 | Hegde et al. |
| 2007/0261701 A1 | 11/2007 | Sanders |
| 2007/0280964 A1 | 12/2007 | Knorr et al. |
| 2007/0293587 A1 | 12/2007 | Haley |
| 2007/0295340 A1 | 12/2007 | Buscemi |
| 2008/0032253 A1 | 2/2008 | Montgomery et al. |
| 2008/0075825 A1 | 3/2008 | Fuisz et al. |
| 2008/0112983 A1 | 5/2008 | Bufe et al. |
| 2008/0242543 A1 | 10/2008 | Banerjee et al. |
| 2008/0267933 A1 | 10/2008 | Ohlson et al. |
| 2008/0286210 A1 | 11/2008 | He |
| 2008/0305089 A1 | 12/2008 | Bufe et al. |
| 2009/0004275 A1 | 1/2009 | Martyn |
| 2009/0098192 A1 | 4/2009 | Fuisz |
| 2009/0130199 A1 | 5/2009 | Kovacs |
| 2009/0148482 A1 | 6/2009 | Peters |
| 2009/0196907 A1 | 8/2009 | Bunick |
| 2009/0196908 A1 | 8/2009 | Lee |
| 2009/0205083 A1 | 8/2009 | Gupta et al. |
| 2010/0029832 A1 | 2/2010 | Pinnavaia et al. |
| 2010/0040593 A1 | 2/2010 | Hedman et al. |
| 2010/0040712 A1 | 2/2010 | Fisher |
| 2010/0081681 A1 | 4/2010 | Blagosklonny |
| 2010/0092406 A1 | 4/2010 | Perez-Davidi et al. |
| 2010/0124560 A1* | 5/2010 | Hugerth .............. A61K 9/4825 514/343 |
| 2010/0143447 A1 | 6/2010 | Hansen et al. |
| 2010/0229876 A1 | 9/2010 | Knudson et al. |
| 2010/0247644 A1 | 9/2010 | Domb et al. |
| 2010/0260720 A1 | 10/2010 | Sprenger |
| 2010/0285098 A1 | 11/2010 | Haley |
| 2011/0009834 A1 | 1/2011 | Asmussen et al. |
| 2011/0033542 A1 | 2/2011 | Myers et al. |
| 2011/0088701 A1 | 4/2011 | Thornton |
| 2011/0100378 A1 | 5/2011 | Rousseau |
| 2011/0142942 A1 | 6/2011 | Gardner et al. |
| 2011/0217368 A1 | 9/2011 | Prakash et al. |
| 2011/0230587 A1 | 9/2011 | Macinnis et al. |
| 2011/0230727 A1 | 9/2011 | Sanders et al. |
| 2011/0250626 A1 | 10/2011 | Williams et al. |
| 2011/0274795 A1 | 11/2011 | Bogue et al. |
| 2011/0290694 A1 | 12/2011 | Fuisz et al. |
| 2012/0027786 A1 | 2/2012 | Gupta |
| 2012/0029832 A1 | 2/2012 | Dodgson |
| 2012/0039806 A1 | 2/2012 | Lahoud et al. |
| 2012/0058094 A1 | 3/2012 | Blasser et al. |
| 2012/0128597 A1 | 5/2012 | Peters et al. |
| 2012/0142548 A1 | 6/2012 | Corsi et al. |
| 2012/0148629 A1 | 6/2012 | Holvoet et al. |
| 2012/0222685 A1 | 9/2012 | Kovarik |
| 2012/0276143 A1 | 11/2012 | O'Mahony et al. |
| 2012/0276149 A1 | 11/2012 | Littman et al. |
| 2012/0276525 A1 | 11/2012 | Kovarik et al. |
| 2012/0283269 A1 | 11/2012 | Blagosklonny et al. |
| 2012/0294822 A1 | 11/2012 | Russo et al. |
| 2012/0301452 A1 | 11/2012 | Gueniche et al. |
| 2013/0059815 A1 | 3/2013 | Fournell et al. |
| 2013/0087155 A1 | 4/2013 | Hedman et al. |
| 2013/0157876 A1 | 6/2013 | Lynch et al. |
| 2013/0225440 A1 | 8/2013 | Friedman et al. |
| 2013/0236488 A1 | 9/2013 | Dashper et al. |
| 2013/0252983 A1 | 9/2013 | Cerione et al. |
| 2013/0259834 A1 | 10/2013 | Klaenhammer et al. |
| 2013/0310416 A1 | 11/2013 | Blagosklonny |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0030332 A1 | 1/2014 | Baron et al. |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0125550 A1 | 5/2014 | Kaneko et al. |
| 2014/0154290 A1 | 6/2014 | Peters et al. |
| 2014/0199266 A1 | 7/2014 | Park |
| 2014/0238411 A1 | 8/2014 | Kovarik |
| 2014/0255351 A1 | 9/2014 | Berstad et al. |
| 2014/0271867 A1 | 9/2014 | Myers |
| 2014/0294915 A1 | 10/2014 | Barreca et al. |
| 2014/0296139 A1 | 10/2014 | Cohen et al. |
| 2014/0333003 A1 | 11/2014 | Allen |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0364460 A1 | 12/2014 | Freed-Pastor et al. |
| 2014/0377278 A1 | 12/2014 | Elinav et al. |
| 2015/0004130 A1 | 1/2015 | Faber et al. |
| 2015/0017143 A1 | 1/2015 | Holvoet et al. |
| 2015/0017227 A1 | 1/2015 | Kim |
| 2015/0038594 A1 | 2/2015 | Borges et al. |

(56) References Cited

U.S. PATENT DOCUMENTS

| | | |
|---|---|---|
| 2015/0045546 A1 | 2/2015 | Siksnys et al. |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0147371 A1 | 5/2015 | Kovarik et al. |
| 2015/0150792 A1 | 6/2015 | Klingman |
| 2015/0166641 A1 | 6/2015 | Goodman |
| 2015/0174178 A1 | 6/2015 | Kovarik et al. |
| 2015/0190435 A1 | 7/2015 | Henn et al. |
| 2015/0202136 A1 | 7/2015 | Lanzalaco et al. |
| 2015/0216917 A1 | 8/2015 | Jones |
| 2015/0224072 A1 | 8/2015 | Pellikaan |
| 2015/0252358 A1 | 9/2015 | Maeder |
| 2015/0259728 A1 | 9/2015 | Cutliffe et al. |
| 2015/0329555 A1 | 11/2015 | Liras |
| 2015/0329875 A1 | 11/2015 | Gregory |
| 2015/0352023 A1 | 12/2015 | Berg |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0000754 A1 | 1/2016 | Stamets |
| 2016/0000841 A1 | 1/2016 | Yamamoto et al. |
| 2016/0008412 A1 | 1/2016 | Putaala et al. |
| 2016/0024510 A1 | 1/2016 | Bikard et al. |
| 2016/0040216 A1 | 2/2016 | Wilder |
| 2016/0069921 A1 | 3/2016 | Holmes et al. |
| 2016/0089315 A1 | 3/2016 | Kleinberg et al. |
| 2016/0089405 A1 | 3/2016 | Lue |
| 2016/0095316 A1 | 4/2016 | Goodman et al. |
| 2016/0120915 A1 | 5/2016 | Blaser et al. |
| 2016/0122806 A1 | 5/2016 | Amini et al. |
| 2016/0151427 A1 | 6/2016 | Whitlock et al. |
| 2016/0151428 A1 | 6/2016 | Bryan |
| 2016/0158294 A1 | 6/2016 | Von Maltzahn et al. |
| 2016/0168594 A1 | 6/2016 | Zhang et al. |
| 2016/0175327 A1 | 6/2016 | Adams et al. |
| 2016/0199424 A1 | 7/2016 | Berry et al. |
| 2016/0206564 A1 | 7/2016 | Trachtman |
| 2016/0206666 A1 | 7/2016 | Falb et al. |
| 2016/0206668 A1 | 7/2016 | Kort et al. |
| 2016/0213702 A1 | 7/2016 | Von Maltzahn et al. |
| 2016/0243132 A1 | 8/2016 | Adams et al. |
| 2016/0271106 A1 | 9/2016 | Shi et al. |
| 2016/0271189 A1 | 9/2016 | Cutcliffe |
| 2016/0311913 A1 | 10/2016 | Sun |
| 2016/0314281 A1 | 10/2016 | Apte |
| 2016/0354416 A1 | 12/2016 | Gajewski et al. |
| 2016/0374941 A1 | 12/2016 | Barreca et al. |
| 2017/0014341 A1 | 1/2017 | Armer et al. |
| 2017/0020932 A1 | 1/2017 | Cutcliffe et al. |
| 2017/0027914 A1 | 2/2017 | Qi |
| 2017/0042860 A1 | 2/2017 | Kashyap et al. |
| 2017/0042924 A1 | 2/2017 | Otsuka et al. |
| 2017/0071986 A1 | 3/2017 | Kovarik et al. |
| 2017/0079947 A1 | 3/2017 | Richards |
| 2017/0100328 A1 | 4/2017 | Kovarik et al. |
| 2017/0232043 A1 | 8/2017 | Falb et al. |
| 2017/0240625 A1 | 8/2017 | Zeller et al. |
| 2017/0246269 A1 | 8/2017 | Hajishengallis et al. |
| 2017/0298115 A1 | 10/2017 | Loomis et al. |
| 2017/0312232 A1 | 11/2017 | Vitetta et al. |
| 2017/0342141 A1 | 11/2017 | Russo et al. |
| 2017/0348303 A1 | 12/2017 | Bosse et al. |
| 2018/0000878 A1 | 1/2018 | Goodman et al. |
| 2018/0015131 A1 | 1/2018 | Gajewski et al. |
| 2018/0016647 A1 | 1/2018 | Van Sinderen et al. |
| 2018/0092899 A1 | 4/2018 | Liu et al. |
| 2018/0100169 A1 | 4/2018 | Soucaille et al. |
| 2018/0110795 A1 | 4/2018 | Frias-Lopez |
| 2018/0111984 A1 | 5/2018 | Bigal et al. |
| 2018/0127490 A1 | 5/2018 | Bigal et al. |
| 2018/0134772 A1 | 5/2018 | Sharma et al. |
| 2018/0140698 A1 | 5/2018 | Clube et al. |
| 2018/0207165 A1 | 7/2018 | Harmsen et al. |
| 2018/0235987 A1 | 8/2018 | Von Maltzahn et al. |
| 2018/0258100 A1 | 9/2018 | Gregory et al. |
| 2018/0296582 A1 | 10/2018 | Von Maltzahn et al. |
| 2018/0303658 A1 | 10/2018 | Kovarik et al. |
| 2018/0312851 A1 | 11/2018 | Falb et al. |
| 2018/0326008 A1 | 11/2018 | Schreiber et al. |
| 2018/0371405 A1 | 12/2018 | Barrangou et al. |
| 2019/0000815 A1 | 1/2019 | Melin |
| 2019/0018012 A1 | 1/2019 | Kovarik |
| 2019/0059314 A1 | 2/2019 | Aharoni et al. |
| 2019/0290605 A1 | 6/2019 | Rasochova et al. |
| 2019/0120960 A1 | 7/2019 | Konradi et al. |
| 2019/0262298 A1 | 8/2019 | Kanthasamy et al. |
| 2019/0315642 A1 | 10/2019 | Parsley et al. |
| 2019/0388471 A1 | 12/2019 | June et al. |
| 2019/0390284 A1 | 12/2019 | Kim |
| 2020/0009185 A1 | 1/2020 | Shin et al. |
| 2020/0009268 A1 | 1/2020 | Scholz |
| 2020/0032224 A1 | 1/2020 | Schaefer et al. |
| 2020/0121743 A1 | 4/2020 | Kovarik |
| 2020/0148642 A1 | 5/2020 | Konradi et al. |
| 2020/0155447 A1 | 5/2020 | Edwards |
| 2020/0163796 A1 | 5/2020 | Kovarik |
| 2020/0188454 A1 | 6/2020 | Slykerman |
| 2020/0190494 A1 | 6/2020 | Hou et al. |
| 2020/0197215 A1 | 6/2020 | Kovarik et al. |
| 2020/0199555 A1 | 6/2020 | Zhang |
| 2020/0323679 A1 | 10/2020 | Kovarik |
| 2020/0397832 A1 | 12/2020 | Kovarik |
| 2021/0000883 A1 | 1/2021 | Kovarik |
| 2021/0169954 A1 | 6/2021 | Balani et al. |
| 2021/0198665 A1 | 7/2021 | Sommer et al. |
| 2021/0308028 A1 | 10/2021 | Yang et al. |
| 2021/0321756 A1 | 10/2021 | McLaughlin et al. |
| 2021/0361560 A1 | 11/2021 | Krueger et al. |
| 2021/0386659 A1 | 12/2021 | Kim |
| 2022/0000760 A1 | 1/2022 | Rasochova |
| 2022/0023259 A1 | 1/2022 | Davidson et al. |
| 2022/0031590 A1 | 2/2022 | Pesaro et al. |
| 2022/0031767 A1 | 2/2022 | Duportet et al. |
| 2022/0071877 A1 | 3/2022 | Zenobia et al. |
| 2022/0088001 A1 | 3/2022 | Kovarik et al. |
| 2022/0088090 A1 | 3/2022 | Lobacki et al. |
| 2022/0118031 A1 | 4/2022 | Kovarik |
| 2022/0135987 A1 | 5/2022 | Leveau et al. |
| 2022/0193150 A1 | 6/2022 | Kovarik |
| 2022/0193157 A1 | 6/2022 | Zimmerman et al. |
| 2022/0296500 A1 | 9/2022 | Kovarik |
| 2022/0331374 A1 | 10/2022 | Richter et al. |
| 2022/0331375 A1 | 10/2022 | Kovarik |
| 2022/0339208 A1 | 10/2022 | Abel et al. |
| 2022/0378853 A1 | 12/2022 | Kovarik |
| 2022/0387402 A1 | 12/2022 | Aspnes et al. |
| 2023/0106721 A1 | 4/2023 | Catania et al. |
| 2024/0156878 A1 | 5/2024 | Jensen et al. |

FOREIGN PATENT DOCUMENTS

| | | |
|---|---|---|
| JP | S56-100714 | 8/1981 |
| WO | WO 98/22097 | 5/1998 |
| WO | WO 2006/007922 | 1/2006 |
| WO | WO 2006/015445 | 2/2006 |
| WO | WO 2006/133879 | 12/2006 |
| WO | WO 2008/088426 | 7/2008 |
| WO | WO 2008/097890 | 8/2008 |
| WO | PCT/US2008/080362 | 10/2008 |
| WO | WO 2009/052421 | 4/2009 |
| WO | WO 2010/041143 | 4/2010 |
| WO | WO 2011/020780 | 2/2011 |
| WO | WO/2013026000 | 2/2013 |
| WO | WO 2011/029701 | 5/2013 |
| WO | WO 2013/107750 | 7/2013 |
| WO | WO 2013/182038 | 12/2013 |
| WO | PCT/US2014/036849 | 5/2014 |
| WO | WO 2014/103488 | 7/2014 |
| WO | WO 2014/152338 | 9/2014 |
| WO | WO 2014/196913 | 12/2014 |
| WO | WO 2015/069682 | 5/2015 |

(56) References Cited

FOREIGN PATENT DOCUMENTS

| WO | WO 2016/066763 | 5/2016 |
|---|---|---|
| WO | WO 2016/070151 | 5/2016 |
| WO | WO 2017/211753 | 12/2017 |
| WO | WO 2019/018348 | 1/2019 |
| WO | WO 2019/067621 | 4/2019 |
| WO | WO 2022/185121 | 9/2022 |
| WO | WO 2022/187274 | 9/2022 |

OTHER PUBLICATIONS

Official Action for U.S. Appl. No. 18/103,768, dated Apr. 25, 2023, 5 pages.
Baud et al., "Microbial diversity in the vaginal microbiota and its link to pregnancy outcomes," Scientific Reports, vol. 13, No. 9061, 2023, 12 pages.
Brown et al., "Improving the Diagnosis of Vulvovaginitis: Perspectives to Align Practice, Guidelines, and Awareness," Population Health Management, vol. 23, Suppl. 1, 2020, pp. S3-S12.
De Seta et al., "The Vaginal Community State Types Microbiome—Immune Network as Key Factor for Bacterial Vaginosis and Aerobic Vaginitis," Frontiers in Microbiology, vol. 10, No. 2451, Oct. 30, 2019, 8 pages.
Gajer et al., "Temporal Dynamics of the Human Vaginal Microbiota," Science Translational Medicine, vol. 4, No. 132, May 2, 2012, 21 pages.
Hildebrand et al., "Vaginitis," NCBI Bookshelf, Updated Nov. 14, 2022, 12 pages.
Lenger et al., "D-mannose vs other agents for recurrent urinary tract infection prevention in adult women: a systematic review and meta-analysis," American Journal of Obstetrics and Gynecology, vol. 223, No. 2, Aug. 2020, pp. 265.e1-265.e13.
Lewis et al., "Vaginal Microbiome and Its Relationship to Behavior, Sexual Health, and Sexually Transmitted Diseases," Obstetrics & Gynecology, vol. 129, No. 4, Apr. 2017, pp. 643-654.
Ma et al., "The vaginal microbiome: rethinking health and diseases," Annual Review of Microbiology, vol. 66, 2012, pp. 371-389.
O'Hanlon et al., "In vaginal fluid, bacteria associated with bacterial vaginosis can be suppressed with lactic acid but not hydrogen peroxide," BMC Infectious Diseases, vol. 11, No. 200, 2011, 8 pages.
Paladine et al., "Vaginitis: Diagnosis and Treatment," American Family Physician, vol. 97, No. 5, Mar. 1, 2018, pp. 321-329.
Ravel et al., "Vaginal microbiome of reproductive-age women," PNAS, vol. 108, Suppl. 1, Mar. 15, 2011, pp. 4680-4687.
Scaglione et al., "Considerations on D-mannose Mechanism of Action and Consequent Classification of Marketed Healthcare Products," Frontiers In Pharmacology, vol. 12, No. 636377, Mar. 2, 2021, 7 pages.
Schaeffer et al., "Effect of Carbohydrates on Adherence of *Escherichia coli* to Human Urinary Tract Epithelial Cells," Infection and Immunity, vol. 30, No. 2, Nov. 1980, pp. 531-537.
Simmering et al., "The Increase in Hospitalizations for Urinary Tract Infections and the Associated Costs in the United States, 1998-2011," Open Forum Infectious Diseases, vol. 4, No. 1, Feb. 24, 2017, 7 pages.
Notice of Allowance for U.S. Appl. No. 17/893,384, dated Aug. 23, 2023, 7 pages.
Notice of Allowance for U.S. Appl. No. 18/087,545, dated Jul. 26, 2023, 7 pages.
Official Action for U.S. Appl. No. 18/178,847, dated Jul. 13, 2023, 8 pages.
Notice of Allowance for U.S. Appl. No. 18/178,847, dated Aug. 8, 2023, 8 pages.
Official Action for U.S. Appl. No. 18/130,946, dated Jun. 30, 2023, 6 pages.
Notice of Allowance for U.S. Appl. No. 18/130,946, dated Aug. 1, 2023, 8 pages.
Notice of Allowance for U.S. Appl. No. 18/103,768, dated Aug. 1, 2023, 7 pages.

Official Action for U.S. Appl. No. 18/143,399, dated Sep. 7, 2023, 8 pages.
Hemert et al.: Migraine Associated with Gastrointestinal Disorders: Review of the Literature and Clinical Implications, Frontiers in Neurology, 2014, 5, 241.
Mach et al.: Endurance exercise and gut microbiota: A review, Journal of Sport and Health Science, vol. 6, Issue 2, Jun. 2017, pp. 179-197.
Sivieri et al. (Lactobacillus acidophilus CRL 1014 improved "gut health" in the Shime reactor, BMC Gastroenterology, 201313:10.
Fiber-Famished Gut Microbes Linked to Poor Health: retrieved from internet: https://www.scientificamerican.com/article/fiber-farnished-out-microbes-linked-to-poor-health1/. Retrieved on Oct. 26, 2017.
Klingspor et al.: Enterococcus faecium NCIMB Modulates Epithelial Integrity, Heat Shock Protein, and Proinflammatory Cytokine Response in Intestinal Cells, Mediators of Inflammation, vol. 2015 (2015), Article ID 304149, 11 pages.
Spinler et al.: Human-derived probiotic Lactobacillus reuteri demonstrate antimicrobial activities targeting diverse enteric bacterial pathogens, Anaerobe, vol. 14, Issue 3, Jun. 2008, pp. 166-171.
Basseri et al.: Antibiotics for the Treatment of Irritable Bowel Syndrome, Gastroenterology Hepatology (NY). Jul. 2011; 7(7): 455-493.
McFadzean: Exercise can help modulate human gut microbiota, retrieved from internet: https://scholar.colorado.edu/ogi/viewcontent.callatricle=1154&context=honr_theses. Retrieved on May 20, 2019.
Chen et al.: Targeting Aldehyde Dehydrogenase 2: New Therapeutic Opportunities, retrieved frominternet: https://www.ncbi.nlm.nih.gov/prnce/articles/PMC3929114/?report=printable. retrieved on Feb. 28, 2019.
The structure behind the simplicity of CRISPR/Cas9: retrieved from internet: https://thecinder.com/2015/12/23-the-structure-behind-the-simplicity-of-crisprcas9/. Retrieved Feb. 28, 2019.
Notice of Allowance for U.S. Appl. No. 17/854,422, dated Feb. 17, 2023, 7 pages.
U.S. Appl. No. 17/854,389, filed Jun. 30, 2022, Kovarik.
U.S. Appl. No. 17/893,384, filed Aug. 23, 2022, Kovarik.
U.S. Appl. No. 18/087,545, filed Dec. 22, 2022, Kovarik.
"Oral Cavity," University of Michigan Medical School, Date Unknown, retrieved Nov. 20, 2019 from https://histology.medicine.umich.edu/resources/oral-cavity, 5 pages.
Abruzzo et al., "Influence of Lactobacillus Biosurfactants on Skin Permeation of Hydrocortisone," Pharmaceutics, vol. 13, No. 6, May 2021, 14 pages.
Agrawal et al., "Technique to Control pH in Vicinity of Biodegrading PLA-PGA Implants," Journal of Biomedical Materials Research, vol. 38, No. 2, 1997, pp. 105-114.
Aguilar-Toala et al., "Potential role of natural bioactive peptides for development of cosmeceutical skin products," Peptides, vol. 122, No. 170170, Dec. 2019, 8 pages. Abstract only.
Athanasiou et al., "In Vitro Degradation and Release Characteristics of Biodegradable Implants Containing Trypsin Inhibitor," Clinical Orthopaedics and Related Research, vol. 315, Jun. 1995, pp. 272-281. Abstract only.
Blumen et al., "Radiofrequency Ablation for the Treatment of Mild to Moderate Obstructive Sleep Apnea," The Laryngoscope, vol. 112, No. 11, Nov. 2002, pp. 2086-2092.
Bocheva et al., "Protective Role of Melatonin and Its Metabolites in Skin Aging," International Journal of Molecular Sciences, vol. 23, No. 1238, Jan. 2022, 23 pages.
Brietzke et al., "Injection Snoreplasty: Extended Follow-Up and New Objective Data," Otolaryngology—Head and Neck Surgery, vol. 128, No. 5, May 2003, pp. 605-615. Abstract only.
Brietzke et al., "Injection Snoreplasty: How to Treat Snoring without All the Pain and Expense," Otolaryngology—Head and Neck Surgery, vol. 124, No. 5, May 2001, pp. 503-510. Abstract only.
Brietzke et al., "Injection Snoreplasty: Investigation of Alternative Sclerotherapy Agents," Otolaryngology—Head and Neck Surgery, vol. 130, No. 1, Jan. 2004, pp. 47-57. Abstract only.

(56) References Cited

OTHER PUBLICATIONS

Catalano et al., "Additional palatal implants for refractory snoring," Otolaryngology—Head and Neck Surgery, vol. 137, No. 1, Jul. 2007, pp. 105-109. Abstract only.

Charulatha et al., "Influence of different crosslinking treatments on the physical properties of collagen membranes," Biomaterials, vol. 24, No. 5, 2003, pp. 759-767.

Choi et al., "Therapeutic Effects of Cold-Pressed Perilla Oil Mainly Consisting of Linolenic acid, Oleic Acid and Linoleic Acid on UV-Induced Photoaging in NHDF Cells and SKH-1 Hairless Mice," Molecules, vol. 25, Feb. 2020, 19 pages.

Chuang et al., "Effects of exogenous crosslinking on in vitro tensile and compressive moduli of lumbar intervertebral discs," Clinical Biomechanics, vol. 22, No. 1, Jan. 2007, pp. 14-20. Abstract only.

Ding et al., "Resveratrol accelerates wound healing by inducing M2 macrophage polarisation in diabetic mice," Pharmaceutical Biology, vol. 60, No. 1, 2022, pp. 2328-2337.

Douam et al., "Genetic Dissection of the Host Tropism of Human-Tropic Pathogens," Annual Review of Genetics, vol. 49, 2015, pp. 21-45.

Dunkley et al., "A role for CD4+ T cells from orally immunized rats in enhanced clearance of Pseudomonas aeruginosa from the lung," Immunology, vol. 83, 1994, pp. 362-369.

Earlia et al., "GC/MS Analysis of Fatty Acids on Pliek U Oil and Its Pharmacological Study by Molecular Docking to Filaggrin as a Drug Candidate in Atopic Dermatitis Treatment," Scientific World Journal, Nov. 2019, 7 pages.

Enomoto et al., "Koji amazake Maintains Water Content in the Left Cheek Skin of Healthy Adults: A Randomized, Double-Blind, Placebo-Controlled, Parallel-Group, Comparative Trial," Clinical, Cosmetic and Investigational Dermatology, vol. 15, Jul. 2022, pp. 1283-1291.

Farhadihosseinabadi et al., "The in vivo effect of Lacto-N-neotetraose (LNnT) on the expression of type 2 immune response involved genes in the wound healing process, " Scientific Reports, vol. 10, No. 997, Jan. 2020, 11 pages.

Fischer et al., "[Radiofrequency ablation of the soft palate (somnoplasty). A new method in the treatment of habitual and obstructive snoring]," HNO, vol. 48, No. 1, Jan. 2000, pp. 33-40. Abstract only.

Friedman et al., "Patient Selection and Efficacy of Pillar Implant Technique for Treatment of Snoring and Obstructive Sleep Apnea/Hypopnea Syndrome," Otolaryngology—Head and Neck Surgery, vol. 134, No. 2, Feb. 2006, pp. 187-196. Abstract only.

Gratzer et al., "Control of pH Alters the Type of Cross-linking Produced by 1-Ethyl-3-(3-Dimethylaminopropyl)-Carbodiimide (EDC) Treatment of Acellular Matrix Vascular Grafts," Journal of Biomedical Materials Research, vol. 58, No. 2, 2001, pp. 172-179.

Guilleminault et al., "Snoring (I). Daytime sleepiness in regular heavy snorers," Chest, vol. 99, 1991, pp. 40-48.

Guilleminault et al., "The sleep apnea syndromes," Annual Review of Medicine, vol. 27, Feb. 1976, pp. 465-484. First Page Only.

Han et al., "Proanthocyanidin: A natural crosslinking reagent for stabilizing collagen matrices," Journal of Biomedical Materials Research, vol. 65A, No. 1, Apr. 2003, pp. 118-124. Abstract only.

Hedman et al., "Exogenous Cross-Linking Increases the Stability of Spinal Motion Segments," Spine, vol. 31, No. 15, Jul. 2006, pp. E480-E485. Abstract only.

Hoffmann et al., "Glutaraldehyde and oxidised dextran as crosslinker reagents for chitosan-based scaffolds for cartilage tissue engineering," Journal of Materials Science: Materials in Medicine, vol. 20, Mar. 2009, pp. 1495-1503.

Hunter et al., "Meniscal material properties are minimally affected by matrix stabilization using glutaraldehyde and glycation with ribose," Journal of Orthopaedic Research, vol. 23, 2005, pp. 555-561.

Kim et al., "Kaempferol tetrasaccharides restore skin atrophy via PDK1 inhibition in human skin cells and tissues: Bench and clinical studies," Biomedicine & Pharmacotherapy, vol. 156, No. 113864, Dec. 2022, 13 pages.

Kim et al., "Spermidine-induced recovery of human dermal structure and barrier function by skin microbiome," Communications Biology, vol. 4, No. 231, 2021, 11 pages.

Kim et al., "β-Glucogallin isolated from Fusidium coccineum and its enhancement of skin barrier effects," Applied Biological Chemistry, vol. 63, No. 77, Nov. 2020, 7 pages.

Klapperich et al., "A novel biocompatible adhesive incorporating plant-derived monomers," Journal of Biomedical Materials Research Part A, vol. 91, No. 2, pp. 378-374.

Ko, "Effects of Glycogen on Ceramide Production in Cultured Human Keratinocytes via Acid Sphingomyelinase Activation," Master's Thesis Submitted to the Graduate School of Public Health (Korea), 2018, 53 pages.

Komuro et al., "Sphingomyelin maintains the cutaneous barrier via regulation of the STAT3 pathway," The FASEB Journal, vol. 36, No. 4, Apr. 2022, 17 pages.

Kurek-Gorecka et al., "Bee Products in Dermatology and Skin Care," Molecules, vol. 25, No. 3, Jan. 2020, 17 pages.

Kyriakopoulos et al., "Taurine and N-Bromotaurine in Topical Treatment of Psoriasis," Advances in Experimental Medicine and Biology, vol. 1370, 2022, pp. 99-111. Abstract only.

Laneri et al., "Plant cell culture extract of Cirsium eriophorum with skin pore refiner activity by modulating sebum production and inflammatory response," Phytotherapy Research, vol. 35, No. 1, Jan. 2021, pp. 530-540.

Lebeer et al., "Selective targeting of skin pathobionts and inflammation with topically applied lactobacilli," Cell Reports Medicine, vol. 3, No. 2, Feb. 2022, 22 pages.

Lew et al., "Bioactives from probiotics for dermal health: functions and benefits," Journal of Applied Microbiology, vol. 114, No. 5, May 2013, pp. 1241-1253.

Liu et al., "Activation of aryl hydrocarbon receptor in Langerhans cells by a microbial metabolite of tryptophan negatively regulates skin inflammation," Journal of Dermatological Science, vol. 100, No. 3, Dec. 2020, pp. 192-200. Abstract only.

Liu et al., "The potential of *Streptococcus thermophiles* (TCI633) in the anti-aging," Journal of Cosmetic Dermatology, vol. 21, No. 6, Jun. 2022, pp. 2635-2647.

Mahdiani et al., "Protective effect of luteolin against chemical and natural toxicants by targeting NF-KB pathway," Biofactors, vol. 48, No. 4, Jul. 2022, pp. 744-762. Abstract only.

Matsui et al., "Biological Rhythms in the Skin," International Journal of Molecular Sciences, vol. 17, No. 801, May 2016, 15 pages.

Mayrovitz et al., "Assessing Potential Circadian, Diurnal, and Ultradian Variations in Skin Biophysical Properties," Cureus, vol. 13, No. 9, Sep. 2021, 18 pages.

Nakai et al., "Effects of Topical N-Acetylcysteine on Skin Hydration/Transepidermal Water Loss in Healthy Volunteers and Atopic Dermatitis Patients," Annals of Dermatology, vol. 27, No. 4, Aug. 2015, pp. 450-451.

Neves et al., "Efficacy of a topical serum containing L-ascorbic acid, neohesperidin, pycnogenol, tocopherol, and hyaluronic acid in relation to skin aging signs," Journal of Cosmetic Dermatology, vol. 21, No. 10, Oct. 2022, pp. 4462-4469. Abstract only.

Nisbet et al., "Clinical and in vitro evaluation of new anti-redness cosmetic products in subjects with winter xerosis and sensitive skin," International Journal of Cosmetic Science, vol. 41, No. 6, Dec. 2019, pp. 534-547.

Park et al., "Fermented black rice and blueberry with Lactobacillus plantarum MG4221 improve UVB-induced skin injury," Food and Agricultural Immunology, vol. 32, No. 1, 2021, pp. 499-515.

Pinto et al., "Plantaricin A synthesized by Lactobacillus plantarum induces in vitro proliferation and migration of human keratinocytes and increases the expression of TGF-β1, FGF7, VEGF-A and IL-8 genes," Peptides, vol. 32, No. 9, Sep. 2011, pp. 1815-1824. Abstract only.

Ragusa et al., "Spirulina for Skin Care: A Bright Blue Future," Cosmetics, vol. 8, No. 1, Jan. 2021, 19 pages.

Sevilla et al., "Revisiting the role of melatonin in human melanocyte physiology: A skin context perspective," Journal of Pineal Research, vol. 72, No. 3, Apr. 2022, 23 pages.

(56) References Cited

OTHER PUBLICATIONS

Sheikh, "Is Crispr the Next Antibiotic?," The New York Times, Oct. 29, 2019, retrieved from https://www.nytimes.com/2019/28/health/crispr-genetics-antibiotic-resistance.html, 2 pages.
Shen et al., "Propionibacterium acnes related anti-inflammation and skin hydration activities of madecassoside, a pentacyclic triterpene saponin from Centella asiatica," Bioscience, Biotechnology, and Biochemistry, vol. 83, No. 3, 2019, pp. 561-568.
Sheweita et al., "Preclinical studies on melanogenesis proteins using a resveratrol—nanoformula as a skin whitener," International Journal of Biological Macromolecules, vol. 223, Part A, Dec. 2022, pp. 870-881. Abstract only.
Sivieri et al., "Lactobacillus acidophilus CRL 1014 improved "gut health" in the SHIME reactor," BMC Gastroenterology, vol. 13, No. 100, 2013, 9 pages.
Thongaram et al., "Human milk oligosaccharide consumption by probiotic and human-associated bifidobacteria and lactobacilli," Journal of Dairy Science, vol. 100, No. 10, Oct. 2017, pp. 7825-7833.
Traisaeng et al., "A Derivative of Butyric Acid, the Fermentation Metabolite of *Staphylococcus epidermidis*, Inhibits the Growth of a *Staphylococcus aureus* Strain Isolated from Atopic Dermatitis Patients," Toxins, vol. 11, No. 6, May 2019, 12 pages.
Van Der Veer et al., "Comparative genomics of human Lactobacillus crispatus isolates reveals genes for glycosylation and glycogen degradation: implications for in vivo dominance of the vaginal microbiota," Microbiome, vol. 7, No. 49, 2019, 14 pages.
Wan et al., "Luteolin-7-glucoside Promotes Human Epidermal Stem Cell Proliferation by Upregulating β-Catenin, c-Myc, and Cyclin Expression," Stem Cells International, vol. 2019, No. 1575480, Jun. 2019, 10 pages.
Wilbie et al., "Delivery Aspects of CRISPR/Cas for in Vivo Genome Editing," Accounts of Chemical Research, vol. 52, 2019, pp. 1555-1564.
Yamamura et al., "Oral mucosal adhesive Film containing local anesthetics: in vitro and clinical evaluation." Journal of Biomedical Materials Research, Fall 1998, vol. 43, No. 3, pp. 313-317. Abstract only.
Yatsuhashi et al., "Effects of Glycogen on Ceramide Production in Cultured Human Keratinocytes via Acid Sphingomyelinase Activation," Journal of Applied Glycoscience, vol. 68, 2021, pp. 41-46.
Yosipovitch et al., "Time-Dependent Variations of the Skin Barrier Function in Humans: Transepidermal Water Loss, Stratum Corneum Hydration, Skin Surface pH, and Skin Temperature," Journal of INvestigative Dermatology, vol. 110, No. 1, Jan. 1998, pp. 20-23.
Zahedi et al., "Development of plasma functionalized polypropylene wound dressing for betaine hydrochloride controlled drug delivery on diabetic wounds," Scientific Reports, vol. 11, No. 9641, 2021, 18 pages.
Zhou et al., "Nicotinamide Mononucleotide Combined With Lactobacillus fermentum TKSN041 Reduces the Photoaging Damage in Murine Skin by Activating AMPK Signaling Pathway," Frontiers in Pharmacology, vol. 12, No. 643089, Mar. 2021, 17 pages.
Official Action for U.S. Appl. No. 13/367,052, dated Jan. 16, 2014, 8 pages.
Notice of Allowance for U.S. Appl. No. 13/367,052, dated Feb. 24, 2014, 5 pages.
Official Action for U.S. Appl. No. 14/225,503, dated May 4, 2016, 6 pages.
Notice of Allowance for U.S. Appl. No. 14/225,503, dated Jul. 20, 2016, 5 pages.
Official Action for U.S. Appl. No. 14/752,192, dated Jul. 8, 2016, 8 pages.
Notice of Allowance for U.S. Appl. No. 14/752,192, dated Sep. 16, 2016, 5 pages.
Official Action for U.S. Appl. No. 15/378,425, dated May 15, 2019, 82 pages.
Official Action for U.S. Appl. No. 15/378,425, dated Oct. 2, 2019, 41 pages.
Official Action for U.S. Appl. No. 15/378,425, dated Jul. 15, 2020, 21 pages.
Official Action for U.S. Appl. No. 15/378,425, dated Nov. 10, 2020, 29 pages.
Official Action for U.S. Appl. No. 15/385,278, dated Oct. 30, 2017, 23 pages.
Official Action for U.S. Appl. No. 15/385,278, dated Apr. 13, 2018, 18 pages.
Notice of Allowance for U.S. Appl. No. 15/385,278, dated May 31, 2018, 10 pages.
Official Action for U.S. Appl. No. 16/136,950, dated Nov. 25, 2019, 11 pages.
Official Action for U.S. Appl. No. 16/136,950, dated Jan. 31, 2020, 8 pages.
Official Action for U.S. Appl. No. 16/884,772, dated Sep. 30, 2021, 8 pages.
Notice of Allowance for U.S. Appl. No. 16/884,772, dated Feb. 22, 2022, 7 pages.
Official Action for U.S. Appl. No. 15/384,716, dated Nov. 1, 2017, 31 pages.
Notice of Allowance for U.S. Appl. No. 15/384,716, dated Apr. 2, 2018, 9 pages.
Official Action for U.S. Appl. No. 15/983,250, dated Mar. 5, 2019, 23 pages.
Official Action for U.S. Appl. No. 15/983,250, dated May 24, 2019, 21 pages.
Official Action for U.S. Appl. No. 15/983,250, dated Jan. 14, 2020, 8 pages.
Notice of Allowance for U.S. Appl. No. 15/983,250, dated Feb. 14, 2020, 8 pages.
Official Action for U.S. Appl. No. 16/904,056, dated Dec. 6, 2021, 12 pages.
Official Action for U.S. Appl. No. 16/904,056, dated May 17, 2022, 11 pages.
Notice of Allowance for U.S. Appl. No. 16/904,056, dated Aug. 11, 2022, 8 pages.
Corrected Notice of Allowance for U.S. Appl. No. 16/904,056, dated Aug. 24, 2022, 6 pages.
Official Action for U.S. Appl. No. 15/403,823, dated Oct. 30, 2017, 7 pages.
Official Action for U.S. Appl. No. 15/403,823, dated May 25, 2018, 9 pages.
Notice of Allowance for U.S. Appl. No. 15/403,823, dated Jun. 28, 2018, 9 pages.
Official Action for U.S. Appl. No. 16/160,336, dated Nov. 27, 2018, 6 pages.
Notice of Allowance for U.S. Appl. No. 16/160,336, dated Feb. 15, 2019, 7 pages.
Official Action for U.S. Appl. No. 16/423,375, dated Jul. 3, 2019, 6 pages.
Notice of Allowance for U.S. Appl. No. 16/423,375, dated Oct. 16, 2019, 8 pages.
Official Action for U.S. Appl. No. 16/782,364, dated Apr. 9, 2020, 5 pages.
Notice of Allowance for U.S. Appl. No. 16/782,364, dated Jul. 27, 2020, 7 pages.
Official Action for U.S. Appl. No. 16/917,096, dated Jul. 31, 2020, 5 pages.
Official Action for U.S. Appl. No. 16/617,096, dated Oct. 19, 2020, 8 pages.
Official Action for U.S. Appl. No. 17/027,953, dated Jan. 29, 2021, 5 pages.
Notice of Allowance for U.S. Appl. No. 17/027,953, dated Apr. 19, 2021, 8 pages.
Official Action for U.S. Appl. No. 17/337,600, dated Jul. 6, 2021, 5 pages.
Notice of Allowance for U.S. Appl. No. 17/337,600, dated Sep. 9, 2021, 7 pages.
Official Action for U.S. Appl. No. 17/835,204, dated Jul. 28, 2022, 6 pages.
Notice of Allowance for U.S. Appl. No. 17/835,204, dated Aug. 24, 2022, 7 pages.

(56) References Cited

OTHER PUBLICATIONS

Official Action for U.S. Appl. No. 17/848,759, dated Sep. 14, 2022, 6 pages.
Notice of Allowance for U.S. Appl. No. 17/848,759, dated Dec. 29, 2022, 7 pages.
Corrected Notice of Allowance for U.S. Appl. No. 17/848,759, dated Jan. 12, 2023, 4 pages.
Official Action for U.S. Appl. No. 17/854,422, dated Sep. 28, 2022, 7 pages.
Official Action for U.S. Appl. No. 17/854,422, dated Jan. 10, 2023, 6 pages.
"Poster Session I-IV Abstracts," American Society for Microbiology Conference on Biofilms, Nov. 13-17, 2022, Charlotte, NC, 226 pages.
Frey, "Why to avoid toothpastes with sodium lauryl sulfate," Hatcher & Frey Orthodontics, Nov. 6, 2012, retrieved from https://smile-365.com/why-to-avoid-toothpastes-with-sodium-lauryl-sulfate/, 5 pages.
Notice of Allowance for U.S. Appl. No. 18/143,399, dated Dec. 7, 2023, 7 pages.
Official Action for U.S. Appl. No. 18/232,433, dated Dec. 7, 2023, 20 pages.
Official Action for U.S. Appl. No. 18/232,980, dated Nov. 6, 2023, 14 pages.
Notice of Allowance for U.S. Appl. No. 18/232,980, dated Dec. 28, 2023, 7 pages.
Official Action for U.S. Appl. No. 18/234,132, dated Dec. 7, 2023, 8 pages.
Official Action for U.S. Appl. No. 18/235,686, dated Nov. 16, 2023, 7 pages.
Official Action for U.S. Appl. No. 18/234,544, dated Dec. 26, 2023, 8 pages.
Notice of Allowance for U.S. Appl. No. 18/234,132, dated Jan. 19, 2024, 7 pages.
Notice of Allowance for U.S. Appl. No. 18/232,433, dated Feb. 2, 2024, 8 pages.
Official Action for U.S. Appl. No. 18/535,722, dated Apr. 10, 2024, 6 pages.
Notice of Allowance for U.S. Appl. No. 18/235,686, dated Jan. 26, 2024, 8 pages.
Notice of Allowance for U.S. Appl. No. 18/234,544, dated Jan. 31, 2024, 7 pages.
Supplemental Notice of Allowance for U.S. Appl. No. 18/234,544, dated Feb. 22, 2024, 2 pages.
Auerbach et al., "Angiogenesis assays: Problems and pitfalls," Cancer and Metastasis Reviews, vol. 19, 2000, pp. 167-172.
Gura, "Systems for Identifying New Drugs Are Often Faulty," Science, vol. 278, No. 5340, Nov. 7, 1997, pp. 1041-1042.
Hennessy et al., "Statins as next generation anti-microbicals: Is there potential for repurposing?," Antimicrob. Agents Chemother., Jun. 20, 2016, 46 pages.
Jain, "Barriers to Drug Delivery in Solid Tumors," Scientific American, Jul. 1994, pp. 58-65.
Kilkkinen et al., "Use of antimicrobials and risk of type 1 diabetes in a population-based mother-child cohort," Diabetologia, vol. 49, 2006, pp. 66-70.
Kimoto et al., "New Lactococcus Strain with Immunnomodulatory Activity: Enhancement of Th1-Type Immune Response," Microbiol. Immunol., vol. 48, No. 2, 2004, pp. 75-82.
Malaguarnera et al., "Bifidobacterium longum with Fructo-Oligosaccharides in Patients with Non Alcoholic Steatohepatitis," Digestive Diseases and Sciences, vol. 57, 2012, pp. 545-553.
Norton et al., "The immune response to Lactococcus lactis: Implications for its use as a vaccine delivery vehicle," FEMS Microbiology Letters, vol. 120, No. 3, Jul. 15, 1994, pp. 249-256. Abstract only.
Repa et al., "Mucosal co-application of lactic acid bacteria and allergen induces counter-regulatory immune responses in a murine model of birch pollen allergy," Vaccine, vol. 22, No. 1, 2003, pp. 87-95. Abstract only.
Sporn et al., "Chemoprevention of cancer," Carcinogenesis, vol. 21, No. 3, 2000, pp. 525-530.
Zhao et al., "Microbiome-generated amyloid and potential impact on amyloidogenesis in Alzheimer's disease (AD)," Journal of Nature and Science, vol. 1, No. 7, 2015, pp. 1-5.
Official Action for U.S. Appl. No. 14/574,517 dated Jan. 6, 2016, 13 pages.
Notice of Allowance for U.S. Appl. No. 14/574,517, dated Apr. 15, 2016, 8 pages.
Corrected Notice of Allowance for U.S. Appl. No. 14/574,517, dated Jul. 7, 2016, 2 pages.
Official Action for U.S. Appl. No. 14/954,074, dated Jun. 30, 2016, 4 pages.
Notice of Allowance for U.S. Appl. No. 14/954,074, dated Jul. 20, 2016, 7 pages.
Official Action for U.S. Appl. No. 15/270,034, dated Apr. 6, 2017, 5 pages.
Notice of Allowance for U.S. Appl. No. 15/270,034, dated May 5, 2017, 7 pages.
Official Action for U.S. Appl. No. 15/392,173, dated Jan. 22, 2018, 8 pages.
Official Action for U.S. Appl. No. 15/392,173, dated Jul. 6, 2018, 13 pages.
Notice of Allowance for U.S. Appl. No. 15/392,173, dated Dec. 5, 2018, 8 pages.
Official Action for U.S. Appl. No. 16/229,252, dated Feb. 28, 2019, 5 pages.
Notice of Allowance for U.S. Appl. No. 16/229,252, dated Aug. 21, 2019, 7 pages.
Official Action for U.S. Appl. No. 16/722,117, dated Feb. 20, 2020, 6 pages.
Notice of Allowance for U.S. Appl. No. 16/722,117, dated Jul. 30, 2020, 8 pages.
Official Action for U.S. Appl. No. 17/011,175, dated Jun. 17, 2021, 9 pages.
Notice of Allowance for U.S. Appl. No. 17/011,175, dated Nov. 5, 2021, 8 pages.
Official Action for U.S. Appl. No. 17/023,736, dated Nov. 10, 2021, 7 pages.
Notice of Allowance for U.S. Appl. No. 17/023,736, dated Apr. 14, 2022, 8 pages.
Official Action for U.S. Appl. No. 17/893,384, dated May 9, 2023, 8 pages.
Official Action for U.S. Appl. No. 15/228,454, dated Sep. 23, 2016, 11 pages.
Notice of Allowance for U.S. Appl. No. 15/228,454, dated Jan. 23, 2017, 7 pages.
Official Action for U.S. Appl. No. 15/437,976, dated Mar. 29, 2017, 8 pages.
Notice of Allowance for U.S. Appl. No. 15/437,976, dated Jul. 12, 2017, 7 pages.
Official Action for U.S. Appl. No. 15/639,767, dated Aug. 14, 2017, 11 pages.
Official Action for U.S. Appl. No. 15/639,767, dated Sep. 27, 2018, 13 pages.
Notice of Allowance for U.S. Appl. No. 15/369,767, dated Feb. 15, 2019, 8 pages.
Official Action for U.S. Appl. No. 16/426,346, dated Aug. 2, 2019, 10 pages.
Official Action for U.S. Appl. No. 16/426,346, dated Jan. 13, 2020, 7 pages.
Notice of Allowance for U.S. Appl. No. 16/426,346, dated Mar. 25, 2020, 7 pages.
Official Action for U.S. Appl. No. 18/087,545, dated May 24, 2023, 5 pages.
Official Action for U.S. Appl. No. 18/615,672, dated Oct. 1, 2024, 11 pages.
Official Action for U.S. Appl. No. 17/567,295, dated Sep. 13, 2024, 6 pages.
Official Action for U.S. Appl. No. 17/694,775, dated Aug. 14, 2024, 8 pages.

(56) References Cited

OTHER PUBLICATIONS

Official Action for U.S. Appl. No. 17/836,079, dated Jul. 29, 2024, 22 pages.

* cited by examiner

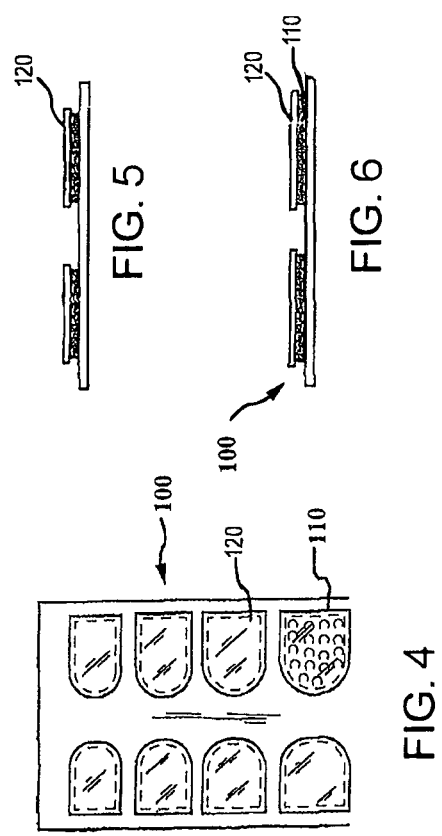

METHOD AND SYSTEM FOR INCREASING BENEFICIAL BACTERIA AND DECREASING PATHOGENIC BACTERIA IN THE ORAL CAVITY

RELATED APPLICATIONS

This application is a continuation-in-part of U.S. patent application Ser. No. 16/904,056, filed Jun. 17, 2020, which is a continuation-in-part of U.S. patent application Ser. No. 15/983,250 filed on May 18, 2018 (now U.S. Pat. No. 10,687,975, issued Jun. 23, 2020), which is a continuation-in-part of U.S. patent application Ser. No. 15/384,716 filed on Dec. 20, 2016 (now issued U.S. Pat. No. 9,987,224, issued Jun. 5, 2018), which claims priority of U.S. Provisional Patent Application Ser. No. 62/387,405, filed on Dec. 24, 2015.

This application is a continuation-in-part application of U.S. patent application Ser. No. 14/752,192 filed Jun. 26, 2015 (now U.S. Pat. No. 9,549,842, issued Jan. 24, 2017), which is a continuation-in-part application of U.S. patent application Ser. No. 14/225,503 filed Mar. 26, 2014, (now issued U.S. Pat. No. 9,445,936, issued Sep. 20, 2016), which is a continuation of U.S. patent application Ser. No. 13/367,052, filed Feb. 6, 2012 (now issued U.S. Pat. No. 8,701,671, issuing on Apr. 22, 2014), which claims priority of U.S. Provisional Patent Application Ser. No. 61/439,652, filed on Feb. 4, 2011 and U.S. Provisional Patent Application Ser. No. 61/556,023, filed on Nov. 4, 2011.

This application also is a continuation-in-part application of U.S. patent application Ser. No. 15/270,034, filed Sep. 20, 2016 (now U.S. Pat. No. 9,750,802, issued Sep. 5, 2017), which is a continuation-in-part application of U.S. patent application Ser. No. 14/954,074, filed on Nov. 30, 2015 (now issued U.S. Pat. No. 9,457,077, issuing on Oct. 4, 2016), which is a continuation-in-part application of U.S. patent application Ser. No. 14/574,517, filed on Dec. 18, 2014 (now issued U.S. Pat. No. 9,408,880, issuing on Aug. 9, 2016), which claims priority of U.S. Provisional Patent Application Ser. Nos. 62/072,476, filed on Oct. 30, 2014; 62/053,926, filed on Sep. 23, 2014; 62/014,855, filed on Jun. 20, 2014; and 61/919,297, filed on Dec. 20, 2013.

This application is also a continuation-in-part application of U.S. patent application Ser. No. 15/228,454, filed Aug. 4, 2016 (now U.S. Pat. No. 9,585,920, issued Mar. 7, 2017).

This application is a continuation-in-part of U.S. patent application Ser. No. 14/574,517 filed on Dec. 18, 2014, (now issued U.S. Pat. No. 9,408,880, issued Aug. 9, 2016), which claims priority of U.S. Provisional Patent Application Ser. Nos. 62/387,404, filed Dec. 24, 2015; 62/274,550, filed Jan. 4, 2016; and 62/275,341, filed Jan. 6, 2016.

This application is also a continuation-in-part application of U.S. patent application Ser. No. 14/611,458, filed Feb. 2, 2015 (now U.S. Pat. No. 10,398,209, issued Sep. 3, 2019), which is a continuation-in-part application of U.S. patent application Ser. No. 14/502,097, filed Sep. 30, 2014 (now issued U.S. Pat. No. 9,010,340, issuing on Apr. 21, 2015), which is a continuation of U.S. patent application Ser. No. 14/307,651, filed on Jun. 18, 2014 (now issued U.S. Pat. No. 8,936,030, issuing Jan. 20, 2015), which is a continuation-in-part application of U.S. patent application Ser. No. 14/079,054, filed Nov. 13, 2013 (now issued U.S. Pat. No. 8,757,173, issuing on Jun. 24, 2014), which is a continuation of U.S. patent application Ser. No. 13/425,913, filed Mar. 21, 2012 (now issued U.S. Pat. No. 8,584,685, issuing on Nov. 19, 2013), and claims priority of U.S. Provisional Patent Application Ser. No. 61/467,767, filed Mar. 25, 2011.

The entire disclosure of the prior applications are considered to be part of the disclosure of the accompanying application and are hereby incorporated by reference

FIELD OF THE INVENTION

A method and system for increasing beneficial bacteria populations in a subject's oral cavity and decreasing pathogenic bacteria to address a variety of diseases and conditions, thereby enhancing a person's oral and overall health, including through the use of oral strips that adhere to surfaces in the oral cavity and that include at least one of xylitol, *Lachnospira, Veillonella, Faecalibacterium* and/or *Rothia* bacteria, including bacteria transformed via a CRISPR system. Certain embodiments employ light to modify oral cavity bacterial populations, including the use of bioluminescent oral strips that promote the growth of beneficial bacteria and decrease pathogenic bacteria populations.

BACKGROUND OF THE INVENTION

The oral cavity is one of the most important interaction windows between the human body and the environment. The microenvironment at different sites in the oral cavity has different microbial compositions and is regulated by complex signaling, hosts, and external environmental factors, oral microbes can reflect human health and disease status in real-time and have important value in disease risk early warning and curative effect prediction. It is generally believed that low-grade inflammation in the oral cavity disturbs the health of the whole body and worsens other systemic diseases. In the general population, chronic periodontitis is a source of peripheral inflammation, often called a "low-grade systemic disease" affecting a variety of systemic diseases. Periodontitis is a risk factor for non-alcoholic fatty liver and *P. gingivalis* plays a significant role in the course of non-alcoholic fatty liver. The intestinal microbiome of patients with liver cirrhosis shows a large number of oral microorganisms, including *Veillonella, Streptococcus, Prevotella, Haemophilus, Lactobacillus,* and *Clostridium*. The invasion of *P. gingivalis* into the intestine changes the composition of the intestinal microbiome, increases the permeability of the intestinal mucosa, contributes to insulin resistance, leads to the spread of intestinal bacteria to the liver, and increase the content of triglycerides in liver tissue.

The human microbiota is principally formed by four phyla—Actinobacteria, Firmicutes, Proteobacteria, and Bacteroidetes—which colonize the oral cavity, esophagus, skin, vagina, and gut, with bacteria being the most prominent. The microbiota undergoes growth rate fluctuations due to changes, e.g. in diet, vigorous cleaning and disinfection, lifestyle, antibiotics, and diseases. Bacteria can modulate tissue signaling pathways and immune cell responses and they produce vitamins (i.e., cobalamin) and bacteriocins. The oral commensal microbiota plays a key role in maintaining oral and systemic health through bacteriocin and biofilm formation against pathogens. The oral ecosystem is home to several hundreds of microbial species that normally exist in homeostasis. The oral microbiome plays vital roles in human physiology and health and the oral microbial community is responsive to shifts in the local environment, resulting in dysbiosis and disease. The oral cavity, as the beginning of the gastrointestinal structure, is an open system which possesses a varied landscape ranging from hard teeth to the soft gum, stiff palate to the flexible cheeks, contributing to a varied biogeography in its flora, with thousands of species inhabiting site-specific spatial arrangements in each of the oral landscapes.

When there exists bacterial dysbiosis in the oral cavity, opportunistic pathogens such as *Candida* spp. and *Staphylococcus* spp. can wreak havoc, including cariogenic properties by *Streptococcus mutans, Actinomyces naeslundii, Propionibacterium* spp., and *Lactobacillus* spp., as well as halitosis by *Streptococcus salivarius*. Periodontitis is caused by the colonization of the periodontal pocket with one or more of *Porphyromonas gingivalis, Treponema denticola, Anaeroglobus geminatus, Tannerella forsythia, Filifactor alocis, Eubacterium saphenum, Prevotella denticola, Prevotella intermedia*, and *Porphyromonas endodontalis*. The presence of *Helicobacter pylori* in dental plaques is directly associated with gastric infection. *P. gingivalis* and *Fusobacterium nucleatum* are also prevalent in oral cancers. Oral infection also provides bacteria access to the bloodstream to cause various diseases, such as infectious endocarditis; brain, kidney, and liver abscesses; rheumatoid arthritis; Alzheimer's disease and dementia.

The oral microbiome is therefore an access point for treating a variety of human ailments, such as sore throat, headaches, depression, neurological conditions, dementia, etc.

The number of people with sore throats in the United States that seek medical attention is an estimated 120 million visits per year. Approximately 12 to 25 percent of those individuals have positive strep cultures. Far more individuals than those diagnosed with strep throat are placed on antibiotics because there are no other available treatments. *Streptococcus* is one of the most frequent causes for visits to the doctor's office in the United States. It is also one of the most frequent reasons for antibiotic use. *Streptococcus* is also a concern due to the development of not only throat infections, but also due to the other sequella of the infection, namely rheumatoid heart disease. This is where the organism invades the blood stream and causes vegetations on the heart valves.

*Streptococcus* is a genus of spherical, Gram-positive bacteria that are known to be the primary cause of throat infections in humans. Streptococcal sore throat, or strep throat as it is more commonly called, is an infection of the mucous membranes lining the pharynx. Sometimes the tonsils are also infected (tonsillitis). *Streptococcus pyogenes*, a group A *Streptococcus* (GAS), is the causative agent in Group A for Streptococcal infections including strep throat, acute rheumatic fever, scarlet fever and acute glomerulonephritis (inflation of the glomeruli). The reason why *S. pyogenes* sometimes causes disease is not entirely understood, but both bacterial virulence factors and host factors are thought to contribute. The microbiota is one such host factor that needs further investigation. Attachment to epithelial cells is the crucial initial step of colonization because non-adherent GAS is removed by mucus and saliva flow.

Conventional therapy for *S. pyogenes* infections has mainly consisted of treatment with antibiotics such as penicillin and tetracycline. The large numbers of people that are prescribed antibiotics for this illness helps to increase the incidence of resistant bacteria as observed in rising levels of antibiotic resistant infections in the public. Antibiotics that were once almost universally effective against these infections are now approximately 70 to 80% effective. Moreover, antibiotics such as penicillin and tetracycline, exhibit broad spectrum antimicrobial activity. Thus, treatment with these antibiotics tends to kill not only *S. pyogenes* but a number of other bacterial species, some of which may actually be beneficial to the body. Although *S. pyogenes* may be treated using antibiotics, a prophylactic vaccine to prevent the onset of disease has been desired. Efforts to develop such a vaccine have been ongoing for many decades, but yet, to date, there are no GAS vaccines available to the public. There are well acknowledged downsides of antibiotic use to treat bacterial conditions in the oral cavity, including antibiotic resistance, antibiotic toxicity, and allergies. There is a long felt but unsolved need for a preventative treatment for sore throat and especially one that does not present the problems associated with the use of antibiotics.

A further condition that may be treated by modifying the microbiota of the oral cavity is that of headaches and migraines. Migraine headaches have a prevalence of 10% in the general population with a lifetime prevalence of 13% in men and 33% in women. Migraine is a highly disabling disease with high personal and social costs. To date, the precise mechanisms underlying the pathophysiology of migraine have remained elusive. Migraine strikes people during what are expected to be their most productive years: between ages 20 and 40 for most women, with a slightly higher age range for men. Migraine is typically characterized by unilateral onset of head pain, severe progressive intensity of pain, throbbing or pounding, and interference with the person's routine activities. Accompanying symptoms of photophobia (sensitivity to light) or phonosensitivity (intolerance to noise), as well as nausea and/or vomiting, are common, and often leads to the inability to perform daily tasks. A large portion of people with migraine often have no accompanying pain, their predominant symptom instead being vertigo (a spinning sensation) or dizziness/disequilibrium (balance loss), mental confusion, disorientation, dysarthria, visual distortion or altered visual clarity, or extremity paresis. Patients with migraine associated vertigo (MAV) are often seen by audiologists and vestibular rehabilitation therapists for evaluation and treatment. Because the exact mechanisms of migraine are still not completely understood, the management of migraine dizziness presently includes a combination of medications, vestibular rehabilitation, and lifestyle modifications that include limitation of risk factors associated with migraine (those related to diet, sleep, stress, exercise, and environmental factors).

Migraine is a disease associated with increased synthesis and release of calcitonin gene related peptide (CGRP) and a migraine attack can be blocked with CGRP antagonists. The actual pain is generated by nociceptors of trigeminal nerve endings in the dura. Low serotonin levels may sensitize the nociceptors of trigeminal neurons. Triptans and ergotamins, which decrease serotonin, are associated with relief of acute pain. In contrast, tricyclic antidepressants and selective serotonin and noradrenaline reuptake inhibitors, which are associated with increases in serotonin, are utilized for migraine prevention.

Migraine attacks can be triggered by intrinsic cerebral factors (e.g. calcitonin gene related peptide (CGRP) release), nitric oxide like tri-nitroglycerine, corticotrophin releasing hormone (stress), pro-inflammatory cytokines, and degranulation of mast cells located in the dura. While migraine has a genetic background, twin studies reveal that the cause of a majority of migraines appears to be due to environmental factors. The mechanism of triggering migraine is, however, still not understood. The cause of both migraines and chronic dizziness has eluded investigators for centuries and it therefore presents a truly long felt but unsolved mystery as to its causation and treatment.

Yet another condition that is associated with the human microbiome, and in particular the oral microbiome, is depression. According to the World Health Organization, major depressive disorder (MDD) is a complex debilitating psychiatric disorder that is estimated to account for approximately 10% of worldwide disability. Classic symptoms include depressed mood, anxiety, anhedonia, and cognitive impairments that profoundly affect patients' quality of life. Despite major investments over the last decades into understanding the etiology, progression, and biology of this disorder, its molecular and cellular bases remain poorly defined. There is an increasing emphasis on the fact that depression does not affect brain function exclusively, but manifests as a whole-body disorder affecting almost all of the major corporeal systems.

Still other human health conditions that are impacted by the oral microbiome include Alzheimer's disease. The clinical manifestations of Alzheimer's disease begin with subtle short-term memory deficits and depressive symptoms, followed by orientation and language difficulties. Intellectual functions progressively disappear and patients become entirely dependent, typically surviving in this devastating state for more than a decade. Death generally occurs from a secondary infection, frequently from pneumonia or urinary infection. The duration of the disease from the appearance of the first symptoms and the manifestation of dementia varies between 5 and 20 years. Clinical diagnosis of Alzheimer's disease often occurs long after the onset of the disease. It is usually first noticed by immediate family members who detect problems with short-term memory and unusual behavior. Confirmation is achieved post-mortem by detecting the presence of the pathological hallmarks of the disease, amyloid plaques and neurofibrillary tangles.

Recent research has shown that light may impact bacteria in various ways. There is a need for novel treatments of the oral microbiome using light in a fashion that can improve the bacterial populations of an individual's oral cavity.

SUMMARY OF THE INVENTION

One embodiment of the present invention is directed to a method to facilitate the growth of desired bacteria in a human's mouth to limit the number of pathogenic bacteria, to maintain oral health and to establish a biofilm in a human subject's mouth, such method involving, after a human subject has cleaned their teeth, providing to the human subject a bacterial composition that includes beneficial bacteria adapted to form a biofilm, with such beneficial bacteria including a bacterium of the genus *Rothia*. Preferably, the bacterial composition does not inhibit growth of a second bacterium selected from at least one of the species *Streptococcus mutans* and *Lactobacillus fermentum*. Moreover, preferably a buccal bioadhesive strip is used that has one side with a bioadhesive that is adapted to bind to a mucosal membrane for at least 1 hour while inside the human subject's mouth. Such strip may include one or more encapsulated features containing a bacterial composition as described herein.

One aspect of various embodiments of the present invention is directed to the buccal mucoadhesive delivery of lactic bacteria and bifidobacterial. While not bound by theory, it is believed that lactic bacteria and bifidobacteria are capable of compromising the vitality of pathogenic microorganisms through modulating the pH and/or oxidation-reduction potential of the environment in which they live, stimulating non-specific immune mechanisms and modulating humoural and cellular immune response. At least certain strains of *Lactobacillus brevis* are capable of producing quantities of arginine deiminases and sphingomyelinases, believed to be capable of compromising the vitality of pathogenic microorganisms through modulating the pH and/or oxidation-reduction potential of the environment and stimulating non-specific immune mechanisms. Because eukaryotic cells also use arginine to produce nitric oxide (NO), an important mediator of the inflammatory process, removal of the precursor arginine from the cellular environment can significantly reduce the production of NO and thus modulate the inflammatory response. Various embodiments of the present invention are directed towards and effective way of administering lactic bacteria and bifidobacteria in a fashion such that they are present for effective times and concentrations to effect positive and beneficial results. In various embodiments, the mucosal adhesive strips or patches described herein, provide for mucosal and buccal treatments with probiotic such that it is possible to localize release of the bacteria and the beneficial substances which they produce.

Certain aspects of the present invention are directed to a method for reducing the likelihood of developing depression in an individual. Such method involves providing either orally or in the gut of an individual a population of beneficial bacteria selected from the group consisting of bacterial species able to make small chain fatty acids, and preferably butyrate, and administering fiber to the individual to maintain a therapeutically effective amount of the beneficial bacteria in the gut of the individual. The individual's gut microbiome is modified to reduce the number of undesired bacteria and to increase the number of beneficial bacteria. Bacteria are preferably modified to remove one or more virulence facts or alternatively to produce increased amounts of SCFA's, such as butyrate. Beneficial bacteria may be encapsulated in a frangible enclosure to ensure they arrive in an individual's body while still viable, e.g. such as being first released in the lower gut rather than being exposed to the harsh conditions of an individual's stomach. In other embodiments, a therapeutically effective amount of a bacterial formulation comprising *Faecalibacterium prausnitzii* is administered. Other embodiments include the administration of a bacterial formulation comprising at least one of *Coprococcus, Roseburia, Bifidobacterium, Faecalibacterium prausnitzii* and *L. casei* to treat depression.

In one embodiment, an individual's gut is provided with a population of beneficial bacteria selected from the group consisting of *Lactobacillus* species and such individual is further administered a fiber that maintains a therapeutically effective amount of the beneficial bacteria in the gut of the individual. In preferred embodiments, the individual is administered a therapeutically effective amount of a bacterial formulation of beneficial bacteria comprising at least one of *Coprococcus, Veillonella, Roseburia, Bifidobacterium, Faecalibacterium prausnitzii, Lactobacillus rhamnosus* and *Prevotella*. In another preferred embodiment, the individual is administered bacteria that generate short-chain fatty acids, preferably at least one of lactate, propionate and butyrate, and most preferably, butyrate. In other embodiments, the individual is administered *Coprococcus* bacteria, alone or in conjunction with other bacteria.

Certain embodiments of the present invention are directed to a method for reducing the likelihood of developing depression in an individual, by providing in the gut of an individual at least two bacteria from a population of beneficial bacteria selected from the group consisting of *Coprococcus, Veillonella, Roseburia, Bifidobacterium, Faecalibacterium prausnitzii* and *Prevotella*; and administering fiber to the individual to maintain a therapeutically effective amount of the beneficial bacteria in the gut of the individual. Still further embodiments include increasing the levels of at least one of *Roseburia, Coprococcus, Veillonella, Bifidobacterium, Lactobacillus,* and *Prevotella* in the individual's gut microbiome.

Thus, one aspect of the present invention is to modify the gut microbiome of an individual, via introduction of beneficial bacteria, whether from one species or several that together form a more beneficial mix of bacteria that produce beneficial metabolites, such as small chain fatty acids, such as butyrate. SCFAs are a major energy source for the epithelial cells lining the colon, which keep contents from leaking out of the gastrointestinal tract into the body. SCFAs are thought to play a role in protecting individuals from common problems like inflammation, obesity and diabetes. Other aspects involve decreasing the number of bacteria believed not to be beneficial as to the treatment of depression and/or hypertension. Still other embodiments involve the manipulation of bacteria, preferably using CRISP systems, to either increase or decrease the production of bacterial products. For example, enhancing the production of SCFA's by bacteria, whether they are bacteria that normally produce at least some SOFA or not, is done via CRISPR systems to decrease the likelihood that an individual may suffer from depression and/hypertension. In certain embodiments, the present invention is directed to a method for reducing the likelihood of developing depression in an individual involves providing in the gut of an individual a population of beneficial bacteria selected from the group consisting of bacterial species able to make small chain fatty acids, and preferably butyrate, and administering fiber to the individual to maintain a therapeutically effective amount of the beneficial bacteria in the gut of the individual. The individual's gut microbiome is modified to reduce the number of undesired bacteria and to increase the number of beneficial bacteria. Bacteria are preferably modified to remove one or more virulence facts or alternatively to produce increased amounts of SCFA's, such as butyrate. Beneficial bacteria may be encapsulated in a frangible enclosure to ensure they arrive in an individual's body while still viable, e.g. such as being first released in the lower gut rather than being exposed to the harsh conditions of an individual's stomach. In other embodiments, a therapeutically effective amount of a bacterial formulation comprising *Faecalibacterium prausnitzii* is administered. Other embodiments include the administration of a bacterial formulation comprising at least one, and preferably at least two or more of *Coprococcus, Veillonella, Roseburia, Bifidobacterium, Faecalibacterium prausnitzii* and *Prevotella* to treat depression.

Particular embodiments of the invention are directed to a method for reducing the likelihood of depression in an individual human being by first substantially reducing the human being's resident populations of gut microbes prior to administering a therapeutically effective amount of a bacterial formulation comprising *Coprococcus*, followed by fiber, preferably providing fructan fiber inulin, in an amount sufficient to reduce the pH in the colon of the human being to achieve acidifying of the colon.

Preferably the bacterial formulation is encapsulated. Moreover, the *Coprococcus* bacteria employed are first isolated from a human being's stool and more preferably are from the human being treated. Certain embodiments include the reduction of *Helicobacter pylori* populations in the individual human being, whether via antibiotics or by employing a clustered regularly interspaced short palindromic repeats (CRISPR) CRISPR associated protein (Cas) system or a CRISPR from *Prevotella* and *Francisella* 1 (Cpf1) system.

Foods particularly high in dietary fibers and polyphenols are preferably provided to the individual to maintain the beneficial bacteria. In particular, bacteria of the genera *Faecalibacterium, Bifidobacterium, Lactobacillus, Coprococcus,* and *Methanobrevibacter* are preferably established and maintained in the individual's gut. Certain embodiments of the invention include the enhancement of the production by one or more of these bacteria so as to increase the production of lactate, propionate and/or butyrate so as to inhibit biofilm formation and/or the activity of pathogens. CRISPR-Cas and/or Cpf1 may be employed to provide such characteristics to the selected bacterial species in this regard. In various embodiments of the present invention, these bacterial species are selected and administered to an individual in preferred ratios that reflect those of healthy individuals so as to attain the general balance of bacterial populations in a person's gut.

The beneficial bacteria as described herein are preferably modified to produce increased amounts of short-chain fatty acids, preferably butyrate, and may also be encapsulated in a frangible enclosure for administration. In still other embodiments, the level of *Roseburia* are preferably increased. In other embodiments, the levels of Akkermansia spp. in the individual's gut microbiome are increased. In still other embodiments, a therapeutically effective amount of a bacterial formulation comprising *Faecalibacterium prausnitzii* is administered, or a composition comprising modified *L. reuteri* bacteria having the ability to survive conditions in the duodenum or jejunum of the individual's small intestine.

Given the role of vagal nerve stimulation as a treatment in some cases of depression, a role for vagal stimulation in the mechanism of action of certain probiotics forms a central feature of still other embodiments of the present invention. It is believed that the vagus nerve is partially responsible for some of the effects of gut microbiota in depression. Thus, one aspect of the present invention is directed to the targeted intervention to an individual's microbiome to facilitate brain health, including administering probiotics, e.g. including *Lactobacillus* and *Bifidobacterium*, in conjunction with a prebiotic to maintain such bacteria in the individual's gut. Such an intervention is believed to promote an individual's resilience to stress and ameliorate emotional responses, including treating such individual's depression.

Still further embodiments are directed to a method for reducing the likelihood of developing depression in an individual by providing in the gut of an individual at least two bacteria from a population of beneficial bacteria selected from the group consisting of *Coprococcus, Roseburia, Bifidobacterium,* and *Faecalibacterium prausnitzii*; and administering fiber to the individual to maintain a therapeutically effective amount of the beneficial bacteria in the gut of the individual. Preferably, the at least two bacteria are encapsulated.

In other embodiments, the use of CRISPR-Cas systems is employed to increase butyrate production of select bacteria. For example, *F. prausnitzii*, one of the most abundant species in the colon, is an important producer of butyrate, a major product of carbohydrate fermentation which is implicated in providing protection against colorectal cancer and ulcerative colitis. CRISPR systems are used to enhance the production of butyrate by insertion of genes into select *F. prausnitzii* bacteria to protect against colorectal cancer and other diseases—including reducing the likelihood of depression in an individual.

Because CRISPR-Cas/Cpf1 acts before transcription occurs, it is able to be employed to target regulatory and other elements on the DNA of microbes that make up a person's gut microbiome. In certain embodiments, CRISPR-Cas may be employed to deliver fluorescent markers to certain DNA sequences, thus permitting one to determine whether any particular sample has been treated in accordance with the present invention, thus ensuring, for example, identity of various materials, compliance with safety issues, effectiveness of gene expression or excision, etc. permitting labeling of living cells with a desired color to discern particular attributes and states.

Other embodiments are focused on diet as it relates to the use of probiotics. The gut microbiota plays a critical role in transforming dietary polyphenols into absorbable biologically active species, acting on the estimated 95% of dietary polyphenols that reach the colon. Certain embodiments rely upon the ability to deliver agents via mucosal adhesive strips, such as described, for example, in U.S. Pat. No. 8,701,671, which is fully incorporated herein by this reference. Thus, in various embodiments of the present invention, the engineering of communal bacteria with improved properties using a CRISPR/Cas system is employed to provide for the enhancement of health, especially as it relates to an individual's microbiome. In certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene, and most preferably the nucleotide sequence of interest comprises 16S ribosomal DNA (rDNA). In various embodiments, the delivery vehicle is a bacteriophage. Thus, various embodiments of the present invention include the use of CRISPR-Cas, with the recognition that this system can be employed to benefit human health by modifying the bacterial and other microbe communities that humans have long been exposed to in a fashion such that the beneficial aspects of such microbes can be preserved, while the disadvantageous aspects can be "cut out" of the microbe DNA—rather than attempting to change or modify the DNA of a human.

Moreover, in preferred embodiments, the microbes modified are limited to those demonstrating human tropism such that undesired and unintended changes to other animals and organisms are not affected and that the only implications of such genomic alterations of human specific pathogens are restricted to such species in a manner that is not capable of affecting other than the particular human disease at issue. This can include, for example, modifications and/or employment of integrons, which are a two-component genetic recombination system present in the chromosome of many bacterial species. The integron incorporates mobile genes termed gene cassettes into a reserved genetic site via site-specific recombination, named the Integron/gene cassette system. The integron consists of three basic elements: an integrase gene, an attachment site and a promoter. These elements can be manipulated to, for example, decrease the ability of a particular bacteria in a person's gut from being able to effectively attach to epithelial tissue; or alternatively, to coaggregate with other bacteria.

To provide necessary and sufficient written disclosure and enablement of the various embodiments of the present invention, the following references are incorporated by reference in their entireties: U.S. Pat. No. 9,017,718 to Tan; 20140065218 to Lang et. al.; U.S. Pat. Nos. 6,599,883; 8,383,201; 5,158,789; 20070218114 to Sorousch; 20040136923 to Davidson; U.S. Pat. No. 8,999,372 to Davidson; 20090196907 to Bunick; 20090196908 to Lee; 20030124178 to Haley; 20070293587 to Haley; 20100285098 to Haley; 2006-0204591 to Burrell; U.S. Pat. No. 7,087,249 to Burrelll; U.S. Pat. No. 6,210,699 to Acharya; U.S. Pat. No. 8,865,211 to Tzannis; 20140199266 to Park; U.S. Pat. No. 6,599,883 to Romeo; PCT/US2008/080362 to Dussia; 2007-0218114 to Duggan; 20040136923 to Davidson; 20110142942 to Schobel; 20040120991 to Gardner et al.; Fuchs et al. U.S. Pat. No. 4,136,162; 20040136923 to Davidson; U.S. Pat. No. 4,163,777 to Mitra; U.S. Pat. No. 5,002,970 to Eby, III; 20040096569 to Barkalow et al.; 20060035008 to Virgallito et al.; 20030031737 to Rosenbloom; U.S. Pat. No. 6,919,373 to Lam et al.; 20050196358 to Georglades et al.; U.S. Pat. No. 3,832,460 to Kosti; 2002002057 to Battey et al.; 20040228804 to Jones, et al.; U.S. Pat. No. 6,054,143 to Jones; U.S. Pat. No. 5,719,196 to Uhari; 20150150792 to Klingman; 20140333003 to Allen; 20140271867 to Myers; 20140356460 to Lutin; 20150038594 to Borges; U.S. Pat. No. 6,139,861 to Friedman; 20150216917 to Jones; 20150361436 to Hitchcock; 20150353901 to Liu; U.S. Pat. No. 9,131,884 to Holmes; 20150064138 to Lu; 20150093473 to Barrangou; 20120027786 to Gupta; 20150166641 to Goodman; 20150352023 to Berg; 20150064138 to Lu; 20150329875 to Gregory; 20150329555 to Liras; 20140199281 to Henn; US20050100559 (proctor and Gamble); 20120142548 to Corsi et al.; U.S. Pat. Nos. 6,287,610, 6,569,474, US20020009520, US20030206995, US20070054008; and U.S. Pat. No. 8,349,313 to Smith; and U.S. Pat. No. 9,011,834 to McKenzie; 20080267933 to Ohlson et. al.; 20120058094 to Blasser et. al.; U.S. Pat. No. 8,716,327 to Zhao; 20110217368 to Prakash et. al.; 20140044734 to Sverdlov et al.; 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849 and WO 2013026000 to Bryan; 20190070225 to Strandwitz, et. al.; and 202/00132270 to Bolte; 20070280964 and 20070098744 to Knorr, et. al.; 20210386659 to Kim; 20200155447 to Edwards; 20220031590 to Pesaro, et. al.

Preferably, the modified bacteria employed in certain embodiments of the present invention are administered orally to a patient in order to deliver the therapeutic directly to the site of inflammation in the gut. The advantage of this approach is that it avoids systemic administration of immunosuppressive drugs and delivers the therapeutic directly to the gastrointestinal tract. The viability and stability of such modified bacteria is preferably enhanced to support the production of such microbes of desired agents or therapeutic molecules, e.g. butyrate, SOFA, tomatidine, p53 protein, etc. and by doing so, a method is provided that reduce gut inflammation, enhance gut barrier function, and/or treat or reduce the incidence of depression, autoimmune disorders, inflammatory related diseases, etc. Preferably, such modified bacteria are capable of producing therapeutic anti-inflammation and/or gut barrier enhancer molecules, particularly in the presence of reactive nitrogen species, and more preferably the bacteria are functionally silent until they reach an environment containing local RNS, wherein expression of the therapeutic molecule is induced. In certain embodiments, the genetically or CRISPR engineered bacteria are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate, is produced, which induces the differentiation of regulatory T cells in the gut and/or promotes the barrier function of colonic epithelial cells. Use of such modified bacteria, especially those modified via CRISPR-Cas systems, provides a way to generate a desired therapeutic effect in a manner that lowers the safety issues associated with systemic exposure.

The ties between obesity, inflammation and depression are largely acknowledged, as discussed herein. In certain embodiments, the provision of effective amounts of tomatidine is rendered available to an individual via the inoculation of the individual's microbiome (e.g. oral or gut) by particular bacteria that have been modified to express amounts of tomatidine. Still other embodiments also involve the reduction in the amount of acetate levels in an individual's body, which in turn lowers the amount of insulin the individual will produce, which has the effect of keeping fat cells from storing more energy in the form of fat. The reductions in the amount of acetate available in an individual's body further reduces the amount of the hormone ghrelin, thus reducing the hunger drive of the individual. Thus, the modification of an individual's microbiome influences various aspects of their metabolism in a manner that not only retains and maintains the ability to nurture muscle tissue, but to also reduce obesity by affecting the amount of fat that the body stores. While not bound by theory, it is believed that the gut bacteria of an individual is a substantial source of acetate production. The production of acetate by gut microbes is believed to send signals to the brain of the individual to initiate the production of insulin, conveyed via the vagus nerve. Fine tuning of the amount and type of gut microbes (e.g. via the use of antibiotics to initially reduce the kind and numbers of undesired bacteria, followed by purposeful inoculation of an individual's gut microbiome with modified microbes, e.g. via CRISPR-Cas insertion of particular factors, proteins, etc., such as tomatidine) is an effective way to address not only muscle wasting issues, but also hypertension and obesity issues of individuals.

While there are many gut bacteria that produce acetate and butyrate, particular bacteria are preferably selected and even more preferably are modified using CRISPR-Cas systems to address the levels of acetate and/or butyrate production once such bacteria are introduced (or enhanced) to an individuals' microbiome. Preferably the gut microbiota are members of two bacterial divisions: the Bacteroidetes and the Firmicutes, and most preferably include *F. prausntizii*. The modification of an individual's gut microbiome is directed in a manner such that the typical increase seen in the relative abundance of the Firmicutes and a corresponding division-wide decrease in the relative abundance of the Bacteroidetes in obese individuals, is addressed. Obese people have more Firmicutes and almost 90% less Bacteroidetes than the lean people. Preferably, the administration of modified Bacteroidetes is achieved to more substantially reflect gut populations in more lean individuals, and by doing so, reducing the amount of acetate produced by the overall gut microbiome. Such a shift in the population of gut microbes to favor Bacteroidetes over Firmicutes, whether or not coupled with the administration of tomatidine, is one aspect of the present invention's objective of achieving a greater proportion of muscle mass than fat that would otherwise occur in any given individual. In still other embodiments, addressing the acetate production by especially Firmicutes, which has an increased capacity for fermenting polysaccharides relative to the lean-associated microbiome, is another way to achieve this objective, and addresses the significant obesity issues especially prevalent in Western societies.

In yet another embodiment, encapsulated structures, preferably microencapsulated structures, are employed that are filled with desired agents, including but not limited to tomatidine, butyrate, etc. and/or microbes, especially bacteria that are found in an individual's gut microbiome, such as *F. prausntizii*, such that effective amounts of the agents can be administered to treat particular diseases. Other agents may include those effective in combatting cancer, such as but not limited to tomatidine, p53 protein, statins, PTEN, rapamycin, and other agents able to treat cancer symptoms. Preferably, the bacteria comprise bacteria that are found in the communities of healthy humans, including, for example, *F. prausntizii, Streptococcus, Actinomyces, Veillonella, Fusobacterium, Porphromonas, Prevotella, Treponema, Neisseria, Haemophilus, Eubacteria, Lactobacterium, Capnocytophaga, Eikenella, Leptotrichia, Peptostreptococcus, Staphylococcus,* and *Propionibacterium*. Such encapsulated structures may be provided as strips that may be manufactured to have desired dissolvable aspects thereto and that further have encapsulated portions that house the desired agents.

Certain other embodiments of the present invention are directed to treating sore throats in humans. A method and system to prevent sore throat infections in humans includes the administration of an active ingredient to a site on the mucus membranes of the throat of a human that inhibits adherence and promotes desorption of *S. pyogenes* to soft tissue surfaces, such as the pharyngeal and oral mucosa of a human. A mucoadhesive strip having a surface topography that resists bioadhesion of undesired bacteria that are typically present in a human's mouth is preferably employed and that has one or more encapsulated agents selected from the group consisting of an antibiotic; lactic acid bacteria; *S. pyogenes* modified by a CRISPR-Cas system to reduce one or more virulence factors; and a breath mint solution.

In certain other embodiments, *Lactobacillus rhamnosus* and/or *Bifidobacterium animalis* are employed to advance the health of an individual, in particular, in preventing sore throat.

A buccal bioadhesive strip is preferably used that has a first and a second side, with the first side preferably having a surface comprising a pattern defined by a plurality of spaced apart features each having at least one microscale dimension and having at least one neighboring feature having a substantially different geometry, and wherein an average spacing between adjacent ones of said features is between 0.5 and 5 .mu.m in at least a portion of the surface. The first side has a bioadhesive that is adapted to bind to a mucosal membrane for at least 1 hour while inside a person's mouth. The strip may, for example, extend over a majority of the soft palate and preferably includes xylitol. Other embodiments have the strip including at least one encapsulated pocket containing one of an analgesic, a lactic acid bacteria, or another of the desired bacteria as described herein.

Various embodiments of the present invention are directed to a method and system that a person can employ when they first fear they may be coming down with a sore throat or just prior to full blown feelings of a sore throat. The application of a strip to the soft palate region of their throat is believed to eliminate the chances they will experience and suffer a sore throat. This is because the strips as described herein are effective in diminishing, if not precluding or prohibiting the growth of particular bacteria, especially *S. pyogenes*, which is largely responsible for sore throats. The provision on or in such strip of certain sugars, including xylitol but also certain other oligosaccharides, in concert with other structural features of the surface of such strip that make bacteria avoid such surface, because they cannot adhere well thereto, prevents the continued progression of a sore throat that a person would otherwise experience. Moreover, in certain other embodiments, coaggregation of *S. pyogenes* is achieved by populating the strip with an effective amount of preferred lactic acid bacteria (LAB) that are able to coaggregate specifically with *Streptococcus pyogenes*. Coaggregation is understood in the sense of the invention in particular as adhesion, interaction, binding, specific binding, affinity or interaction and characterizes in particular the ability of the preferred microorganisms to form agglomerates with *Streptococcus pyogenes*. *S. pyogenes* has evolved a number of different types of molecules, referred to as "adherens," on its surface which can very tightly stick to one or more molecules that are part of the host's various surfaces. Few strains of *Lactobacillus* are capable of preventing the binding of *Streptococcus pyogenes* (group A streptococci, also referred to as GAS) GAS to human cell lines. The *Lactobacillus* strains compete with GAS for surface structures on the cells and thus prevent GAS from invading the host cells. Adhesion of *Streptococcus pyogenes* to the host cell is the first step in pathogenesis, and the invasion process into the host cells takes place in very short order. The early use of therapeutic agents for prevention and treatment are of crucial importance to reduce the total GAS microbe count and to efficiently prevent the binding, i.e., invasion of *Streptococcus pyogenes*, is one objective of the present invention. Use of certain LAB in various aspects of the present invention preferably involves the following microorganisms deposited with the German Collection for Microorganisms and Cell Cultures under the code numbers DSM 25972, DSM 25987, DSM 25988, DSM 25989, DSM 25973.

One objective is to decrease the colonization of the oropharynx, and therefore decrease symptoms of the sore inflamed throat and ultimately decrease the need for antibiotics. In certain embodiments of the present invention, conjugated oligosaccharides are employed to specifically inhibit the adherence of *S. pyogenes* to pharyngeal and oral mucosal cells. In the first stages of infection, bacterial adhesins, adhesive molecules on the surface of bacteria, bind to receptor materials on the host cell membrane. Thus, certain embodiments of the present invention are directed to defeating the adherence of *S. pyogenes* to a person's oral tissue in a manner that results in avoiding a sore throat.

Pathogenic bacteria display various levels of host specificity or tropism. While many bacteria can infect a wide range of hosts, certain bacteria have strict host selectivity for humans as obligate human pathogens. Host specificity of bacterial pathogens is determined by multiple molecular interactions between the pathogens and their hosts. A number of bacteria are highly adapted to the human environment and display strict host selectivity for humans, including *Haemophilus influenzae*, *Helicobacter pylori*, *Neisseria gonorrhoeae*, *Neisseria meningitidis*, *Mycobacterium leprae*, *Salmonella Typhi*, *Streptococcus pneumoniae*, *Streptococcus pyogenes*, *Vibrio cholerae* and *Treponema pallidum*. Hereinafter these bacteria will be referred to as human-specific pathogens. The cause of strep throat, *Streptococcus pyogenes*, exhibits tissue tropism, i.e. it is virtually found only in humans. One aspect of the present invention, described in detail with respect to sore throat infections but not to be intended to be so limited, is the modification of human specific pathogens to alter or destroy their respective virulence factors, preferably by employing CRISPR-Cas systems, and in so doing, alleviating diseases caused by such microbes without the threat of undesired consequences stemming from a more global and universal modification of bacteria serving other beneficial functions in our environment. In certain embodiments CRISPR-Cas is employed to silence or to delete certain virulence factors of microbes, specifically the virulence factors of *S. pyogenes*, and especially adhesions involved in interspecies coaggregation.

To comply with appropriate written description and enablement requirements and to provide sufficient guidance in how one of skill in the art can make and use the various and numerous embodiments of the present invention, incorporated herein in their entireties are the following, generally directed to *S. pyogenes*: U.S. Pat. No. 5,583,765 to Stolle et. al.; U.S. Pat. No. 5,585,098 to Coleman; U.S. Pat. No. 9,056,912 to Grandi; U.S. Pat. No. 9,131,884 to Holmes; US Pat. Publication No. 2014/0065218 to Lang et. al; PCT/US2007/023166 to Mitteness; 2015/0224072 to Pellikaan; U.S. Pat. No. 9,095,704 to McGuire; 2015/0290026 to Kovarik; U.S. Pat. No. 6,552,024 to Chen; 2003/015656 to Jackson et. al.; and 2005/0260544 to Jones et. al.

Various embodiments of the present invention relate to an improved method and system of inhibiting adherence, and thus promoting desorption of *S. pyogenes* to soft tissue surfaces, such as the pharyngeal and oral mucosa of a human, by treating these areas with one or more of the embodiments described herein directed to a mucoadhesive strip. Particular embodiments are directed to oral strips having a surface topography that resists bioadhesion of undesired bacteria that are typically present in a human's mouth. The strips preferably have a surface that is anti-microbial in nature, such that such strips assist in reducing the surface area in the mouth where noxious odors may arise due to the proliferation of foul smelling agents produced by bacteria that can survive in one's mouth.

Thus, one aspect of the present invention is directed to the novel combination of a specifically surface structured bioadhesively attachable, and in a preferred embodiment, dissolvable, strip of material that persists in the mouth for at least one hour and preferably at least about 3 hours, so as to reside on the tissue of the throat where *S. pyogenes* would otherwise reside, specifically the soft palate and thus reduce the occurrence of sore throat. The ability to defeat the proliferation of bacteria, including but not limited to *S. pyogenes*, in a person's mouth can significantly decrease the occurrence of so-called "morning breath".

Certain embodiments entail the use of a specially textured surface, either one both or at least the outer side of an adhesive strip (the side facing away from the mucosal tissue to which it is attached) that has anti-microbial characteristics. In one such embodiment, the surface topography is such that it resists bioadhesion of undesired bacteria that are typically present in a human's mouth. Such a surface may comprise a layer or coating that comprises a pattern defined by a plurality of spaced apart features attached to or projected into a base surface, with a plurality of features each having at least one microscale dimension and having at least one neighboring feature having a substantially different geometry, and having an average spacing between adjacent ones of said features of between 0.5 and 5 .mu.m. Incorporated herein by this reference is U.S. Pat. No. 7,650,848 to address written description and enablement issues regarding the use of suitable textures and surfaces that may be employed. Thus, preferred embodiments include strips that have a surface upon which bacteria do not like to grow, in particular, surfaces having a surface texture and/or pattern that faces away from the mucosal contacting side of the strip and that reduces the number of bacteria that would normally occupy such surface area of the mucosal membrane where the patch/strip no adhered thereto, creates a surface upon which bacteria do not like to grow. Exemplary surfaces that can be employed for such purpose include those in FIG. 2(a-d).

Certain embodiments of the patch (or strip as alternatively referred to herein) have overall geometries particularly suited for the individual's mouth and are customizable therefore. As such, perforated tear lines such that smaller sizes can be fashioned easily. Other geometries of strips are such that they limit common "gag reflexes" of a person. Particular strips are designed so as to also extend over not only a majority of the soft palate region, but also over the hard palate, so as to further reduce the incidence of gag reflexes being triggered. Certain embodiments have toxic substances associated with the surface of the strips, thereby killing certain undesired bacteria in the mouth.

Certain other embodiments comprise bioluminescent strips to facilitate a user's ability to view (in a mirror) the correct placement of the strips in one's throat. The provision of light energy in the oral cavity also has other benefits, as described herein. Bioluminescence is a type of chemiluminescence and in certain embodiments, a catalytic protein increases the efficiency of chemiluminescent reaction such that a bioluminescent protein is determined by detecting the presence of luminescence. Bioluminescent compounds that may be employed in the present invention embodiments include luciferin, luciferase and aequorin. Other embodiments employ differences in visual appearance to determine whether a patch is placed properly; whether certain desired or undesired bacteria are present in the mouth, etc., and such effective means for determining the same include a film, coating or patch that includes one or more of the following characteristics: reflectance, retroreflectance, fluorescence, photoluminescent light transmission, color, tinting strength, and whiteness. Certain embodiments also assist in the detection of whether a person has a certain medical condition, such as strep throat. Thus, in one embodiment, the patch changes color, expresses bioluminescence, etc. if there is strep bacteria present in a predetermined amount. Incorporated herein by this reference for written description purposes in this regard is U.S. Pat. Publication No. 20110250626 to Williams, et al.

Certain other embodiments include strips with compounds residing thereon to facilitate the growth of desired bacteria, such as those deemed beneficial or at least not detrimental to a person's health. For example, certain embodiments are directed to the ability to load or impregnate mucosal strips with any number of active agents to achieve other desirable aspects, such as breath freshening; administration of particular vitamins, medicinal components, salving of mouth sores, short or long term medication through buccal and mucosal tissues, but especially provision of certain bacterial species as set forth herein, and preferably modified bacteria, via CRISPR systems or otherwise, such as *S. pyogenes*, or LAB as described herein, to lessen the chances of a sore throat infection.

The particular dimensions, thickness, size, area surface texture, flexibility, adhesive characteristics, flavoring and taste, composition (e.g. in terms of medicine, vitamins, nutraceuticals, etc.) for a particular strip can be adjusted as one of skill in the art will appreciate. In one embodiment, and unlike most presently available breath strips (e.g. such as Listerine breath strips) the strips employed in the present invention are both thicker, so as to provide more structural integrity to soft palate tissues upon which such strips adhere, and also have more long term (from at least about 5 minutes to several hours), preferably for at least about 3 hours, more preferably at least about 5 hours and most preferably at least about 6 or more hours—roughly equating to the period of time of a person's sleep Moreover, in preferred embodiments the mucosal strips are designed to adhere well with each other when placed on palate tissue so that layering of the strips can be accomplished so as to custom build a desired thickness of the strips over tissue to be covered.

The area of tissue to be covered can be addressed by either having the person provide strips side-by-side to cover the area; by having certain tissue areas provided with thicker ultimate strip depth than other areas (e.g. providing for the option of stiffening certain palate soft tissue more than directly adjacent tissue), and even providing strips having different characteristics in terms of a variety of factors, such as taste, composition, adherence or dissolvability characteristics, area, shape, thickness, flavor, duration of flexibility characteristics, etc. In some embodiments, films of desired thickness and having desired properties in terms of dissolving rate, flexibility, provision of stiffness over time, adhesion duration, ability to cause reversible contraction of soft palate tissue.

While in some embodiments standard sized strips of material may be available such that a person can layer, place side-by-side, orient distinctly, etc. strips of appropriately selected strips, on other embodiments, custom strips or films having particular shapes, such as one that covers the particular area of that particular person's soft palate tissue region, is contemplated. As disclosed herein below, strips are referred alternatively to oral films, mucosal films, etc.

Oral films having desired duration of adhesion and freedom from an adverse feeling in the oral cavity on use are selected that adhere to the particular regions of a person's soft palate. Reference herein to a strip is to any soluble prolonged release presentation of the composition which is conformable and is adapted to lie in a subject's mouth without causing obstruction or interfering with breathing, talking or swallowing or the like, or to conform to the surface of a subjects open skin or wound. Preferably the strip comprises a flexible film or the like. In use, the strip to be placed in a subject's mouth is intended to be placed at the back of the throat. Preferably the strip (or strips, whether layered, certain portions more dissolvable than others, etc.) are positioned on a person's soft palate. This can be achieved via a person's fingers or through the use of an applicator (otherwise described and illustrated.) The strip is particularly suited to delivery of ingredients by delivery to the mucosa of the throat, in particular at the soft tissue in the pharyngeal region of the back of the throat, to keep the pharyngeal membranes moist and lubricated.

The strip is conformed as a relatively thin planar structure to facilitate desired rates of inter-oral dissolution. For example, in certain embodiments, a single strip may be preferably no more than about 150 micron thick, more preferably in the range 100-400 micron thick, and in other embodiments may be over 500 microns in thickness. In other embodiments, however, the ability to layer strips on top of one another provides for the manufacture and availability of strips of more traditional thickness, such as those for example of the breath strips of Listerine, etc. The strip may be of any suitable shape, for example being square or rectangular for ease of storage, placement, distribution in packages, but is preferably generally planar and approximately 0.5 to 2 cm in length and breadth.

In certain embodiments, the strip is manufactured from a material which is soluble within the subject's mouth under the action of saliva and oral enzymes, or under the action of tissue fluids. In other embodiments, however, the strip is made so as not to dissolve and thus, is repeatedly applied to a person's soft palate.

A reusable device that adds the requisite structure to the particular soft palate tissue can have appropriate adhesive integral or added as needed to remain in a desired position. The customization of such a strip in terms of shape, size, characteristics regarding flavor, thickness, adhesive qualities etc. are within the present scope of the invention.

In certain embodiments, the base material for the strip is any suitable soluble solid material, which term includes gel-like and other materials which are sufficiently solid to enable the strip to be conformed to its desired shape. In particular, a carrier or base material of the strip may comprise a soluble gel material, and is for example based upon on an organic gel, which could for example be a fish, animal, bovine or marine gelatin or vegetal gelatin-like product, a polysaccharide, a cellulosic material, pectin such as from fruits, or other suitable base. Other materials may be added to the base gel, for example to stabilize, add other effects flavor etc. The carrier or soluble base material may be inert, or may itself have an activity or other desired property, whether in relation to the primary purpose of the invention or otherwise.

Active agents may be used either impregnated in the strip material, added later, layered in a fashion so that an adhesive strip is separate from an active layer strip; the provision of strips that can encompass or otherwise carry one or more active ingredient strips, liquids, etc. in a pouch or encapsulation such that administration of various active ingredients can be achieved via attachment of an active ingredient container to the soft palate adhesive strip. Time release and slow release aspects of delivery can be achieved via suitable selection of permeable barriers employed to contain active ingredients and then the association of such barriers to soft palate adhesive strips. The layering of strip for separate and distinct purposes of structural tissue support versus for administering active ingredients is an entire segment of different embodiments of the present invention.

Components that can be included in strips or associated with strips in the various ways described herein include agents that may include additional active ingredients, including a plurality of active ingredients having an activity in relation to a particular condition or the throat or throat disorder, oral conditions, open skin or wound healing or repair agents and/or active ingredients having other desired activity.

Preferably in certain embodiments, active ingredients include at least one active ingredient with physical (moisturizing, lubricating, cooling etc.) or pharmacological (for example decongestant, anti-histamine, anti-bacterial, anti-inflammatory, analgesic etc.) activity. For example, active ingredients might include ingredients having any desired physical or pharmacological activity on the mucous membranes of the throat, including without limitation decongestants, lubricants, antibacterial and antiseptic compositions, anti-histamines, anti-inflammatory compositions, analgesics, and other medicaments and non-medicaments. Additional ingredients may include breath-fresheners and deodorizers. Inactive ingredients may be added in suspension or solution for example to stabilize or preserve the soluble base, balance the pH of the base, bring the base to closer approximation to isotonic concentration etc. The composition may additionally include adjuvants and the like such as vitamins for example selected from Ascorbic acid (vitamin C) which enhance the active ingredient effect. The composition may include additional ingredients for formulation purposes, for example selected from sodium chloride which maintains favorable isotonicity.

In still other embodiments, the use of additional ingredients may provide for chemical binding, and for example for the use of liposome technology, can be employed. In some embodiments of the invention a part or all of the active ingredients are encapsulated within encapsulation structures selected to provide the desired degree of adhesion to the mucous membranes of the throat, and adapted to release the active ingredients slowly over time in situ. These encapsulation structures may be distributed within the base material in the strip composition. In one embodiment, the encapsulation structures comprise multilamellar microparticles. The multilamellar microparticles are selected to exhibit good adhesion to the mucous membranes of the throat, and are small enough to be effectively distributed in the strip. The multiple layers may be structured to give slow release of the active ingredient over the desired time period, so that a single strip dose gives sustained activity over time, for example providing for measurable activity for a sustained period of four or more hours, and ideally of for example 6 to 12 hours, to give overnight effectiveness.

Microparticles are preferably sized and shaped to form an effective distribution within the base material in the strip as a composition in accordance with the invention. The microparticles in particular comprise generally spherical particles or microspheres. Particle sizes in the range 0.1 to 50 .mu.m, and for example 1 to 20 .mu.m are likely to be preferred. Particle levels of 5-25% within the composition are preferred but depend on the particular tissue characteristics being addressed.

Microparticles may be are adapted to facilitate slow release of the active ingredients over time, and are preferably inherently able to show good adhesion to the mucous membranes of the throat. Active ingredients are thus stabilized in situ on the mucous membranes at the back of the throat, and then released steadily at the site where they are required.

Using the present invention, it becomes possible to maintain reasonable levels of activity over the sort of time scale necessary to be effective overnight, and for example to assist in providing a relatively less disturbed night's sleep. Microparticles comprise multiple layered structures formulated with one or more of: surfactant layers (comprising any type of surfactant such as anionic, non-anionic, cationic, phospholipids and the like such as sucroesters and guar hydroxypropyltrimonium chloride), and hydrophobic or lipophilic materials such as aliphatic and aromatic hydrocarbons, optionally halogenated, higher alcohols, ketones and the like, for example including Vitamins (A, E, D), carotenoides, polyphenols, vegetable oils, essential oils, phytosterols, lipophilic preservatives, menthol, linalool, eucalyptol, and the like; and polar layers including solvents or polar media such as water, glycerol, PEG, sorbitol, glycol, hydrophilic materials such as alcohols or ethoxylated alcohols, carboxylic acids or salt of a fatty acid, quaternary ammonium derivatives, sulphonates or sulphates and the like, vitamins (B, C), flavonoides, 18-beta glycyrrhetinic acid and derivatives, glycerol, active ingredients such as plant extract as hereinbefore defined; hydrophilic preservative; cellulose polymer, hyaluronic acid and derivatives, alpha-hydroxide acid, and the like. Also possible inclusion are pectin; cellulose; sodium hyaluronate; guar hydroxypropyltrimonium chloride; polysorbate 60, and optionally additionally cellulose; xanthan gum; chitosan or quaternary ammonium. In one embodiment, such strip composition comprises: solvent 30-60%, Humectant 8-14%, Texturant 0-2%, Preservative 0-2%, and an Acidity regulator 0-1% (all by weight). Microparticles thus preferably comprise multilamellar structures of surfactant layers, which are able to encapsulate active ingredients to a very high degree for protection and controlled release—whether that be rapid release (e.g. for certain tissue stiffening components) or longer term release, such as breath freshing components). The strips are formulated to be adapted to enhance adhesion to human skin, and hence to fix the particles in position on the mucous membranes of the throat. Suitable compositions include 30 to 50% surfactant, 30 to 50% polar medium, and 10 to 60% active binding agent, comprising hydrophilic and hydrophobic agents as appropriate.

With respect to manufacturing of strips, one of skill in the art will appreciate the various methods and components involved to achieve desired qualitative and quantitative aspects. While the present specification provides some detail as to how to make and use certain embodiments of the present invention, reliance on incorporation by reference is appropriate to encompass the myriad of ways in which a particular product is produced.

Preferably the strips of the present invention are made in a manner that do not dissolve in fewer than ten seconds, thus distinguishing the same from common breath strips widely available. The strips of the present invention may have a weight of from 30 to several hundred mg., preferably over 33 mg. Preferably, strips of the present invention have sufficiently high moisture content to impart the product with flexibility and to avoid becoming brittle, e.g. the strips should preferably avoid cracking when bent.

The strips may comprise a hydrocolloid of any suitable type, amount and number of hydrocolloids. In an embodiment, the hydrocolloid can constitute between about 10% to about 50% by dry weight of the edible film, preferably about 20% to about 30% by dry weight. The hydrocolloid can be derived from, for example, natural seaweeds, natural seed gum, natural plant exudates, natural fiber extracts, biosynthetic gums, gelatins, biosynthetic process starch or cellulosic materials, alginates, sodium alginate, calcium alginate, carrageenans, guar gum, locust gum, tara gum, gum arabic, ghatti gum, agar gum, xanthan gum, pectin, other like hydrocolloid source material or combinations thereof.

Incorporated herein by this reference is 2011/0009834 to Asmussen with respect to various particular components that can be utilized to form strips.

In one embodiment, the strip has a surface adapted to promote tissue in-growth, and in other embodiments, the growth of desired bacteria, especially those bacteria modified as described herein, such as via a CRISPR-Cas system. The in-growth promoting surface is desirably selected from a group of outer surfaces including a textured surface, a porous surface, a braided surface, a mesh surface, a fleece surface, and a coating for inducing bone or tissue in-growth.

Various embodiments are directed to a buccal bioadhesive strip, that when applied to the soft palate, has a surface that is anti-microbial in nature, preferably one that *S. pyogenes* cannot readily adhere to, such that such strips assist in reducing the surface area in the mouth where *S. pyogenes* can exist and grow. Such strips also have the attribute of preventing noxious odors that may arise due to the proliferation of foul smelling agents produced by bacteria that can survive in one's mouth.

Other embodiments are directed to a buccal bioadhesive strip adapted to be attached to the tissue of the soft palate, such strip including at least one surface that has a pattern defined by a plurality of spaced apart features each having at least one microscale dimension and having at least one neighboring feature having a substantially different geometry, wherein an average spacing between adjacent ones of said features is between 0.5 and 5 .mu.m.

Preferably, the strip has a first and second side, the first side having a bioadhesive that is adapted to bind to a mucosal membrane for at least 1 hour while inside a person's mouth, wherein the strip extends over a majority of the soft palate. In certain embodiments, the strip includes xylitol and at least one encapsulated pocket containing one of an analgesic, a solution containing a LAB, selected from the group consisting of a LAB that coaggregate with *S. pyogenes*. Preferably the strip reduces the adhesion of *S. pyogenes* to the epithelial tissue of a person's mouth and also includes between 0.2 and 0.9% xylitol by weight. Certain strips are made with bioluminescent material and/or material that reacts specifically with ultraviolet light to kill bacteria on the strip. Projection of UV light onto the strip to destroy bacteria after a certain amount of time is one aspect of the present invention. While the strip may be non-dissolvable in a person's mouth, preferably it is dissolvable in a person's mouth within a period of 3 hours.

In certain embodiments, a mucosal adhesive strip has a coated surface for resisting bioadhesion that includes at least one patterned polymer including coating layer having a plurality of features attached to or projected into a base surface. The features each have at least one microscale (<1 mm) dimension and have at least one neighboring feature having a substantially different geometry. The patterned coating layer preferably provides an average roughness factor (R) of from 4 to 50. The coating layer resists or enhances bioadhesion as compared to the base surface. An article having a surface coating with topography for controlling bioadhesion comprises a base surface, at least one patterned polymer comprising coating layer including a plurality of spaced apart features attached to or projected into the base surface which provide at least a first feature spacing distance. The features each have at least one microscale dimension and at least one neighboring feature having a substantially different geometry. The coating layer provides an average roughness factor (R) of from 2 to 50, preferably being from 4 to 50. The coating layer resists or enhances bioadhesion as compared to the base surface.

Still other embodiments include the use of bacteria that have been modified to remove or disable one or more virulence factors of the particular bacteria. Key virulence factors present in GAS include streptococcal pyrogenic exotoxin (SPE)-B, the hyaluronan synthesis operon and active superantigen against human immune cells. A key event in the ability of GAS to cause severe invasive streptococcal infection is the acquisition of novel genetic traits. During severe invasive infection, however, GAS destroys its own covRS (for "control of virulence genes") two-component system, which negatively regulates many virulence factor genes, resulting in a hyper-virulent phenotype. Modification of GAS, preferably using CRISPR-Cas and Cpl1, can address such virulent strains and thus control the infections.

These modified bacteria, especially those that demonstrate human specificity, are used to competitively inhibit or to otherwise populate tissue surfaces, such as the oral cavity, to prevent a variety of diseases. In this regard, one aspect of the present invention is directed to the modification of certain human-specific pathogens by targeting one or more virulence factors thereof, preferably by using CRISPR-Cas or CRISPR-Cpl1 systems, to excise virulence factors genes, or at least portions thereof or transcriptional or translational controls therefore, such that such pathogenic pathogens are deprived of their undesired pathogenic characteristics. One of skill in the art can readily assess the number and identity of human-specific pathogens, as well as the particular virulence factors associated therewith, and can then, employing the CRISPR systems as referenced herein, remove, render incapable or otherwise disable the virulence facts of such microorganisms such that they no long pose a pathogenic threat to humans. In various aspects of the present invention, there is a purposeful exposure of individuals to such modified pathogens such that the population of the same, for example in the oral cavity or the human gut, competitively inhibits the infection of non-modified pathogenic microbes of the same species. In one particular embodiment, *S. pyogenes* is modified to render ineffective one or more virulence facts such that the progression of a sore throat is avoided.

The concerns relating to possible unintended consequences from the genetic modification of genomes, especially the human genome, are largely if not entirely addressed in various embodiments of the present invention as modifications are not being made to the human genome—but rather to microbes. Moreover, in preferred embodiments, the microbes modified are limited to those demonstrating human tropism such that undesired and unintended changes to other animals and organisms are not affected and that the only implications of such genomic alterations of human specific pathogens are restricted to such species in a manner that is not capable of affecting other than the particular human disease at issue. This can include, for example, modifications and/or employment of integrons, which are a two-component genetic recombination system present in the chromosome of many bacterial species. The integron incorporates mobile genes termed gene cassettes into a reserved genetic site via site-specific recombination, named the Integron/gene cassette system. The integron consists of three basic elements: an integrase gene, an attachment site and a promoter. These elements can be manipulated to, for example, decrease the ability of a dominant *S. pyogenes* population in one's mouth from being able to effectively attach to epithelial tissue; or alternatively, to coaggregate with other bacteria so as to be swalled and removed from the oral cavity, etc.

Certain other embodiments of the present invention are directed to reducing the likelihood of a subject suffering neurologic conditions and diseases. One aspect to the mystery of Alzheimer's disease etiopathogenesis lies in the relative absence of Alzheimer's disease in certain Amish communities. The prevalence of *Prevotella* in the oral cavity of the Amish, the production of nitric oxide by this bacteria, and the reduction of spirochetes in the brains of the Amish, all present evidence as to an effective avenue for therapeutic intervention in Alzheimer's disease prevention and/or progression. The insights gained from an evaluation of the Amish, especially with respect to the oral microbiome they possess and the absence of various diseases they suffer from, is one of the foundational aspects of various embodiments of the present invention.

While not bound by theory, *Prevotella* in an individual's oral cavity, due to its production of nitric oxide, plays a beneficial role in maintaining oral health in a fashion that prevents AD progression. While *Prevotella* is also seen in biofilms that may ultimately also be involved in providing conditions for spirochetes to be protected and grow, and ultimately to be released into the blood or along nerves to reach the brain, the presence of *Prevotella* should not automatically be considered as a negative. The conventional thinking that various of the bacteria found in one's oral microbiome are clearly categorized as either "good" or "bad" is outdated and largely inaccurate. Depending upon other conditions, the presence of particular bacteria previously deemed to be pathogenic, may indeed serve a beneficial role in maintaining a person's oral microbiome health, including in establishing a better oral microbiome to prevent the progression of AD.

Nitric oxide (NO) is known to have potent antimicrobial properties and is an important cellular signaling molecule. NO is a free radical with an unpaired electron. Although the earliest studies in the field suggested that NO is a strictly pro-inflammatory macrophage product, it is clear from the current literature that, in fact, NO is made by numerous cell types and is often anti-inflammatory. Much of this dichotomy can be explained by the particular responses of given cells involved in the inflammatory response, but another variable involves the complex chemistry in which NO can participate.

Nitric oxide is a ubiquitous intercellular messenger molecule with important cardiovascular, neurological, and immune functions. Nitric oxide is a short-lived, reactive free radical that participates in a variety of reactions and in small controlled concentrations in the body, it acts as a physiological and pathophysiological mediator and it plays an important role in biological systems. The assessment of the stable end products of NO, nitrite and nitrate (NOx), is commonly used as a measure of the NO production in biological fluids. The production of nitric oxide represents a mechanism of pathogen destruction in activated neutrophils. Production of NO or expression of inducible NO synthase (iNOS) by peripheral neutrophils or in gingival tissues is associated with periodontal disease. The massive presence of neutrophils and their enhanced activity at sites of periodontal disease have sparked debate as to whether neutrophils are responsible for the destruction of periodontal tissues or whether they play protective roles in controlling pathogenic bacteria involved in periodontal disease. Neutrophils from periodontitis patients produced significantly lower levels of NO levels when compared to neutrophils from healthy subjects. Low NO levels were produced by neutrophils from chronic periodontitis patients. So the presence of NO seems to be desired in avoiding periodontitis. *Prevotella* is associated with increased NO production and thus, *Prevotella*—while also associated with periodontitis, is oddly believed to be beneficial to individuals. The recruitment of neutrophils and other leukocytes in the periodontal pocket is an important feature of the inflammatory process in periodontal disease. Neutrophils play an important role in periodontitis by producing nitric oxide (NO) and antimicrobial peptides, molecules with microbicidal activity via oxygen-dependent and -independent mechanisms, respectively. The use of nitric oxide to disperse biofilms may be employed to improve infectious disease treatments. The use of low levels of NO to exploit its signaling properties to induce dispersal represents an unprecedented and promising strategy for the control of biofilms in clinical contexts.

In recent years, nitric oxide (NO) has emerged as a major mediator of inflammation. As might be expected from such a pleiotropic molecule, there are contradictory reports in the literature concerning its role as an anti-inflammatory or proinflammatory agent. The inconsistencies reported probably are due to the multiple cellular actions of this molecule, the level and site of NO production, and the redox milieu into which it is released. Chronic inflammation is characterized by a proliferation of fibroblasts and formation of blood vessels (angiogenesis), as well as an influx of chronic inflammatory cells, namely granulocytes (neutrophils, eosinophils, and basophils), lymphocytes, plasma cells and macrophages. Nearly two decades ago, the production of nitrogen oxides was associated with inflammation. The metabolic pathway known as the Larginine: NO pathway is the main source for the production of NO in mammalian cells by a group of enzymes known as the nitric oxide synthases (NOS). The enzyme primarily responsible for the roles of NO in inflammatory processes is the inducible NOS (iNOS; NOS2; or type II NOS), which is not typically expressed in resting cells and must first be induced by certain cytokines or microbial products.

The dichotomous role of NO in inflammation, often referred to as the NO paradox, is based mainly on the conflicting data showing the effects of NOS inhibitors of varying selectivity in different animal models. The physiological and pathological functions of NO are diverse and often contradictory. NO acts as a useful endogenous free-radical scavenger. NO may provide a chemical barrier to cytotoxic free radicals. NO may have a considerable protective effect on cellular viability and can act as an antioxidant protecting cells from oxidant-induced damage and preventing endothelial apoptosis. Low NO concentrations contribute to endothelial cell survival and high NO levels induce the apoptosis of endothelial cell. Any assessment of the role of NO in human disease must take into account the dual role of NO.

The biological nitrogen cycle involves step-wise reduction of nitrogen oxides to ammonium salts and oxidation of ammonia back to nitrites and nitrates by plants and bacteria. The salivary bacterial reduction of nitrate to nitrite has been recognized as an important metabolic conversion in humans. Several enteric bacteria have also shown the ability of catalytic reduction of nitrate to ammonia via nitrite during dissimilatory respiration. Although to date the importance of this pathway in bacterial species colonizing the human intestine has been little studied, the present inventors submit that it is a major factor involved in the occurrence of migraines.

In addition to the connection between the gut microbiome and migraines, there is also believed to be a connection with the oral microbiome of an individual with various health conditions, including an association with dysbiosis of the oral microbiome and migraines.

Many biochemical, pharmacological, neuropathological, and experimental data suggest a role of nitric oxide in the pathogenesis of migraine. Nitric oxide (NO) is a very important molecule in the regulation of cerebral and extra cerebral cranial blood flow and arterial diameters. It is also involved in nociceptive processing. Glyceryl trinitrate (GTN), a pro-drug for NO, causes headache in normal volunteers and a so called delayed headache that fulfils criteria for migraine without aura in migraine sufferers. One aspect of the present invention is to prevent migraines via the inhibition of NO production; the blockade of steps in the NO-cGMP pathway; or the scavenging of NO. The pain signaling molecules, nitric oxide synthase (NOS) and calcitonin gene-related peptide (CGRP) are implicated in the pathophysiology of migraines.

Non-specific NOS inhibition and a specific neuronal NOS inhibitor have been found to attenuate neurogenic dural vasodilation. Interestingly, specific inducible and endothelial NOS inhibitors had no effect. Non-vascular inducible NOS inhibitors have been shown unable to abort or prevent migraine. The present inventors submit that this leaves neuronal NOS inhibition and bacterial NOS inhibition (bNOS) as candidates for therapy, with the latter being considered the primary causative agents in preventing migraines. Neurons in the trigeminocervical complex are the major relay neurons and are the neural substrates of head pain. NO production in the TCC and potentially other areas of the brain may be involved in triggering migraines, and therefore blocking NO production is believed to be therapeutic.

The nitric oxide synthase inhibitor NG-monomethyi-L-arginine (L-NMMA) may be employed in several embodiments of the present invention. Blockade of nitric oxide synthases (NOS) by L-NMMA effectively treats attacks of migraine without aura. Similar results have been obtained for chronic tension-type headache and cluster headache.

Inhibition of the breakdown of cGMP also provokes migraine in sufferers, indicating that cGMP is the effector of NO-induced migraine. Several relationships exist between NO, calcitonin gene-related peptide and other molecules important in migraine. Also, ion channels, particularly the K(ATP) channels, are important for the action of NO.

NO donors and their ability to trigger migraine in patients is well known and so nitric oxide synthase (NOS) inhibitors have been explored for the treatment of migraine. While NO donors are known to cause vasodilation, they also cause activation of neurons in the trigeminocervical complex of the brain that are not vascular related, as well as other areas of the brain related to migraine. Thus, the present inventors submit that non-vascular mechanisms are involved and that non-vascular NOS inhibitors are efficacious in the treatment of migraines.

Nitric oxide synthases (NOSs) are multidomain metalloproteins first identified in mammals as being responsible for the synthesis of the wide-spread signaling and protective agent nitric oxide (NO). Nitric oxide synthases are heme-based monooxygenases that oxidize L-arginine to nitric oxide (NO), a signaling molecule and cytotoxic agent in higher organisms. NO is one of the main inflammatory mediators involved in both inflammation and angiogenesis. NO can be synthesized by three different isoforms of NO synthase: neuronal (nNOS), endothelial (eNOS), and inducible (iNOS) synthases. NO production due to cytokine-induced expression of inducible nitric oxide synthase (iNOS) is largely involved in the pathophysiology of inflammation.

Although NOS-like activity has been reported in many bacteria, only a few bacterial homologs of mammalian NOSs (mNOSs) have been characterized to date. Nitric oxide synthases (NOSs) play an essential role in synthesizing nitric oxide (NO) by oxidizing I-arginine. arginine. NO is a significant mediator in cellular signaling pathways. It serves as a crucial regulator in insulin secretion, vascular tone, peristalsis, angiogenesis, neural development and inflammation. Due to its important role, the inhibition of these vital enzymes provides therapeutic applications that target NOSs.

In contrast to mNOSs, which possess both a catalytic and a reductase domain, bacterial enzymes lack reductase domains and require the supply of suitable reductants to produce NO. A notable exception is a NOS from certain gram-negative bacteria that contain a new type of reductase module. Bacterial NOSs seem to have functions that differ from those of mNOSs, including nitration of different metabolites and protection against oxidative stress. Bacterial NOSs provide a better understanding of the mechanism of NO synthesis and unveil a variety of new functions for NO in microbes.

In one embodiment, the lactic acid bacterium *Lactobacillus reuteri* is employed as it is believed that by doing so, one is able to induce oxytocin, preferably in a manner that offers a sustained induction of oxytocin, unlike the short effects achieved using intranasal oxytocin sprays, etc. Thus, one aspect of the present invention relates to the employment of probiotics-induced oxytocin to reduce migraine symptoms, especially in the form of an oral adhesive strip as further described herein.

One aspect of the present invention is directed to addressing the causative agents involved in migraines and dizziness, instead of merely addressing the symptoms thereof. As can be seen from the prior art as discussed herein, the diagnosis and treatment of both migraines and dizziness have continued to be directed to symptoms, rather than to an underlying treatable cause. The present invention changes that focus and thus, provides both an understanding of causative agents and how best to treat individuals so that their maladies are addressed. The present inventors believe that there is an association between the occurrence of migraines and gastrointestinal (GI) disorders, including irritable bowel syndrome (IBS). People who regularly experience GI symptoms have a higher prevalence of headaches, with a stronger association with increasing headache frequency.

While not bound by theory, it is believed that the gut microbiota is an independent factor that contributes to systemic diseases, often involving the migration of stimulated immune cells, by systemic diffusion of microbial products or metabolites, or by bacterial translocation as a result of decreased intestinal barrier function. The brain and the GI tract are strongly connected via neural, endocrine, and immune pathways. The gut microbiota, as well as the oral microbiota, is associated with brain functions and neurological diseases like migraine.

Empirical data exists to reveal the association of migraines with disruptions of a person's microbiome. For example, children with a mother with a history of migraine are more likely to have infantile colic. Children with migraine are more likely to have experienced infantile colic compared to controls. Several studies demonstrated significant associations between migraine and celiac disease, inflammatory bowel disease, and IBS.

It is believed that the underlying mechanisms of migraine and GI diseases are both related to increased gut permeability and inflammation. In addition, it is believed that a person's oral microbiome is also responsible for migraines. Thus in several embodiments of the present invention, modification of the oral as well as (or solely) the gut microbiome is achieved to combat and address migraine occurrences.

The biological nitrogen cycle involves step-wise reduction of nitrogen oxides to ammonium salts and oxidation of ammonia back to nitrites and nitrates by plants and bacteria. The salivary bacterial reduction of nitrate to nitrite has been recognized as an important metabolic conversion in humans. Several enteric bacteria have also shown the ability of catalytic reduction of nitrate to ammonia via nitrite during dissimilatory respiration. Although to date the importance of this pathway in bacterial species colonizing the human intestine has been little studied, the present inventors submit that it is a major factor involved in the occurrence of migraines.

In addition to the connection between the gut microbiome and migraines, there is also believed to be a connection with the oral microbiome of an individual with various health conditions, including an association with dysbiosis of the oral microbiome and migraines.

Many biochemical, pharmacological, neuropathological, and experimental data suggest a role of nitric oxide in the pathogenesis of migraine. Nitric oxide (NO) is a very important molecule in the regulation of cerebral and extra cerebral cranial blood flow and arterial diameters. It is also involved in nociceptive processing. Glyceryl trinitrate (GTN), a pro-drug for NO, causes headache in normal volunteers and a so called delayed headache that fulfils criteria for migraine without aura in migraine sufferers. One aspect of the present invention is to prevent migraines via the inhibition of NO production; the blockade of steps in the NO-cGMP pathway; or the scavenging of NO. The pain signaling molecules, nitric oxide synthase (NOS) and calcitonin gene-related peptide (CGRP) are implicated in the pathophysiology of migraines.

Non-specific NOS inhibition and a specific neuronal NOS inhibitor have been found to attenuate neurogenic dural vasodilation. Interestingly, specific inducible and endothelial NOS inhibitors had no effect. Non-vascular inducible NOS inhibitors have been shown unable to abort or prevent migraine. The present inventors submit that this leaves neuronal NOS inhibition and bacterial NOS inhibition (bNOS) as candidates for therapy, with the latter being considered the primary causative agents in preventing migraines. Neurons in the trigeminocervical complex are the major relay neurons and are the neural substrates of head pain. NO production in the TCC and potentially other areas of the brain may be involved in triggering migraines, and therefore blocking NO production is believed to be therapeutic.

The nitric oxide synthase inhibitor NG-monomethyi-L-arginine (L-NMMA) may be employed in several embodiments of the present invention. Blockade of nitric oxide synthases (NOS) by L-NMMA effectively treats attacks of migraine without aura. Similar results have been obtained for chronic tension-type headache and cluster headache.

Inhibition of the breakdown of cGMP also provokes migraine in sufferers, indicating that cGMP is the effector of NO-induced migraine. Several relationships exist between NO, calcitonin gene-related peptide and other molecules important in migraine. Also, ion channels, particularly the K(ATP) channels, are important for the action of NO.

NO donors and their ability to trigger migraine in patients is well known and so nitric oxide synthase (NOS) inhibitors have been explored for the treatment of migraine. While NO donors are known to cause vasodilation, they also cause activation of neurons in the trigeminocervical complex of the brain that are not vascular related, as well as other areas of the brain related to migraine. Thus, the present inventors submit that non-vascular mechanisms are involved and that non-vascular NOS inhibitors are efficacious in the treatment of migraines.

Nitric oxide synthases (NOSs) are multidomain metalloproteins first identified in mammals as being responsible for the synthesis of the wide-spread signaling and protective agent nitric oxide (NO). Nitric oxide synthases are heme-based monooxygenases that oxidize L-arginine to nitric oxide (NO), a signaling molecule and cytotoxic agent in higher organisms. NO is one of the main inflammatory mediators involved in both inflammation and angiogenesis. NO can be synthesized by three different isoforms of NO synthase: neuronal (nNOS), endothelial (eNOS), and inducible (iNOS) synthases. NO production due to cytokine-induced expression of inducible nitric oxide synthase (iNOS) is largely involved in the pathophysiology of inflammation.

Although NOS-like activity has been reported in many bacteria, only a few bacterial homologs of mammalian NOSs (mNOSs) have been characterized to date. Nitric oxide synthases (NOSs) play an essential role in synthesizing nitric oxide (NO) by oxidizing 1-arginine. NO is a significant mediator in cellular signaling pathways. It serves as a crucial regulator in insulin secretion, vascular tone, peristalsis, angiogenesis, neural development and inflammation. Due to its important role, the inhibition of these vital enzymes provides therapeutic applications that target NOSs.

Over the past 10 years, prokaryotic proteins that are homologous to animal NOSs have been identified and characterized, both in terms of enzymology and biological function. In contrast to mNOSs, which possess both a catalytic and a reductase domain, the bacterial enzymes lack reductase domains and require the supply of suitable reductants to produce NO. A notable exception is a NOS from a gram-negative bacterium that contains a new type of reductase module.

Bacterial NOSs seem to have functions that differ from those of mNOSs, including nitration of different metabolites and protection against oxidative stress. Bacterial NOSs provide a better understanding of the mechanism of NO synthesis and unveil a variety of new functions for NO in microbes.

In one embodiment, the lactic acid bacterium *Lactobacillus reuteri* is employed as it is believed that by doing so, one is able to induce oxytocin, preferably in a manner that offers a sustained induction of oxytocin, unlike the short effects achieved using intranasal oxytocin sprays, etc. Thus, one aspect of the present invention relates to the employment of probiotics-induced oxytocin to reduce migraine symptoms, especially in the form of an oral adhesive strip as further described herein.

Other embodiments relate to the employment of calcitonin gene-related peptide (CGRP) as a major player in treating migraines. In various embodiments, CGRP triggers a chain of events such that increased amounts of CGRP released at the start of a migraine sensitize the trigeminal nerve to what are normally innocuous signals, resulting in inflammation in the nerves that is relayed to the brain as a pain signal and in such a manner, stop headaches from outside the central nervous system, believed to be active on the trigeminal connections into the brain rather than the brain itself. It is further believed that there is often a fairly massive change in the permeability of the blood-brain barrier during a migraine attack and may have an effect on certain sections of the brainstem that are not believed to be as well protected by the blood-brain barrier. As is the case with autism, it is believed that a gut brain inter-relationship dysbiosis is caused by a lowered *Lactobacillus* spp. and decreased number of *Clostridium* spp. populations in an individual's gut microbiome. Thus, restoring the gut microbiome with appropriate levels of particular bacteria species as set forth herein is one aspect of the present invention. In addition, in various embodiments, the maintenance of desired populations in the gut is achieved via the employment of fibre that is essential for the fostering of a healthy gut microbiome once established so that the beneficial bacteria have a food source other than the mucosa proteins that protect the tissue of the gut. In preferred embodiments approximately 6 g/fibre/day is administered to an individual as it is believed that by doing so one is able to increase the numbers of bifidobacteria in the gut microbiome and thus, increase desired fermentation by increasing the number and maintenance of both Bifidobacteriaceae and Lactobacteriaceae families. In preferred embodiments, a diet rich in plant polysaccharides (i.e., fiber) is employed to confer protection against various ailments associated with the gut microbiome dysbiosis, including not only migraines, but also cardiovascular disease (CVD). Such benefits are believed to be derived from the interactions between carbohydrates that reach the distal gut and microbes via production of short chain fatty acids (SOFA, e.g., acetate, propionate and butyrate). Thus, in various embodiments, in addition to the administration of beneficial bacteria as described herein wither to the gut or the oral microbiome of an individual (or both) the consumption of a diet high in fibre is employed to increase microbiota populations to generate short chain fatty acids (SCFAs) such as acetate, which has a protective role in inflammatory diseases. Such a diet is further believed to attenuate the development of cardiac fibrosis due to the belief that inflammation is also implicated in cardiac remodeling. Thus, a high fiber diet, especially one that includes increased levels of acetate, is believed to not only reduce the incidences of migraine, but to further result in significantly less cardiac hypertrophy, perivascular and interstitial cardiac fibrosis, and improved cardiac function. It is further believed that the protective effects of high fiber and acetate are accompanied by a decrease in the ratio of bacteria from the phylum Firmicutes compared to Bacteroidetes. In addition to the association of the gut and the brain as it relates to the incidence of migraines, there is also a gut-heart connection and by employing similar efforts to address the dysbiosis of an individuals' gut and oral microbiomes, another aspect of the present invention is directed to addressing and significantly preventing the occurrence of heart disease.

In situations where there is insufficient fiber for the beneficial bacteria to consume, the bacteria end up eroding the mucus of the gut and leads to epithelial access by mucosal pathogens. It is believed that there is an increase in the amount of calcitonin gene-related peptide released at the start of a migraine that sensitizes the trigeminal nerve to what are normally innocuous signals, resulting in inflammation in the nerves that is relayed to the brain as a pain signal. Thus, one aspect of the present invention relates to the ability to affect the trigeminal connections into the brain, rather than the brain itself, and to do so by modifying the type, number and maintenance of desired bacteria in an individual's gut and oral microbiome. In addition to migraine headaches, other aspects of the invention are directed more generally to addressing other pain related conditions, including but not limited to fibromyalgia, cluster headaches, etc.

Therefore, certain embodiments of the present invention are directed to a method of reducing the likelihood of migraine headaches by providing to an individual in need thereof a buccal bioadhesive strip, with such strip having a first and second side and having a surface comprising a pattern defined by a plurality of spaced apart features each having at least one microscale dimension and having at least one neighboring feature having a substantially different geometry. Preferably the average spacing between adjacent ones of such features is between 0.5 and 5 .mu.m.

A bioadhesive is employed that is adapted to bind to a mucosal membrane for at least 1 hour while inside an individual's mouth. Preferably the strip includes xylitol. In other embodiments, the strip includes an encapsulated feature containing a desired bacteria, preferably selected from the group consisting of *Lachnospira, Veillonella, Faecalibacterium* and *Rothia*. Still other embodiments include an antibody on the strip to a calcitonin gene-related peptide. The strip(s) may further include *Lactobacillus* spp. Preferably, methods of the present invention further include administering a diet of at least 6 g/fibre/day to an individual so as to increase the numbers of bifidobacteria in the gut microbiome of the individual. Such a diet should preferably include a high fiber diet that includes acetate, especially in an amount sufficient to decrease the ratio of bacteria in the individual's oral cavity from the phylum Firmicutes compared to Bacteroidetes. It is preferred to increase the number of both Bifidobacteriaceae and Lactobacteriaceae bacteria. Other embodiments increase the population of desired bacteria by including *Enterococcus faecium* on the strip. It is preferred to remove from the oral cavity of the individual gram negative bacteria associated with periodontitis, and within 2 hours thereof, to provide the individual with the strip. Still other embodiments include a strip that includes *Lactobacillus reuteri* bacteria to induce a sustained induction of oxytocin, and providing the individual with an amount of antibiotic sufficient to reduce the number of undesired bacteria in the oral cavity. Prior to the use of the strip, an antibiotic selected from the group consisting of tetracycline hydrochloride, doxycycline, and minocycline is used to reduce the number of undesired bacteria in the oral cavity. One objective is to retard the growth conditions for spirochetes and *P. gingivalis*, believed to be associated with migraine headaches. In still other embodiments, *Veillonella* and/or *Prevotella* bacteria is provided on the strip. As one of skill in the art will appreciate, the strip may be made to include at least one polymer selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. Preferably, the strip includes at least 0.2% xylitol by weight. In certain embodiments, the strip comprises bioluminescent material. Preferably the strip is dissolvable in a person's mouth within a period of 1 hour. In certain preferred embodiments, the strip has least one encapsulated feature that contains an agent selected from the group consisting of an antibiotic; lactic acid bacteria; and xylitol, e.g. at least 200 mg of xylitol. Such a frangible capsule may be constructed so that it may be broken by the individual pressing against said strip with the individual's tongue.

Still other embodiments of the present invention are directed to addressing the incidence of migraines and cluster headaches using bacteria of the oral cavity and gut of an individual. Microbes, among others in the digestive tract, are capable of oxidizing alcohol to acetaldehyde. Compositions containing one or more cysteines as active agents have been shown to bind acetaldehyde. These active agents have been found to also be capable of breaking down biofilms formed by some microbes, particularly in the stomach. One aspect of the present invention is therefore directed to reducing the likelihood of headaches, including not only migraines, but also cluster headaches. Thus, several embodiments employ microbes, preferably particular bacterial species as set forth herein, to assist in decreasing the amount of acetaldehyde in the body of an individual who suffers from such headaches. This can be achieved by employing cysteine generating microbes that are effective in reducing the amount of acetaldehydes. Other microbes are also effective in degrading acetaldehydes.

While migraines are diagnosed more often in women, cluster headaches are more prevalent in men. Cluster headache is a neurological disease that involves, as its most prominent feature, excruciating unilateral headaches of extreme intensity. "Cluster" refers to the tendency of these headaches to occur periodically, with active periods interrupted by spontaneous remissions. The cause of the disease is currently unknown. Cluster headaches are sometimes classified as vascular headaches. The intense pain has been suggested to be linked with the dilation of blood vessels which creates pressure on the trigeminal nerve. Cluster headache episodes are known to be triggered by factors, such as alcohol consumption. Patients who are sensitive to alcohol note that attacks are triggered within 5 to 45 minutes after the ingestion of modest amounts of alcohol, usually being less than a single cocktail or glass of wine. Alcohol triggers attacks in 70 to 80% of exposures. Microbial metabolism may contribute to the toxicity of alcohol, especially in the gastrointestinal tract, where aerobic and facultative anaerobic bacteria convert ethanol to acetaldehyde. Indeed, acetaldehyde is known to be a highly toxic and pro-carcinogenic compound with various negative effects, ranging from DNA damage and impaired DNA excision repair to the degradation of folate. Thus, one aspect of various embodiments of the present invention is directed to providing particular bacteria to a person who consumes alcohol in a manner that such bacteria may ameliorate the accumulation of acetaldehyde. In certain embodiments, bacteria are employed to degrade acetaldehyde, such bacteria preferably having an aldehyde dehydrogenase, such as bacteria of the genus *Saccharomyces* and/or a threonine aldolase derived from *Escherichia coli*. Employment of CRISPR-Cas systems to incorporate the genes of such bacteria into other bacteria as set forth herein forms various other embodiments of the present invention. Thus, use of bacteria in the oral cavity, as well as in the gut microbiome of an individual, are employed to degrade acetaldehyde and thus reduce the incidence of migraines and cluster headaches. While many of the embodiments described herein are principally directed to a method and system for addressing the terrible pain occasioned by headaches caused by migraines and cluster headaches, one may further appreciate other aspects of the invention as being directed to hangover remedies as the ability to degrade alcohol and acetaldehyde to remedy the effects of consuming too much alcohol: thus introducing "Hangover Strips" in addition to Headache Strips as described herein.

In certain embodiments, the present invention is directed to the use of light inside the oral cavity to modify bacterial populations in a beneficial way to treat various conditions and diseases without the problems associated with antibiotic use. Certain embodiments of the present invention are directed to the use of light in the oral cavity to modify the populations of the oral microbiome in a subject. As further described herein, various wavelengths and intensities of light can be employed for this purpose. For example, the use of orally inserted light sources, such as lighted toothbrushes, dental floss, water-pic devices, etc. can be employed to either enhance certain oral bacteria or to destroy or negatively effect the growth of pathogenic bacteria. In certain embodiments, chemically initiated light is employed to modify the bacterial populations in one's mouth and such chemical formulations may include bioluminescent materials. In particular embodiments, glow-in-the-dark materials are used, such as oral strips, preferably bioadhesive to mucosal membranes, such that light sources can reside for desired, therapeutically effective times and intensities to provide a desired effect with respect to the bacterial growth inside the oral cavity.

The visible and near-infrared wavelengths can affect bacterial growth and thus, the use of such wavelengths of light can be employed in the various ways described herein to either enhance the growth of certain bacteria or conversely to retard the growth of other undesired bacteria. The use of photon energy transfer to affect the growth of bacteria, for example, by using non-ionizing light sources belonging to the visible and infrared spectrum, is believed to act on bacteria to modify the growth thereof. While not bound by theory, it is believed that even bacteria that do not use light as a primary energy source, still possess molecules that are involved in their physiology and that such bacteria have retained their primordial photoacceptive properties.

In various embodiments of the present invention, bacterial populations in the oral microbiota are modified through biophotoenergization and the non-thermal effect of light on photoacceptors (i.e., cytochromes, flavins, and iron-proteins) of bacteria are employed in the management of a subject's health and illness.

When certain bacteria, such as *P. denitrificans*, grows anaerobically, oxidative phosphorylation proceeds via anaerobic respiration. But less energy is formed in anaerobic versus aerobic conditions. In various aspects of the present invention, photon energy transfer employs non-ionizing light sources in the visible and infrared spectrum, including lasers, light-emitting diodes (LEDs), broadband light, and in certain embodiments, bioluminescent materials applied to the oral cavity, such as via adhesive strips, patches, mouthwash, toothpaste, etc. Preferably, the use of light to modify bacterial populations in the oral cavity, particularly outside of a dentist's office and instead, when a person is brushing or flossing their teeth at home, involves light that does not rely upon significant thermal energies, such that heat is not the predominant factor involved in modifying bacterial populations in the mouth. It is believed that this involves endogenous photo-acceptors eliciting photophysical and photochemical events at various biological scales, thus influencing cell physiology.

In certain embodiments, light having visible 400-500 nm wavelengths is used to excite flavins and flavoproteins and thus, such light acts on different cell pigments and respiratory complexes. Porphyrins, heterocyclic organic compounds complexed to hemoglobin, and other proteins and enzymes, possess the ability to absorb light at 400-450 nm. While not bound by theory, it is believed that light may induce NO release from a variety of cellular sources, and that visible light can be used to affect the structure and activities of opsin proteins, which are involved in cellular pathways of different cell types. It is believed that light in the oral cavity affects the endogenous release of reactive oxygen species (ROS) and NO, ATP production, and modulation of $Ca^{2+}$ fluxes and redox homeostasis, all of which play a key role in cell proliferation, growth, and apoptosis. Thus, the present invention can be employed to restore cell dysfunction and promote recovery from illness, such as oral mucositis experienced by cancer patients treated with chemotherapy.

While it is known that UV irradiation therapy can be used to destroy bacteria, even minimal overexposure to UV is dangerous to healthy tissue. Thus, in various embodiments of the present invention, UV light is not employed, but rather other light sources are employed, preferably light emanating from strips that adhere to the mucosal surfaces of the oral cavity. In certain embodiments, a light with 808 nm can be used to achieve decreased bacterial load. In other embodiments, *P. gingivalis, F. nucleatum, S. mutans*, and *E. faecalis* residing in a subject's oral cavity are exposed to visible light at wavelengths of 400-500 nm, at power densities between 0.26 and 1.14 W/cm2 (60-180 s), in order to reduce the growth thereof. It is believed that certain dark pigmented bacteria, such as *P. intermedia*, are susceptible to damage from light at the above wavelengths, with wavelengths at around 630 nm employed to inhibit certain bacterial growth. In certain embodiments, wavelengths to be avoided are those over 800 nm.

While not bound by theory, it is believed that the blue spectral region radiation acts through a sensitizing effect of endogenous porphyrins capable of inducing reactive oxygen species generation. In preferred embodiments, light having a wavelength of 400-410 nm (15 J/cm2) is used to reduce *P. gingivalis* growth, and preferred embodiments employ bioadhesive strips as described herein to provide light inside the oral cavity when an individual's mouth is closed. Such light sources inside the oral cavity are employed to achieve antimicrobial effects and the use of light having 400-470 nm wavelengths is preferred. Light inside the oral cavity is therefore employed to reduce the growth of oral microbiota such as Aggregatibacter *actinomycetemcomitans, P. gingivalis, Prevotella nigrescens*, and *F. nucleatum*, inducing growth inhibition, cell death, and the reduction of biofilm formation. The use of light inside the oral cavity is employed to treat diseases and as a preventative routine to reduce bacterial growth of pathogens using the non-thermal effect of light on photoacceptors (i.e., cytochromes, flavins, iron-proteins).

In one embodiment, visible light at one or more of the wavelengths of 514, 532, and 633 nm is used to induce the growth of desired bacteria, e.g. *P. aeruginosa*, and to conversely inhibit the growth of undesired bacteria, e.g. *S. aureus*. In still other embodiments, especially with respect to addressing Alzheimer's Disease, light inside the oral cavity is used in one embodiment to reduce the growth of *P. gingivalis*.

While not bound by theory, it is believed that pathogenic bacteria can be killed, or its growth retarded, by visible light due to the presence of pigments produced by such bacteria, with light energy being absorbed that therefore causes energized pigments to increase ROS formation through photodynamic therapy pathways. As such, certain embodiments are directed to targeting pigmented bacteria by exposing the same to visible light, which spares other bacteria that do not possess such pigments. In certain embodiments, the luminescence of oral strips is employed to negatively affect the growth of *Porphyromonas* spp. and *Prevotells* spp. By exposing the oral cavity to visible light, preferably at the wavelengths of 400, 410 nm, or in the range of 400-500 nm.

A major problem with bacterial biofilms is the inability of the host immune system and/or antibiotics and other antimicrobials to gain access to the bacteria protected within the biofilm. Thus, a need exists to break through the protective barrier of biofilms to treat or kill the associated bacterial infections as the biofilm can act as a reservoir for future acute infections often with lethal consequences. Light, such as a laser, can and has been used to kill bacteria. Various embodiments of the present invention, however, rely upon bioluminescence of orally administered strips to modify the bacterial composition of the oral cavity, enhancing the growth of beneficial bacteria and retarding or killing pathogenic bacteria, and thus negatively effecting the formation of biofilms that adversely affect human health.

Certain embodiments comprise the employment of bioluminescent strips that modify the oral microbiome to enhance the health of a subject, principally by enhancing the growth of beneficial bacteria or conversely, by reducing the growth of pathogenic bacteria. Bioluminescence is a type of chemiluminescence and in certain embodiments, a catalytic protein can be employed that increases the efficiency of a chemiluminescent reaction to generate luminescence. Bioluminescent compounds that may be employed in the present invention embodiments include luciferin, luciferase and aequorin. In still other embodiments, one can determine certain desired or undesired bacteria are present in the mouth, etc., and such effective means for determining the same include a film, coating or patch that includes one or more of the following characteristics: reflectance, retroreflectance, fluorescence, and photoluminescent light transmission. Certain embodiments also assist in the detection of whether a person has a certain medical condition, such as strep throat. Thus, in one embodiment, the oral patch or strip changes color, expresses bioluminescence, etc. if there is strep bacteria present in a predetermined amount. In other embodiments, certain strips are made with bioluminescent material and/or material that reacts specifically with light to kill bacteria on the strip. Projection of UV light onto the strip to destroy bacteria after a certain amount of time is one aspect of the present invention. Other embodiments, however rely upon the emission of light from the strip to light up the otherwise dark oral cavity when one's mouth is closed, thus exposing bacteria to light that would otherwise not be there.

While certain other embodiments comprise bioluminescent strips to facilitate a user's ability to view (in a mirror) the correct placement of the strips in one's throat, the light emitted from such strips can be employed to beneficially modify the oral microbiome. Bioluminescence is a type of chemiluminescence and in certain embodiments, a catalytic protein increases the efficiency of chemiluminescent reaction such that a bioluminescent protein is determined by detecting the presence of luminescence, with bioluminescent compounds employed that include luciferin, luciferase and aequorin. Incorporated herein by this reference for written description purposes in this regard is U.S. Pat. Publication No. 20110250626 to Williams, et al.

Another aspect of the present invention relates to the modification of saliva of a subject using light inside the oral cavity. Saliva plays a pivotal role in maintaining a healthy oral cavity and promotes the natural beneficial relationship between the oral microbiota and the host. Reduced salivary secretion, low salivary pH, and altered salivary composition can change the oral cavity microbiota leading to dysbiosis associated with the risk of oral diseases. In certain embodiments, the use of light is employed to improve the functionality of the salivary glands acting on the salivary flow and increasing the salivary pH and is believed to be beneficial to stimulating the immune system. This includes the employment of bioluminescent strips that adhere to the inside of an individual's oral cavity to emit light so as to modify the environment, and thus growth characteristics, of microbes in the oral cavity.

In various embodiments of the present invention the use of light in the oral cavity is employed to stimulate the production of bacteriocins and pigments by commensal bacteria, as well as the formation of desired bacterial biofilms. By doing so, there is a desired improvement in colonization resistance against pathogens.

In still other aspects of the present invention, modification of bacteria, e.g. via CRISPR systems, to provide certain bacteria with increased or decreased amounts of particular proteins, can be used, in association with light therapy, to modify the oral microbiome. For example, bacteria can be modified to generate more (or less) pigments such that when such bacteria are exposed to light, they may be damaged or conversely, protected according to their composition and the wavelengths employed. The different metabolism exhibited by aerobic and anaerobic bacteria therefore becomes a target for therapy able to discriminate and induce opposite effects.

Various embodiments of the present invention are directed to the use of bioluminescent strips or patches that are adhered to the interior of the oral cavity and express light in a fashion such that bacterial populations are modified to either increase beneficial bacteria or decrease the growth of pathogenic bacteria. The use of glow-in-the dark strips is described herein in various regards, including the use of such features to properly position such strips in a person's mouth. Other aspects of the use of such strips, however, include the modification of bacterial populations within a subject's oral cavity to promote health and to address various diseases and conditions. Bioluminescence does not come from or depend on light absorbed by an organism, but rather derives from a highly exergonic (energy yielding) chemical reaction in which excess energy is transformed into light energy instead of being all lost as heat. Such light in an individual's oral cavity can be employed to adjust the bacterial populations within the oral cavity, selectively decreasing undesired pathogenic bacteria and enhancing the growth of desired beneficial bacteria. Bioadhesive strips/patches of the present invention include bioluminescent materials incorporated therein. Bioluminescent light is emitted in wavelengths between 400 and 720 nm. And isible radiation corresponds to light in the wavelength range of 400-700 nm.

While certain preferred embodiments are directed to the use of adhesive patches or strips that illuminate the oral cavity of a user to modify the bacterial populations in the oral cavity, e.g. enhance the growth of desired bacteria and retard the growth of pathogenic bacteria, still other embodiments are directed to employing other sources of light in the oral cavity to purposefully affect the bacterial populations thereof. For example, a light irradiating toothbrush that efficiently radiates light into the mouth of a user for the purpose of modifying the microbial population within a person's oral cavity forms various aspects f the present invention. In one embodiment, an orally inserted device that is able to illuminate the oral cavity, such as a lighted toothbrush, is employed to illuminate the oral cavity in a manner that exposes bacteria to such light. For example, light of the toothbrush may preferably emit light out from the bristle portion of the toothbrush at a pre-determined intensity and wavelength to kill or retard the growth of pathogenic bacteria and to conversely, enhance the growth of beneficial oral bacteria such that preferred biofilms are either enhanced or undesired biofilms are deterred. Such a toothbrush can further have timing elements such that a predetermined time elapses wherein the light from the toothbrush is emitted at a certain frequency, intensity and wavelength to accomplish the purpose of enhancing the growth of certain beneficial bacteria and to deter the growth of undesired pathogenic bacteria. Still other embodiments are directed to dental floss that has light emitting properties, thus providing a way for light to shine on bacteria that would otherwise not be exposed to light due to bacteria being buried deep in the gum tissue or between teeth.

Still other embodiments of the present invention include the encapsulation of beneficial bacteria in oral strips that may or may not also include bioluminescent materials, thus enabling one to modify the bacterial population of the oral cavity in two respects: direct administration of beneficial bacterial and the use of light to enhance the growth thereof, as well as deterring the growth of pathogenic bacteria in the oral cavity.

Streptococci constitute 60 to 90% of the bacteria that colonize the teeth in the first 4 hours after professional cleaning. Other early colonizers include *Actinomyces* spp., *Capnocytophaga* spp., *Eikenella* spp., *Haemophilus* spp., *Prevotella* spp., *Propionibacterium* spp., and *Veillonella* spp.

The biological nitrogen cycle involves step-wise reduction of nitrogen oxides to ammonium salts and oxidation of ammonia back to nitrites and nitrates by plants and bacteria. The salivary bacterial reduction of nitrate to nitrite has been recognized as an important metabolic conversion in humans. Several enteric bacteria have also shown the ability of catalytic reduction of nitrate to ammonia via nitrite during dissimilatory respiration.

In one embodiment, the lactic acid bacterium *Lactobacillus reuteri* is employed as it is believed that by doing so, one is able to induce oxytocin, preferably in a manner that offers a sustained induction of oxytocin, unlike the short effects achieved using intranasal oxytocin sprays, etc. Thus, one aspect of the present invention relates to the employment of probiotics-induced oxytocin to reduce pain symptoms, especially in the form of an oral adhesive strip as further described herein.

Still other embodiments include a strip that includes *Lactobacillus reuteri* bacteria to induce a sustained induction of oxytocin, and providing the individual with an amount of antibiotic sufficient to reduce the number of undesired bacteria in the oral cavity. Prior to the use of the strip, an antibiotic selected from the group consisting of tetracycline hydrochloride, doxycycline, and minocycline is used to reduce the number of undesired bacteria in the oral cavity. One objective is to retard the growth conditions for spirochetes and *P. gingivalis*, believed to be associated with migraine headaches. In still other embodiments, *Veillonella* and/or *Prevotella* bacteria is provided on the strip. As one of skill in the art will appreciate, the strip may be made to include at least one polymer selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. Preferably, the strip includes at least 0.2% xylitol by weight. In certain embodiments, the strip comprises bioluminescent material. Preferably the strip is dissolvable in a person's mouth within a period of 1 hour. In certain preferred embodiments, the strip has least one encapsulated feature that contains an agent selected from the group consisting of an antibiotic; lactic acid bacteria; and xylitol, e.g. at least 200 mg of xylitol. Such a frangible capsule may be constructed so that it may be broken by the individual pressing against said strip with the individual's tongue.

Certain other embodiments of the present invention are directed to treating conjunctivitis ("pinkeye" or Madras Eye") which is an inflammation of the conjunctiva usually caused by allergic reactions or infections by bacterial or viral agents. Probiotics comprising *Enterococcus*, alone, or in combination with other probiotics, such as from the genera *Streptococcus.*, *Lactobacillus.*, *Lactococcus.*, *Bacillus*, *Bifidobacterium*, or *Saccharomyce*. Certain embodiments are directed to compositions or supplements, including food products formulated for one of human or animal consumption.

Particular embodiments of the present invention are directed to a method for increasing beneficial bacteria and decreasing pathogenic bacteria in the oral cavity of a subject by facilitating the growth of desired bacteria in a human's mouth using a bioadhesive strip. Such a strip has a first side having at least one encapsulated feature containing at least one beneficial bacteria, and a second side having a bioadhesive adapted to bind to a mucosal membrane, such as but not limited to a person's mouth, for at least 1 hour. The strip preferably includes bioluminescent material, which can be useful in facilitating a user's ability to view when viewing in a mirror, so as to place the strip in one's mouth. Such a strip also preferably has compounds residing thereon to facilitate the growth of desired bacteria beneficial to a person's health. Light emanating from the bioluminescent material decreases the growth of pathogenic bacteria populations and reduces biofilm formation. It may also induce nitric oxide release from cellular sources. In certain embodiments the bioluminescent material provides light having a wavelength of 400-410 nm that reduces *P. gingivalis* growth inside the subject's oral cavity. While light can be provided via a bioluminescent strip as described herein, it can also be provided by a light source, such as a lighted toothbrush. Using such a light source causes bacterial populations in the oral cavity to be modified through photoenergization and the non-thermal effect of the light source on bacterial photoacceptors comprising cytochromes, flavins, and iron-proteins. The light may further cause an endogenous release of reactive oxygen species, especially light having a wavelength of 400-410 nm, where the light reduces *P. gingivalis* growth inside a subject's oral cavity. In other embodiments, the light source provides a light having a wavelength above 630 nm and below 800 nm and inhibits the growth of dark pigmented bacteria, such as *P. intermedia*. In preferred embodiments, the light source provides a light that reduces the growth of oral microbiota comprising Aggregatibacter actinomycetemcomitans, *P. gingivalis*, *Prevotella nigrescens*, *F. nucleatum*, *S. mutans* and *E. faecalis* residing in a subject's oral cavity. In other embodiments, the light employed has a wavelength of 400-500 nm.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, figures, etc. will provide a basis for the scope of the present invention as it may be claimed now and in future applications.

BRIEF DESCRIPTION OF THE FIGURES

FIG. 4 is an illustration of a pre-made sheet of strips that can be disassociated with the sheet and then applied to mucosal membranes.

DETAILED DESCRIPTION OF EMBODIMENTS OF THE PRESENT INVENTION

Figure 1:
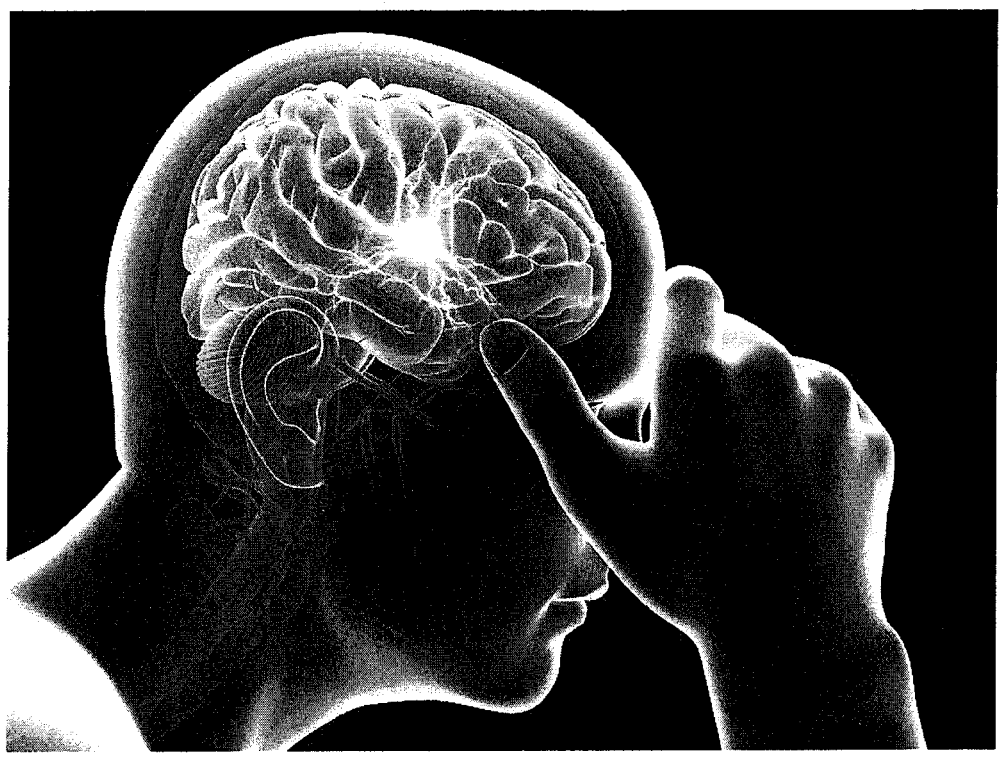
FIG. 1 is an illustration of a person experiencing the pain of a migraine headache.
Figure 2A:
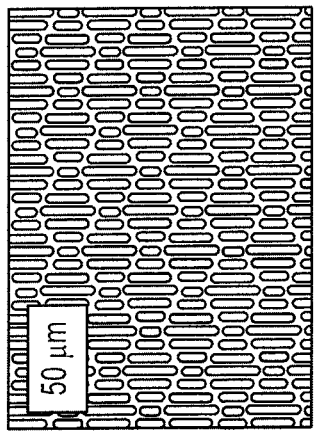
FIG. 2(*a*)-(*d*) illustrate some exemplary surface architectural patterns according to the invention.
Figure 2B:
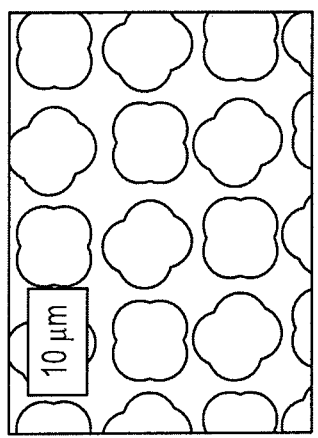
Figure 2C:
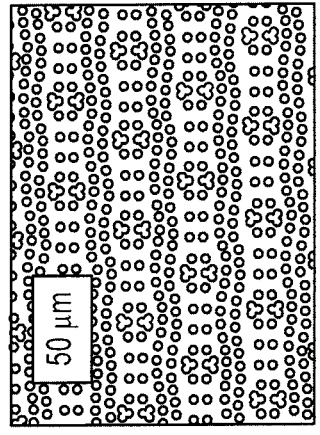
Figure 2D:
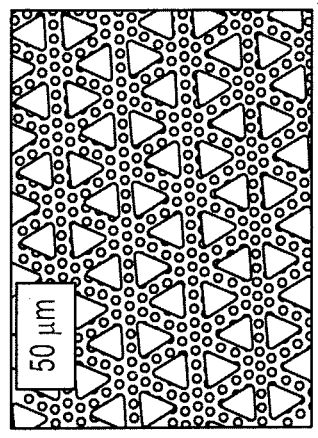
Figure 3:
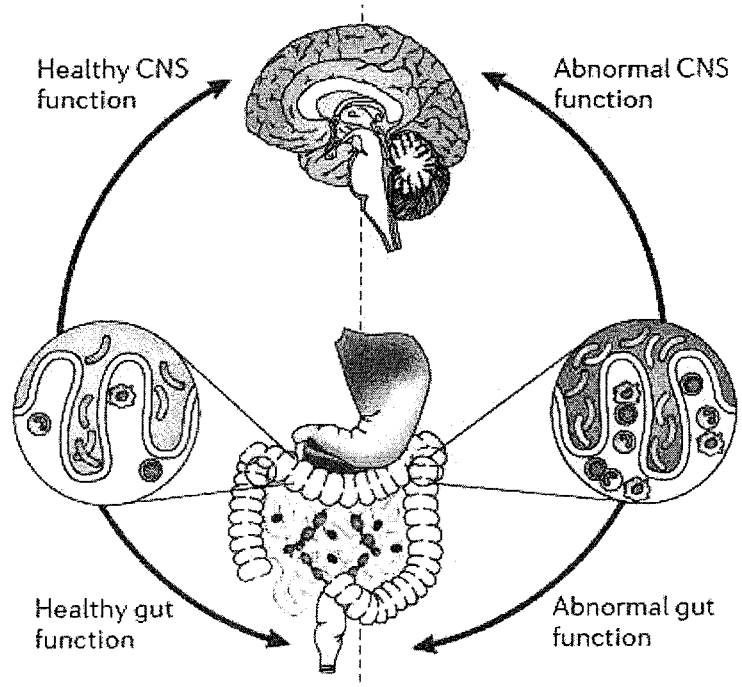
FIG. 3 is an illustration of how beneficial bacteria in an individual's gut microbiome relates to the health of the central nervous system, as well as how dysbiosis of the gut microbiome relates to various problems experienced with the central nervous system including the occurrences of migraine headaches.

One objective of the present invention is to preserve the maintenance of an ecologically balanced biodiversity of the microflora within the oral cavity as it is crucial not only to the oral health but also to the general health of the individual. Certain embodiments are directed to the use of commensal bacteria to thwart the growth and development of biofilms comprising pathogenic bacteria. In certain preferred embodiments, commensal bacteria are employed to thwart the growth and development of biofilms that are believed to be involved in the progression of Alzheimer's Disease. While not bound by theory, hydrogen peroxide production by commensal bacteria is believed to be a major mechanism of inhibition of various species of pathogenic bacteria.

Various embodiments of the present invention are directed to the use of bacteria, including but not limited to *Streptococcus* bacteria, employed to inhibit the growth of pathogenic bacteria. In still other embodiments, trace mineral micronutrients are administered, preferably to achieve balanced levels of trace minerals like iron (Fe), zinc (Zn), selenium (Se) and copper (Cu), which are imperative for optimum host health and essential to prevent progression of chronic conditions like periodontitis. Their excess as well as deficiency is believed to be detrimental to periodontal health. In certain embodiments, oral strips are impregnated with zinc salts as they are non-toxic and do not stain teeth compared with other metal salts. The zinc is believed to assist in the inhibition of growth of undesired bacteria in the oral cavity. Moreover, in other preferred embodiments, strips explicitly exclude, e.g. are devoid of, either manganese or copper, as it is known that spirochetes use the same, instead of iron.

Thus, in various embodiments, one aspect of the present invention is directed to therapies to treat or prevent the onset of periodontal disease. In certain embodiments, use of target agents to inhibit the adherence of *P. gingivalis* to supragingival plaque is employed, and such agents can be included in mouth rinses and toothpaste formulations, so that they may be easily and non-invasively administered.

With a better understanding of how the microbiota interacts with the host's physiology gained in the last few years, one aspect of various embodiments of the present invention is to integrate an individual's microbiota into a form of personalized healthcare so as to treat an individual's diseases more efficiently and in a more targeted fashion. With a more complete understanding of the AD disease process, the manipulation of the oral microbiome is focused on to modulate the otherwise normal course of AD disease progression. While Hippocrates may have been correct that food is medicine and medicine is food—and that all disease begins in the gut—the present inventors believe that before the food arrives at the gut, it must pass through the oral microbiome—and it is in the oral cavity that one can effectively address many of the diseases of the modern era, including AD. Saliva is colourless, odourless and has a relative density of 1.004-1.009 and a pH of 6.6-7.1. Saliva consists of 99% water and the remainder is organic molecules such as salivary amylase, mucopolysaccharide, mucin and lysozymes, and some inorganic matter such as $Na^+$, $K^+$, $Ca^{2+}$, $Cl^-$ and the thiocyanate ion. Levels of nitric oxide (NO) have been detected in saliva and gingival crevicular fluid collected from patients with gingivitis, aggressive periodontitis and chronic periodontitis—as compared to healthy controls. Salivary AM and NO levels distinguished patients with aggressive periodontitis from other groups. In contrast, patients with chronic periodontitis, aggressive periodontitis and gingivitis showed increased levels of NO in the gingival crevicular fluid, and higher levels of NO were found in patients with periodontitis compared with those with only gingivitis.

The microbial conversion of nitrate to nitrite in the oral cavity and the subsequent conversion to nitric oxide is an important factor in combating various diseases. While for many years, the role of nitrate in the human body has been under debate and usually not in favor of nitrate, recently there has been a revaluation of this paradigm. The present inventors submit that the bacterial reduction of nitrate to nitrite in the oral cavity is important in the progression of AD and that there are health benefits to be derived from the oral presence of nitric oxide. While elevated levels of nitrate and nitrite are associated with periodontal disease, this elevation is thought to be a response of the immune system against infection or stress. Under acidic conditions, nitrite is converted to nitric oxide and acts as an antibacterial agent. *P. intermedia* lipopolysaccharide can induce iNOS expression and stimulate the release of NO without additional stimuli. The ability of *P. intermedia* lipopolysaccharide to promote the production of NO is important in the pathogenesis of inflammatory periodontal disease, and thus in the progression of AD. The strips of the present invention in various embodiments provide a way to provide a potent inhibitor of biofilms that are implicated in periodontal disease, with proper application thereof being effective to provide subgingival margins with anti-periodontal pathogen capabilities so as to combat endodontic biofilms.

Other aspects of the present invention are directed to the use of commensal bacteria to thwart the growth and development of biofilms that are believed to be involved in the progression of AD. Hydrogen peroxide production by commensal is believed to be a major mechanism of inhibition and various species of *Streptococcus* bacteria are employed in certain embodiments of the present invention to inhibit the growth of pathogens. Trace mineral micronutrients are also imperative for optimum host health and balanced levels of trace minerals like iron (Fe), zinc (Zn), selenium (Se) and copper (Cu) are essential to prevent progression of chronic conditions like periodontitis. Their excess as well as deficiency is detrimental to periodontal health. This is specifically true in relation to Fe. Furthermore, some trace elements, e.g. Se, Zn and Cu are integral components of antioxidant enzymes and prevent reactive oxygen species induced destruction of tissues. Their deficiency can worsen periodontitis associated with systemic conditions like diabetes mellitus. In various embodiments of the present invention, the employment of bacteria that is able to generate desired levels of hydrogen peroxide are used to adjust the population of an individual's oral bacteria populations.

One aspect of the present invention is directed to a method and system that includes providing a person with a composition, particularly one or more oral compositions, that include a collection of bacteria, preferably that include the genus *Prevotella*, that produces nitric oxide to reduce the chances of an individual suffering from Alzheimer's Disease. In certain embodiments, such method and system involve the oral administration of a composition comprising *Prevotella* bacteria capable of producing nitric oxide in a manner such that the person's microflora and bacterial environment in their oral cavity is populated with such *Prevotella* bacteria. Most preferably, the *Prevotella* is attenuated to eliminate one or more virulence factors, such as adherence abilities useful in forming biofilms.

Certain methods provide for preventing the onset or progression of AD by gene editing, e.g., using CRISPR-Cas9 mediated methods to alter genes in *Prevotella* bacteria in order to promote the growth of such bacteria such that increased amounts of beneficial NO are produced. There appears to be a relationship between Nitric Oxide and Alzheimer's disease. Lack of NO production by endothelial cells due to too much ABP aggregate formation and/or free radical generation contributes to the pathology of AD. It is speculated that if NO production could be assured then AD would be significantly halted in its track. NO seems to affect the production of ABP but does not affect its clearance, thus suggesting that NO donors may work as preventative of AD, rather than reversing AD. When NO production was increased by use of a known stimulator of NO production in an animal model of AD, the levels of ABP decreased and there was a significant improvement in memory of animals. Many diseases are characterized by or associated with insufficient nitric oxide production. Experimental and clinical studies demonstrate that insufficient nitric oxide production is associated with major cardiovascular risk factors, such as hyperlipidemia, diabetes, hypertension, smoking and atherosclerosis. Nitric oxide production is also a predictive indicator of future atherosclerotic disease progression. The ability to generate nitric oxide decreases with age resulting in increased risk of heart and vascular disease. Thus, various embodiments are directed to providing beneficial bacteria in the oral cavity that produce NO.

One aspect of the present invention relates to the removal from the oral cavity of disease causing bacteria, principally gram negative bacteria associated with periodontitis, followed by antibiotic treatments to ensure such bacteria removal from the oral cavity, and then followed up within hours with a regimen that includes the purposeful exposure of a person's oral cavity with beneficial bacteria, thus promoting the avoidance of future periodontal disease. The strips as described herein can be used for each or a combination of such functions. The correct formation of a beneficial biofilm is thus one aspect of the present invention. If this last step is not implemented, then there will invariably be a biofilm generated, but often one that is not beneficial to the person, and one that could lead again to periodontitis. Thus, the purposeful exposure and administration of select bacterial species is one objective of the present invention.

*S. pyogenes* produces a wide array of virulence factors, enabling it to adhere, invade, and spread within the human host. One aspect of the present invention relates to the impairment or deletion of such virulence factors to provide a bacteria that may competitively compete with other strains, thus providing a way for a person to populate their oral cavity with a less infectious bacteria and thus, avoid sore throats.

Adherence of *Streptococcus pyogenes* to human epithelial pharangeal and oral mucosal cells can be inhibited by oligosaccharides, preferably associated with one or more strips as described herein prior to placement of the strips in a person's throat. In U.S. Pat. Nos. 5,002,759 and 5,095,106, which are incorporated by reference, oligosaccharide compositions and methods are described that inhibit the adhesion of *S. pyogenes* on pharyngeal and oral mucosa. The inhibitory activity of these oligosaccharides can be substantially enhanced by coupling them with a carrier to make glycoconjugates. Thus, in various embodiments of the present invention, in addition to the structural features of the strips as disclosed herein that have anti-bacterial properties, preferred embodiments also include one or both of oligosaccharides and glycoconjugates. Oligosaccharides may be selected from the group consisting of A-tetrasaccharide, B'-sialyllactose, lacto-N-tetraose, B-trisaccharide, fucosyl-lactose, lacto-N-neotetraose and gangliotetraose. Preferably the oligosaccharide is conjugated to human serum albumin or bovine serum albumin. Specific examples further include the oligasaccharide—conjugates Gal 1-3 Gal N-acetyl-Human Serum Albumin, lacto-N-fucopentaose 1,1,1-Human Serum Albumin, Galbeta 1-4 galactose N-acetyl beta 1-0-para amino phenyl Human Serum Albumin.

Other embodiments are directed to an oral strip having a preloaded population of bacteria residing thereon (or that can be cultured on the strip after triggering the growth of the bacteria pre-placed thereon) such that there is competitive inhibition of other bacteria, namely *S. pyogenes*, such that sore throats are avoided or at least lessened in severity.

The strips of the present invention may be configured for inter-oral administration and may contain either an anti-bacterial surface to which few, if any bacteria attach, or alternative strips have pre-determined populations of "friendly bacteria" thereon, such that the surface area for *S. pyogenes* to grow is thus limited, effecting the prevention of a sore throat and therefore providing a method for the preparation thereof and use thereof in alleviating throat conditions or throat disorders. In yet other embodiments, thin films are adapted for attachment to the mucosal membrane, in particular to the back region of a person's throat where bacteria reside, and in particular bacteria that cause disease and result in a person experiencing a sore throat, with such thin films having an effective amount of xylitol. It has been found that bacterial resistance is one of the main problems in controlling recurrent infections and the improper use of antibiotics has permitted many microorganisms to adapt and become resistant to treatment. A better way of controlling this phenomenon is through bypassing the bacteria's adaptive qualities altogether.

The naturally occurring sugar Xylitol is a natural sweetener and has an anti-adherence property that is believed to interfere with many microorganisms ability to cling to cell tissues. As bacterial infection occurs when bacteria adheres to tissues in a manner that permits colonization and growth, the use of xylitol is believed to prevent this action and in the process, stave off bacterial infection. One problem with prior art administrations of xylitol has been to provide xylitol in effective concentrations, in the proper place (e.g. in contact with particular tissue), and for an extended period time so as to achieve its anti-bacterial abilities. Sprays and merely chewing gum containing xylitol have shown some benefits in terms of dental cavity prevention and in washing of nasal tissues. But the present invention is effective in isolating the particular tissue most at risk of bacterial infection—the back of one's throat—and focuses an effective concentration of xylitol (as well as the many other agents and bacteria as described herein) on such tissue for an appropriate and effective period of time so as to reduce the number of undesired bacteria that would otherwise exist on the tissue of one's throat. Because the bacteria are not allowed to infect, antibiotics are not needed in certain embodiments of the present invention.

While not bound by theory, it is believed that xylitol disperses and disrupts biofilms and thus, in addition to its anti-adherence property, xylitol is able to help in the treatment of diseases where bacteria and other microorganisms are the causative agents. It is further believed that xylitol is effective in dispersing yeast-born bacterial microorganisms and in controlling their growth. It is also speculated that xylitol is a glucose competitor that is able to inhibit glycolysis.

Because of its five-carbon sugar alcohol structure, xylitol is unsuitable as a source of energy for most oral microorganisms, such as *Streptococcus mutans*. Yet, most *S. mutans* strains are, via the fructose phospho-transferase system, able to transport xylitol into the cell, where it is phosphorylated into xylitol-5-phosphate, which then has to be expelled from the cell. This metabolically futile xylitol cycle consumes energy stores of the cell and is thought to be responsible for the inhibition of the growth of *S. mutans* observed both in vitro and in vivo when exposed to xylitol. Because the bacteria are not killed, resistance is not as big a problem. Use of the strips of the present invention are suited for the treatment of appropriate infections and reduces the need for second and third generation antibiotics. In certain embodiments, the re-population of the mouth with a population of bacteria that are considered to be more healthy than infectious bacteria is one aspect of many embodiments of the present invention. Due to its crystalline structure, i.e., distinct single crystal, definitive form, and very dense nature, when added to a strip of the present invention, aqueous crystallized xylitol does not "dry" the strip out. Xylitol is a pentitol and is used not only as a sweetener but also as a platform chemical for the production of industrially important chemicals. Oral bacteria thrive on certain carbohydrate molecules such as sucrose, glucose, fructose and other sugars but when they ingest xylitol, they cease proliferating and cease to adhere to human tissues. Delivering xylitol via the strips of the present invention also provides other benefits, such as remineralization of teeth and reduction of plaque and halitosis by stimulating saliva flow.

The present invention provides for a strip that can be adhered to the mucosal membrane and preferably to a particular upper mouth portion of a person's mouth that contains the bacteria that causes bad breath, promotes diseases, etc. The strip, when it dissolves, releases xylitol or a similar polyol. And there is a need to slow the rate of dissolution to maintain therapeutic levels of xylitol or other polyol in the fluids of the oral cavity over longer periods of time and this is achieved by the strips of the present invention. Many causes lead to congestion and irritation of the exposed surfaces of the respiratory tract, especially the throat. The use of strips of the present invention, especially those formulated with a particular concentration of saline and with xylitol, are believed to significantly reduce and decrease snoring. Certain formulations of the strip, especially those that include particular saline concentrations, are believed to pull fluid from the mucosa and at the same time, flushes out germs, contaminants, and pollutants (pollen/dust/sand/soot/smoke, etc.) from the mucus membranes. For example, in particular embodiments, strips that are adapted to be adhered to the mucosal membrane include a preservative free hypertonic saline at 2.3% to and including 2.7% w/v (preferably 2.4% to and including 2.6% w/v) salt is effective.

Still other embodiments include combinations of various herbal and sugar components, such as xylitol and tomatidine in a mucosal adhesive strip that achieves the combined functionality of those particular ingredients, e.g. reducing bacteria and facilitating muscle tissue health.

One aspect of the present invention is directed to a microorganism that binds to *Streptococcus pyogenes*, preferably such microorganism being a lactic acid bacterium. In an especially preferred embodiment, the microorganism or the analog, fragment, derivative, mutant or combination thereof, belongs to the *Lactobacillus* genus and in other preferred embodiments, the microorganism or analog, fragment, derivative, mutant or combination thereof does not have the ability to coaggregate with commensal microorganisms of the mucous membranes. Such a microorganism is preferably selected from the group comprising *Lactobacillus lactis*, *Lactobacillus helveticus*, *Lactobacillus jensenii*, *Lactobacillus acidophilus*, *Lactobacillus bulgaricus*, *Lactobacillus amylovorus*, *Lactobacillus delbrueckii*, *Lactobacillus casei*, *Lactobacillus crispatus*, *Lactobacillus gasseri*, *Lactobacillus johnsonii*, *Lactobacillus paracasei*, *Lactobacillus pentosus*, *Lactobacillus rhamnosus*, *Lactobacillus curvatus*, *Lactobacillus plantarum*, *Lactobacillus brevis*, *Lactobacillus buchneri*, *Lactobacillus fructivorans*, *Lactobacillus hilgardii*, *Lactobacillus fermentum*, *Lactobacillus reuteri*, *Lactobacillus viridescens*, *Bifidobacterium bifidum*, *Lactobacillus ingluviei* or analogs, derivatives, fragments or mutants thereof.

Preferred products for application of various compounds and substances of the present invention include, in addition to the preferred use of strips as described herein, toothpaste, mouth washes, gargle solutions, nose sprays, mouth sprays, throat sprays, chewing gum, hydrogel, creams, etc.

Certain preferred compositions are for topical prophylaxis or treatment of microbial diseases or inflammatory diseases of the oral cavity. It is preferably for use in prevention or treatment of microbial diseases of the oral cavity but can also be used for topical prevention or treatment of microbial diseases or inflammatory diseases, preferably microbial diseases or inflammatory diseases of the skin. In some embodiments, the composition may be used to produce an antimicrobial additive for topical treatment of inflammations in the oropharyngeal space and may be used prophylactically and may be applied orally, sublingually or buccally.

For sore throat treatments, a preferred lactic acid bacteria coaggregates specifically with the pathogenic bacteria *Streptococcus pyogenes*. As adhesion is an essential first step in bacterial pathogenesis, one aspect of the present invention is focused on adhesion as a way to prevent sore throat infections. In various embodiments, *S. pyogenes* is coaggregated in the oral cavity, so that binding to epithelial cells cannot take place from the beginning. In other embodiments, the coaggregation is accomplished due to the provision of a strip that adheres to the top most portion of a person's mouth where certain bacteria are provided to coaggregate with *S. pyogenes*. Typically, the resulting cell aggregates are swallowed with saliva and the *Streptococcus pyogenes* cells are killed during gastrointestinal passage. Certain preferred bacteria used in the present invention are found on the skin flora and are able to bind to or coaggregate with the pathogenic bacterium *Streptococcus pyogenes*. Preferred lactic acid bacteria coaggregate with *Streptococcus pyogenes* or have adhesive properties with respect to these bacteria. The coaggregation of *Streptococcus pyogenes*, is not inhibited either in saliva or in the presence of sugars.

Those skilled in the art are aware that *Streptococcus pyogenes* is also known as a pathogenic wound organism, so it is especially advantageous that the coaggregation capability of the preferred microorganisms is not limited to the oral cavity but instead can also be applied to areas of the skin. Preferred microorganisms can also be used on skin, where it will also coaggregate with *Streptococcus pyogenes*.

Other aspects of the present invention involve the elimination of or reduction of the presence of certain bacteria that appear to enhance the ability of *S. pyogenes* to adhere to epithelial tissues, one of such bacteria being *Moraxella catarrhalis*. Thus, an effective reduction of *Moraxella catarrhalis* by various means, such as by an antibiotic, can be used to reduce the chances of infection with *S. pyogenes*.

Certain other embodiments of the present invention are directed to a method for reducing the likelihood of developing depression in an individual, by providing in the gut of an individual at least two bacteria from a population of beneficial bacteria selected from the group consisting of *Coprococcus, Veillonella, Roseburia, Bifidobacterium, Faecalibacterium prausnitzii* and *Prevotella*; and administering fiber to the individual to maintain a therapeutically effective amount of the beneficial bacteria in the gut of the individual. Still further embodiments include increasing the levels of at least one of *Roseburia, Coprococcus, Veillonella, Bifidobacterium, Lactobacillus*, and *Prevotella* in the individual's gut microbiome.

Still further embodiments of the present invention are directed to treating NAFLD. One strategy for NAFLD treatment encompassed by the present invention relates to a treatment for obesity that involves manipulation of an individual's gut microbiota. Thus, modulation of gut microbiota by probiotic treatment or dietary intervention provides beneficial effects with respect to body weight, influence on glucose and fat metabolism, insulin sensitivity and reduction in chronic systemic inflammation, all of which can impact the status of NAFLD. Probiotic positive effects on host metabolism are specifically directed to beneficial levels of *Lactobacillus* and/or *Bifidobacterium* strains. For example, employment of *Saccharomyces cerevisiae* var. *boulardii*, *Enterobacter halii* or Akkermansia muciniphila are used to achieve beneficial effects for obesity and NAFLD. In certain embodiments, because obstructive sleep apnea and attendant fatigue are common in patients with NAFLD, one aspect of the present invention relates to the use of "no-snore strips" as described herein (and in more extensive pending patent applications incorporated herein by this reference, e.g. U.S. Pat. No. 9,445,936) such that use of such strips can beneficially modify not only the populations of oral bacteria, but also snoring patterns, thus providing those suffering from NAFLD with a way to manage such condition to permit them to address fatigue issues and to thus sleep better, exercise more, etc.

One objective of the present invention is to preserve the maintenance of an ecologically balanced biodiversity of the microflora within the oral cavity as it is crucial not only to the oral health but also to the general health of the individual. Certain embodiments are directed to the use of commensal bacteria to thwart the growth and development of biofilms comprising pathogenic bacteria. In certain preferred embodiments, commensal bacteria are employed to thwart the growth and development of biofilms that are believed to be involved in the progression of Alzheimer's Disease. While not bound by theory, hydrogen peroxide production by commensal bacteria is believed to be a major mechanism of inhibition of various species of pathogenic bacteria.

Various embodiments of the present invention are directed to the use of bacteria, including but not limited to *Streptococcus* bacteria, employed to inhibit the growth of pathogenic bacteria. In still other embodiments, trace mineral micronutrients are administered, preferably to achieve balanced levels of trace minerals like iron (Fe), zinc (Zn), selenium (Se) and copper (Cu), which are imperative for optimum host health and essential to prevent progression of chronic conditions like periodontitis. Their excess as well as deficiency is believed to be detrimental to periodontal health. In certain embodiments, oral strips are impregnated with zinc salts as they are non-toxic and do not stain teeth compared with other metal salts. The zinc is believed to assist in the inhibition of growth of undesired bacteria in the oral cavity. Moreover, in other preferred embodiments, strips explicitly exclude, e.g. are devoid of, either manganese or copper, as it is known that spirochetes use the same, instead of iron.

Thus, in various embodiments, one aspect of the present invention is directed to therapies to treat or prevent the onset of periodontal disease. In certain embodiments, use of target agents to inhibit the adherence of *P. gingivalis* to supragingival plaque is employed, and such agents can be included in mouth rinses and toothpaste formulations, so that they may be easily and non-invasively administered.

With a better understanding of how the microbiota interacts with the host's physiology gained in the last few years, one aspect of various embodiments of the present invention is to integrate an individual's microbiota into a form of personalized healthcare so as to treat an individual's diseases more efficiently and in a more targeted fashion. With a more complete understanding of the AD disease process, the manipulation of the oral microbiome is focused on to modulate the otherwise normal course of AD disease progression. While Hippocrates may have been correct that food is medicine and medicine is food—and that all disease begins in the gut—the present inventors believe that before the food arrives at the gut, it must pass through the oral microbiome—and it is in the oral cavity that one can effectively address many of the diseases of the modern era, including AD. Saliva is colourless, odourless and has a relative density of 1.004-1.009 and a pH of 6.6-7.1. Saliva consists of 99% water and the remainder is organic molecules such as salivary amylase, mucopolysaccharide, mucin and lysozymes, and some inorganic matter such as $Na^+$, $K^+$, $Ca^{2+}$, $Cl^-$ and the thiocyanate ion. Levels of nitric oxide (NO) have been detected in saliva and gingival crevicular fluid collected from patients with gingivitis, aggressive periodontitis and chronic periodontitis—as compared to healthy controls. Salivary AM and NO levels distinguished patients with aggressive periodontitis from other groups. In contrast, patients with chronic periodontitis, aggressive periodontitis and gingivitis showed increased levels of NO in the gingival crevicular fluid, and higher levels of NO were found in patients with periodontitis compared with those with only gingivitis.

The microbial conversion of nitrate to nitrite in the oral cavity and the subsequent conversion to nitric oxide is an important factor in combating various diseases. While for many years, the role of nitrate in the human body has been under debate and usually not in favor of nitrate, recently there has been a revaluation of this paradigm. The present inventors submit that the bacterial reduction of nitrate to nitrite in the oral cavity is important in the progression of AD and that there are health benefits to be derived from the oral presence of nitric oxide. While elevated levels of nitrate and nitrite are associated with periodontal disease, this elevation is thought to be a response of the immune system against infection or stress. Under acidic conditions, nitrite is converted to nitric oxide and acts as an antibacterial agent. *P. intermedia* lipopolysaccharide can induce iNOS expression and stimulate the release of NO without additional stimuli. The ability of *P. intermedia* lipopolysaccharide to promote the production of NO is important in the pathogenesis of inflammatory periodontal disease, and thus in the progression of AD. The strips of the present invention in various embodiments provide a way to provide a potent inhibitor of biofilms that are implicated in periodontal disease, with proper application thereof being effective to provide subgingival margins with anti-periodontal pathogen capabilities so as to combat endodontic biofilms.

Other aspects of the present invention are directed to the use of commensal bacteria to thwart the growth and development of biofilms that are believed to be involved in the progression of AD. Hydrogen peroxide production by commensal is believed to be a major mechanism of inhibition and various species of *Streptococcus* bacteria are employed in certain embodiments of the present invention to inhibit the growth of pathogens. Trace mineral micronutrients are also imperative for optimum host health and balanced levels of trace minerals like iron (Fe), zinc (Zn), selenium (Se) and copper (Cu) are essential to prevent progression of chronic conditions like periodontitis. Their excess as well as deficiency is detrimental to periodontal health. This is specifically true in relation to Fe. Furthermore, some trace elements, e.g. Se, Zn and Cu are integral components of antioxidant enzymes and prevent reactive oxygen species induced destruction of tissues. Their deficiency can worsen periodontitis associated with systemic conditions like diabetes mellitus. In various embodiments of the present invention, the employment of bacteria that is able to generate desired levels of hydrogen peroxide are used to adjust the population of an individual's oral bacteria populations.

One aspect of the present invention is directed to a method and system that includes providing a person with a composition, particularly one or more oral compositions, that include a collection of bacteria, preferably that include the genus *Prevotella*, that produces nitric oxide to reduce the chances of an individual suffering from Alzheimer's Disease. In certain embodiments, such method and system involve the oral administration of a composition comprising *Prevotella* bacteria capable of producing nitric oxide in a manner such that the person's microflora and bacterial environment in their oral cavity is populated with such *Prevotella* bacteria. Most preferably, the *Prevotella* is attenuated to eliminate one or more virulence factors, such as adherence abilities useful in forming biofilms.

Certain methods provide for preventing the onset or progression of AD by gene editing, e.g., using CRISPR-Cas9 mediated methods to alter genes in *Prevotella* bacteria in order to promote the growth of such bacteria such that increased amounts of beneficial NO are produced. There appears to be a relationship between Nitric Oxide and Alzheimer's disease. Lack of NO production by endothelial cells due to too much ABP aggregate formation and/or free radical generation contributes to the pathology of AD. It is speculated that if NO production could be assured then AD would be significantly halted in its track. NO seems to affect the production of ABP but does not affect its clearance, thus suggesting that NO donors may work as preventative of AD, rather than reversing AD. When NO production was increased by use of a known stimulator of NO production in an animal model of AD, the levels of ABP decreased and there was a significant improvement in memory of animals. Many diseases are characterized by or associated with insufficient nitric oxide production. Experimental and clinical studies demonstrate that insufficient nitric oxide production is associated with major cardiovascular risk factors, such as hyperlipidemia, diabetes, hypertension, smoking and atherosclerosis. Nitric oxide production is also a predictive indicator of future atherosclerotic disease progression. The ability to generate nitric oxide decreases with age resulting in increased risk of heart and vascular disease. Thus, various embodiments are directed to providing beneficial bacteria in the oral cavity that produce NO.

One aspect of the present invention relates to the removal from the oral cavity of disease causing bacteria, principally gram negative bacteria associated with periodontitis, followed by antibiotic treatments to ensure such bacteria removal from the oral cavity, and then followed up within hours with a regimen that includes the purposeful exposure of a person's oral cavity with beneficial bacteria, thus promoting the avoidance of future periodontal disease. The strips as described herein can be used for each or a combination of such functions. The correct formation of a beneficial biofilm is thus one aspect of the present invention. If this last step is not implemented, then there will invariably be a biofilm generated, but often one that is not beneficial to the person, and one that could lead again to periodontitis. Thus, the purposeful exposure and administration of select bacterial species is one objective of the present invention.

*S. pyogenes* produces a wide array of virulence factors, enabling it to adhere, invade, and spread within the human host. One aspect of the present invention relates to the impairment or deletion of such virulence factors to provide a bacteria that may competitively compete with other strains, thus providing a way for a person to populate their oral cavity with a less infectious bacteria and thus, avoid sore throats.

Adherence of *Streptococcus pyogenes* to human epithelial pharangeal and oral mucosal cells can be inhibited by oligosaccharides, preferably associated with one or more strips as described herein prior to placement of the strips in a person's throat. In U.S. Pat. Nos. 5,002,759 and 5,095,106, which are incorporated by reference, oligosaccharide compositions and methods are described that inhibit the adhesion of *S. pyogenes* on pharyngeal and oral mucosa. The inhibitory activity of these oligosaccharides can be substantially enhanced by coupling them with a carrier to make glycoconjugates. Thus, in various embodiments of the present invention, in addition to the structural features of the strips as disclosed herein that have anti-bacterial properties, preferred embodiments also include one or both of oligosaccharides and glycoconjugates. Oligosaccharides may be selected from the group consisting of A-tetrasaccharide, B'-sialyllactose, lacto-N-tetraose, B-trisaccharide, fucosyllactose, lacto-N-neotetraose and gangliotetraose. Preferably the oligosaccharide is conjugated to human serum albumin or bovine serum albumin. Specific examples further include the oligasaccharide—conjugates Gal 1-3 Gal N-acetyl-Human Serum Albumin, lacto-N-fucopentaose 1,1,1-Human Serum Albumin, Galbeta 1-4 galactose N-acetyl beta 1-0-para amino phenyl Human Serum Albumin.

Other embodiments are directed to an oral strip having a preloaded population of bacteria residing thereon (or that can be cultured on the strip after triggering the growth of the bacteria pre-placed thereon) such that there is competitive inhibition of other bacteria, namely *S. pyogenes*, such that sore throats are avoided or at least lessened in severity.

The strips of the present invention may be configured for inter-oral administration and may contain either an antibacterial surface to which few, if any bacteria attach, or alternative strips have pre-determined populations of "friendly bacteria" thereon, such that the surface area for *S. pyogenes* to grow is thus limited, effecting the prevention of a sore throat and therefore providing a method for the preparation thereof and use thereof in alleviating throat conditions or throat disorders. In yet other embodiments, thin films are adapted for attachment to the mucosal membrane, in particular to the back region of a person's throat where bacteria reside, and in particular bacteria that cause disease and result in a person experiencing a sore throat, with such thin films having an effective amount of xylitol. It has been found that bacterial resistance is one of the main problems in controlling recurrent infections and the improper use of antibiotics has permitted many microorganisms to adapt and become resistant to treatment. A better way of controlling this phenomenon is through bypassing the bacteria's adaptive qualities altogether.

The naturally occurring sugar Xylitol is a natural sweetener and has an anti-adherence property that is believed to interfere with many microorganisms ability to cling to cell tissues. As bacterial infection occurs when bacteria adheres to tissues in a manner that permits colonization and growth, the use of xylitol is believed to prevent this action and in the process, stave off bacterial infection. One problem with prior art administrations of xylitol has been to provide xylitol in effective concentrations, in the proper place (e.g. in contact with particular tissue), and for an extended period time so as to achieve its anti-bacterial abilities. Sprays and merely chewing gum containing xylitol have shown some benefits in terms of dental cavity prevention and in washing of nasal tissues. But the present invention is effective in isolating the particular tissue most at risk of bacterial infection—the back of one's throat—and focuses an effective concentration of xylitol (as well as the many other agents and bacteria as described herein) on such tissue for an appropriate and effective period of time so as to reduce the number of undesired bacteria that would otherwise exist on the tissue of one's throat. Because the bacteria are not allowed to infect, antibiotics are not needed in certain embodiments of the present invention.

While not bound by theory, it is believed that xylitol disperses and disrupts biofilms and thus, in addition to its anti-adherence property, xylitol is able to help in the treatment of diseases where bacteria and other microorganisms are the causative agents. It is further believed that xylitol is effective in dispersing yeast-born bacterial microorganisms and in controlling their growth. It is also speculated that xylitol is a glucose competitor that is able to inhibit glycolysis.

Because of its five-carbon sugar alcohol structure, xylitol is unsuitable as a source of energy for most oral microorganisms, such as *Streptococcus mutans*. Yet, most *S. mutans* strains are, via the fructose phospho-transferase system, able to transport xylitol into the cell, where it is phosphorylated into xylitol-5-phosphate, which then has to be expelled from the cell. This metabolically futile xylitol cycle consumes energy stores of the cell and is thought to be responsible for the inhibition of the growth of *S. mutans* observed both in vitro and in vivo when exposed to xylitol. Because the bacteria are not killed, resistance is not as big a problem. Use of the strips of the present invention are suited for the treatment of appropriate infections and reduces the need for second and third generation antibiotics. In certain embodiments, the re-population of the mouth with a population of bacteria that are considered to be more healthy than infectious bacteria is one aspect of many embodiments of the present invention. Due to its crystalline structure, i.e., distinct single crystal, definitive form, and very dense nature, when added to a strip of the present invention, aqueous crystallized xylitol does not "dry" the strip out. Xylitol is a pentitol and is used not only as a sweetener but also as a platform chemical for the production of industrially important chemicals. Oral bacteria thrive on certain carbohydrate molecules such as sucrose, glucose, fructose and other sugars but when they ingest xylitol, they cease proliferating and cease to adhere to human tissues. Delivering xylitol via the strips of the present invention also provides other benefits, such as remineralization of teeth and reduction of plaque and halitosis by stimulating saliva flow.

The present invention provides for a strip that can be adhered to the mucosal membrane and preferably to a particular upper mouth portion of a person's mouth that contains the bacteria that causes bad breath, promotes diseases, etc. The strip, when it dissolves, releases xylitol or a similar polyol. And there is a need to slow the rate of dissolution to maintain therapeutic levels of xylitol or other polyol in the fluids of the oral cavity over longer periods of time and this is achieved by the strips of the present invention. Many causes lead to congestion and irritation of the exposed surfaces of the respiratory tract, especially the throat. The use of strips of the present invention, especially those formulated with a particular concentration of saline and with xylitol, are believed to significantly reduce and decrease snoring. Certain formulations of the strip, especially those that include particular saline concentrations, are believed to pull fluid from the mucosa and at the same time, flushes out germs, contaminants, and pollutants (pollen/dust/sand/soot/smoke, etc.) from the mucus membranes. For example, in particular embodiments, strips that are adapted to be adhered to the mucosal membrane include a preservative free hypertonic saline at 2.3% to and including 2.7% w/v (preferably 2.4% to and including 2.6% w/v) salt is effective.

Still other embodiments include combinations of various herbal and sugar components, such as xylitol and tomatidine in a mucosal adhesive strip that achieves the combined functionality of those particular ingredients, e.g. reducing bacteria and facilitating muscle tissue health.

To provide necessary and sufficient written disclosure and enablement of the various embodiments of the present invention, the following references are incorporated by reference in their entireties: U.S. Pat. No. 9,017,718 to Tan; 20140065218 to Lang et. al.; U.S. Pat. Nos. 6,599,883; 8,383,201; 5,158,789; 2007/0218114 to Sorousch; 2004/0136923 to Davidson; U.S. Pat. No. 8,999,372 to Davidson; 2009/0196907 to Bunick; 2009/0196908 to Lee; 2003/0124178 to Haley; 2007/0293587 to Haley; 2010/0285098 to Haley; 2006/0204591 to Burrell; U.S. Pat. No. 7,087,249 to Burrelll; U.S. Pat. No. 6,210,699 to Acharya; U.S. Pat. No. 8,865,211 to Tzannis; 2014/0199266 to Park; U.S. Pat. No. 6,599,883 to Romeo; PCT/US2008/080362 to Dussia; 2007/0218114 to Duggan; 2004/0136923 to Davidson; 2011/0142942 to Schobel; 2004/0120991 to Gardner et al.; Fuchs et al. U.S. Pat. No. 4,136,162; 2004/0136923 to Davidson; U.S. Pat. No. 4,163,777 to Mitra; U.S. Pat. No. 5,002,970 to Eby, III; 2004/0096569 to Barkalow et al.; 2006/0035008 to Virgallito et al.; 2003/0031737 to Rosenbloom; U.S. Pat. No. 6,919,373 to Lam et al.; 2005/0196358 to Georglades et al.; U.S. Pat. No. 3,832,460 to Kosti; 2002/002057 to Battey et al.; 2004/0228804 to Jones, et al.; U.S. Pat. No. 6,054,143 to Jones; U.S. Pat. No. 5,719,196 to Uhari; 2015/0150792 to Klingman; 2014/0333003 to Allen; 2014/0271867 to Myers; 2014/0356460 to Lutin; 2015/0038594 to Borges; U.S. Pat. No. 6,139,861 to Friedman, US pat. Publication No. 20140065218202220071877 to Zenobia, et al. and 20120148629 and 20150017143 to Holvoet, et al.

One aspect of the present invention is directed to a microorganism that binds to *Streptococcus pyogenes*, preferably such microorganism being a lactic acid bacterium. In an especially preferred embodiment, the microorganism or the analog, fragment, derivative, mutant or combination thereof, belongs to the *Lactobacillus* genus and in other preferred embodiments, the microorganism or analog, fragment, derivative, mutant or combination thereof does not have the ability to coaggregate with commensal microorganisms of the mucous membranes. Such a microorganism is preferably selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum, Lactobacillus ingluviei* or analogs, derivatives, fragments or mutants thereof.

Preferred products for application of various compounds and substances of the present invention include, in addition to the preferred use of strips as described herein, toothpaste, mouth washes, gargle solutions, nose sprays, mouth sprays, throat sprays, chewing gum, hydrogel, creams, etc.

Certain preferred compositions are for topical prophylaxis or treatment of microbial diseases or inflammatory diseases of the oral cavity. It is preferably for use in prevention or treatment of microbial diseases of the oral cavity but can also be used for topical prevention or treatment of microbial diseases or inflammatory diseases, preferably microbial diseases or inflammatory diseases of the skin. In some embodiments, the composition may be used to produce an antimicrobial additive for topical treatment of inflammations in the oropharyngeal space and may be used prophylactically and may be applied orally, sublingually or buccally.

For sore throat treatments, a preferred lactic acid bacteria coaggregates specifically with the pathogenic bacteria *Streptococcus pyogenes*. As adhesion is an essential first step in bacterial pathogenesis, one aspect of the present invention is focused on adhesion as a way to prevent sore throat infections. In various embodiments, *S. pyogenes* is coaggregated in the oral cavity, so that binding to epithelial cells cannot take place from the beginning. In other embodiments, the coaggregation is accomplished due to the provision of a strip that adheres to the top most portion of a person's mouth where certain bacteria are provided to coaggregate with *S. pyogenes*. Typically, the resulting cell aggregates are swallowed with saliva and the *Streptococcus pyogenes* cells are killed during gastrointestinal passage. Certain preferred bacteria used in the present invention are found on the skin flora and are able to bind to or coaggregate with the pathogenic bacterium *Streptococcus pyogenes*. Preferred lactic acid bacteria coaggregate with *Streptococcus pyogenes* or have adhesive properties with respect to these bacteria. The coaggregation of *Streptococcus pyogenes*, is not inhibited either in saliva or in the presence of sugars.

Those skilled in the art are aware that *Streptococcus pyogenes* is also known as a pathogenic wound organism, so it is especially advantageous that the coaggregation capability of the preferred microorganisms is not limited to the oral cavity but instead can also be applied to areas of the skin. Preferred microorganisms can also be used on skin, where it will also coaggregate with *Streptococcus pyogenes*.

Certain bacteria employed herein specifically coaggregate the pathogenic bacterium *Streptococcus pyogenes*, but do not bind any other commensal microorganisms. In particular embodiments, particular cultures are employed and a CRISPR-Cas system is used to modify such cultures to remove certain virulence factors and/or to promote their survival in the oral cavity. The CRISPR-Cas system is preferably employed to excise the virulence factors of one or more of the following bacteria: *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentoses, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermen turn, Lactobacillus reuteri, Lactobacillus viridescens, Bifidobacterium bifidum, Lactobacillus ingluviei* and preferably selected from the group comprising the following microorganisms deposited with the German Collection for Microorganisms and Cell Cultures where they are numbered as DSM 25972, DSM 25987, DSM 25988, DSM 25989, DSM 25973 and have been in accordance with the Budapest Treaty regarding International Recognition of the Deposition of Mic Other LAB that may be employed in various embodiments include the following: *Lactobacillus slaivarius* C/CC 23174; *Lactobacillus plantarum* CGMCC 1.557, *Lactobacillus rhamnosus* ATCC 53103, and *Lactobacillus acidophilus* ATCC 4356. In other particular embodiments, the use of *S. oralis* and *S. salivarius* may be used in combination to inhibit growth of *S. pyogenes*, with speculation being that *S. salivarius* may achieve this feat via bacteriocin secretion. Epithelial cells are believed to be protected from infection by *S. pyogenes* when a biofilm containing *S. oralis* and *S. salivarius* is applied, with *S. pyogenes* unable to adhere to such tissue, thus the individual is protected from the adherence, internalization, and cytotoxic effects of a sore throat.

Other aspects of the present invention involve the elimination of or reduction of the presence of certain bacteria that appear to enhance the ability of *S. pyogenes* to adhere to epithelial tissues, one of such bacteria being *Moraxella catarrhalis*. Thus, an effective reduction of *Moraxella catarrhalis* by various means, such as by an antibiotic, can be used to reduce the chances of infection with *S. pyogenes*.

There is a higher prevalence of headaches among people who regularly experience GI symptoms compared to control groups without GI complaints. Colic has also been suggested as an early life expression of migraine and thus, the present inventors believe that there is an association between migraine and infantile colic. Infantile colic is a common cause of inconsolable crying during the first months of life with incidence rates ranging from 5 to 19%. Mothers with a history of migraine were 2.6 times as likely to have colic as infants than those mothers without a maternal history of migraine. Infants with abdominal colic have a lower intestinal microbiota diversity and stability as compared to control infants in the first weeks of life. Children with migraines are more likely to have experienced infantile colic compared with controls.

Irritable bowel syndrome (IBS) is a functional bowel disorder characterized by abdominal pain, bloating, discomfort, and marked changes in bowel habits. IBS and migraine are both 2-3 times more prevalent in women than in men.

IBS has been shown to be a disorder with an increased intestinal permeability and this permeability increases with more severe IBS symptoms.

The present inventors contend that there is a strong relationship between GI disorders and migraine. One of the links between inflammatory diseases and migraine are enhanced pro-inflammatory immune responses. A strong trigger of pro-inflammatory immune responses is the leakage of lipopolysaccharides (LPS) from the intestinal lumen into the circulation. Enhanced levels of LPS can enter the circulation when the intestinal permeability is increased. Depending on genetic susceptibility, pro-inflammatory responses can occur in different parts of the body, e.g., in case of migraine on the nociceptors of the trigeminal nerve.

Gut permeability and inflammation are bi-directionally related; increased permeability can cause inflammation, but inflammation can also cause increased gut permeability. An increased gut permeability, and thereby increased translocation of LPS, can be caused by multiple factors like medicines, exercise, mast cell activation, high fat diet, stress, etc. The most used method to measure epithelial barrier function is with the lactulose/mannitol test. Mannitol is transported via the transcellular pathway whereas lactulose is absorbed through the paracellular pathway. In case of increased permeability, more lactulose passes the barrier and eventually ends up in the urine. Therefore, an increase in intestinal permeability is characterized by an increased ratio of lactulose/mannitol. It is believed that the reduction of the permeability of the intestine results in relief of migraine in the subgroup of patients in whom intestinal permeability plays a role in the disease. Subjects with food allergies have an increased intestinal permeability compared with healthy controls.

The brain-gut-microbiome axis is the bidirectional communication between the central nervous system and the gastrointestinal tract. The underlying mechanisms include increased gut permeability and inflammation. Probiotics decrease intestinal permeability as well as inflammation, and therefore reduce the frequency and/or intensity of migraine attacks. In accordance with various embodiments of the present invention, a combination of various bacterial strains may be employed to combat migraines and dizziness including: *Lactobacillus acidophilus* DDS-1, *Lactobacillus bulgaricus*, *Enterococcus faecium* and *Bifidobacterium bifidum*.

Probiotics are living microorganisms that have beneficial effects on the health of the host. The most used probiotics are lactobacilli and bifidobacteria. Effects of probiotics are dependent on the used species and strain. Probiotics in the treatment of GI disorders is believed effective due to the strengthening of the intestinal barrier of a person. Probiotics have shown to be able to improve the epithelial barrier function via different mechanisms. Similarly, probiotics play a role in maintaining or improving gut barrier function as well as in migraine patients with an enhanced intestinal permeability. Migraine prevalence is associated with gastrointestinal disorders. A combination of different probiotics (*Lactobacillus acidophilus, Lactobacillus bulgaricus, Enterococcus faecium,* and *Bifidobacterium bifidum*) can be employed for such purpose. Certain methods of the present invention are directed to probiotic formulations included on or encapsulated into a strip of the present invention such that the desired bacteria is delivered to the mucosal membrane. Such strips may include one or more desired bacterial species, useful for promoting or maintaining the health and general well-being of humans, including but not limited to the following: organisms of *Enterococcus faecium*, including strain NCIMB 40371, deposited on 25 Feb. 1991 in accordance with the provisions of the Budapest Treaty, in the National Collections of Industrial and Marine Bacteria Limited, Aberdeen, under Accession No. NCIMB 40371.

Dental plaque, a sticky colorless film, is caused by bacterial deposits accumulating on tooth or implant surfaces along the gingival margins and results in the destruction of tooth-supporting tissues. Dental plaque formation starts in cracks, grooves and surface roughness on teeth and/or dental implants. In any given plaque sample, it is not uncommon to detect 30 or more bacterial species. Biofilms that colonizes the tooth surface may be among the most complex biofilms that exist in nature. The bacteria associated with periodontal diseases reside in biofilms both above and below the gingival margin. The supragingival biofilm is attached to the tooth or the implant and predominated by *Actinomyces* species. The subgingival biofilm is typically more complex and can either attach to the tooth or implant, or to the gingival tissue. Three microbe species are believed to be main players in the cause the periodontal diseases: *A. actinomycetemcomitans, P. gingivalis* and *B. forsythus*. Also, *F. nucleatum, Campylobacter* rectus, P. *Intermedia, P. nigrescens, Eubacterium nodatum, P. micros* and various spirochetes have been singled out that may also be important species in periodontal disease.

The destruction of tooth-supporting tissues results in a deepening of the space (periodontal pocket) between the root of the tooth and the gum tissue. Second to tooth decay, periodontal diseases are the most frequent oral diseases and may lead to partial or complete tooth or bone loss. It has been estimated that they affect as much as between 70-90% of the world population, and they are the major cause of tooth loss in people over 35 years of age. In periodontitis the infection has progressed to involve the oral tissues which retain the teeth in the jawbone. If untreated, periodontitis ultimately leads to loss of the affected tooth. Chronic periodontitis, the most frequently occurring form of periodontitis, results in inflammation within the supporting tissues of the teeth, progressive loss of attachment as well as progressive alveolar bone resorption. This form of periodontitis is characterized by pocket formation and/or recession of the gingiva. As the destruction advances, the mobility and movement of teeth increase, finally causing spontaneous loss of a tooth or a necessity of tooth extraction. Treatment of periodontal diseases usually involves the removal of bacterial deposits and dental calculus. However, it is difficult to have full access for treating deeper periodontal pockets, resulting in remaining bacteria that may re-infect the tissue.

$O_2$ and NO act as environmental cues that trigger the coordinated expression of virulence genes and metabolic adaptations necessary for survival within a host. NO concentrations may be produced by fecal microbiota from nitrate, with the nitrate being reduced to ammonium by the dissimilatory nitrate reduction to ammonium (DNRA) pathway. Gastrointestinal microbiota can generate substantial amounts of NO by DNRA, rather than by the generally accepted denitrification or L-arginine pathway. Bacterial nitrate reduction to ammonia. as well as the related NO formation in the gut, is believed to be an important aspect of the overall mammalian nitrate/nitrite/NO metabolism, demonstrating how the microbiome links diet and health.

Biofilm initiated diseases are by no means unique to the oral cavity. Approximately 65% of infections that affect the human are caused by organisms growing in biofilms. These include dental caries, periodontal disease, otitis media, musculoskeletal infections, necrotizing fasciitis, biliary tract infection, osteomyelitis, bacterial prostatitis, native valve endocarditis, meloidosis, prosthetic as well as orthopedic complications and cystic fibrosis pneumonia. Characteristics are persistence and chronicity of the infections as well as the difficulty in eradication.

The present inventors also submit that migraine headache is a precursor to Alzheimer's disease as it is associated with the same causative factor, namely periodontitis. As such, and as addressed in the present description and in co-pending cases, incorporated herein by this reference, the treatment of migraines by addressing the breakdown of biofilms so as to kill particular bacteria, including spirochetes found in the oral cavity. Strips of the present invention can be employed to position agents, including beneficial bacteria, bacteria modified employing CRISPR-Cas systems, and the use of antibiotics effective against various gram negative bacteria, including but not limited to spirochetes, forming various embodiments of the present invention. There are several aspects that are similar, if not the same in the processes of both illnesses. Risk factors common for patients suffering from each disorder include visual dysfunction, depression, lethargy, mood changes, sense of pain to non-painful stimuli, inability to produce purposeful coordinated movements, and in women changes in ovarian hormone levels. The neurotransmitter systems and inflammatory processes throughout the body are directly related to variations in estrogen and progesterone levels.

One aspect of the present invention relates to the removal from the oral cavity of disease causing bacteria, principally gram negative bacteria associated with periodontitis, followed by antibiotic treatments to ensure such bacteria removal from the oral cavity, and then followed up within hours with a regimen that includes the purposeful exposure of a person's oral cavity with beneficial bacteria, thus promoting the avoidance of future periodontal disease. The strips as described herein can be used for each or a combination of such functions. The correct formation of a beneficial biofilm is thus one aspect of the present invention. If this last step is not implemented, then there will invariably be a biofilm generated, but often one that is not beneficial to the person, and one that could lead again to periodontitis. Thus, the purposeful exposure and administration of select bacterial species is one objective of the present invention.

Streptococci constitute 60 to 90% of the bacteria that colonize the teeth in the first 4 hours after professional cleaning. Other early colonizers include *Actinomyces* spp., *Capnocytophaga* spp., *Eikenella* spp., *Haemophilus* spp., *Prevotella* spp., *Propionibacterium* spp., and *Veillonella* spp.

Antibiotics can be prescribed at a low dose for longer term use, or as a short-term medication to deter bacteria from re-colonizing. Preferably, in various embodiments of the present invention, strips that contain appropriate amounts and types of antibiotics are employed to adjust the population of the oral and the gut microbiome of a person to alleviate migraine and dizziness symptoms. Incorporated by reference in its entirety is U.S. Pat. No. 9,445,936, directed to the use of mucosal strips, and especially oral strips, that can be provided with various bacterial components to adjust and modify the oral microbiome of an individual. It is sometimes advisable to undergo a treatment with antibiotics so as to reduce the number of other undesired bacteria in the oral cavity, prior to the use of the strips having the desired bacteria included thereon. Antibiotics which include tetracycline hydrochloride, doxycycline, and minocycline are the primary drugs used in periodontal treatment and that are preferred for use in the strips as described herein. Such strips with these agents have antibacterial properties, reduce inflammation and block collagenase (a protein which destroys the connective tissue). Metronidazole is generally used in combination with amoxicillin or tetracycline to combat inflammation and bacterial growth in severe or chronic periodontitis and the use of these antibiotics on or encapsulated on strips of the present invention permit selective administration to the oral cavity in a manner that has never been done before. In preferred embodiments, the direct delivery of antibiotics to the surfaces of the gums by using the strips as described herein is preferred and are extremely effective when used after scaling and root planing procedures. Among the various existing agents that can be incorporated into the strips of the present invention, especially those that encapsulate such agents such that a person can self-administer the agents via tongue pressure applied to frangible shells containing such material, are as follows: a doxycycline gel that conforms to the contours of gum surfaces and solidifies over them; Chlorhexidine, a powerful antibacterial antiseptic; tetracycline hydrochloride; metronidazole; and Minocycline. In certain embodiments, the strips as described herein are employed to modify the oral microbiome of an individual to treat migraines. Thus, a buccal bioadhesive strip is preferably used that has a first and second side, with the first side having a surface comprising a pattern defined by a plurality of spaced apart features each having at least one microscale dimension and having at least one neighboring feature having a substantially different geometry, and wherein an average spacing between adjacent ones of said features is between 0.5 and 5 .mu.m in at least a portion of the surface. The first side has a bioadhesive that is adapted to bind to a mucosal membrane for at least 1 hour while inside a person's mouth. The strip may, for example, extend over a majority of the soft palate and preferably includes xylitol. Other embodiments have the strip including at least one encapsulated pocket containing one of an analgesic, a lactic acid bacteria, or another of the desired bacteria as described herein. FIG. 4 is an illustration of a pre-made sheet 100 of strips 120 that can be disassociated with the sheet and then applied to mucosal membranes. FIG. 5 is a side view of one embodiment of a strip 120 having an outer layer, an adhesive layer, a layer with an encapsulated agent contained there between. FIG. 6 is a side view of one embodiment where the encapsulated agent 110 is encapsulated into small beads that are frangible via pressure of an individual's tongue pressing against the strip so as to force it into the roof of a person's mouth.

A major problem with bacterial biofilms is the inability of the host immune system and/or antibiotics and other antimicrobials to gain access to the bacteria protected within the biofilm. Thus, a need exists to break through the protective barrier of biofilms to treat or kill the associated bacterial infections as the biofilm can act as a reservoir for future acute infections often with lethal consequences. Although a laser can be used to kill bacteria, this method in isolation does not necessarily remove the bacteria, and thus a biofilm can remain on the implant which can hinder osseointegration and may act as a source of later infection. Antimicrobial agents are not effective at normal dosage, as the minimum inhibitory concentration for antibiotics for an organism in biofilm mode might be 1000-1500 times higher than for the same organism in the planktonic state. Periodontal diseases are infections caused by microorganisms that colonize the tooth or implant surface at or below the gingival margin. While these infections have many properties in common with other infectious diseases, they exhibit unique properties conferred by their site of colonization and the nature of the environment in which they reside. The onset of the diseases is usually delayed for prolonged periods of time after initial colonization by the pathogens.

Thus certain embodiments of the present invention are directed to a prophylactic method for treating chronic migraine comprising (after the above referenced steps of removing pathogenic bacteria associated with a person's periodontitis, including after antibiotic applications) administering on a daily basis to humans a composition comprising: probiotics selected from the group consisting DDS-1 strain of *Lactobacillus acidophilus*, *Lactobacillus bulgaricus*, *Lactobacillus johnsonii*, *Bifidobacterium bifidum* and *Enterococcus faecium* in a unit dosage amount ranging from 1000 to 3000 mg. Useful probiotic agents include (in addition to the numerous others referenced herein) *Bifidobacterium* sp. or *Lactobacillus* species or strains, e.g., *L. acidophilus*, *L. rhamnosus*, *L. plantarum*, *L. reuteri*, *L. paracasei* subsp. *paracasei*, or *L. casei* Shirota; *Lachnospira*, *Veillonella*, *Faecalibacterium* and *Rothia*, and *Prevotella*.

Human oral bacteria interact with their environment by attaching to surfaces and establishing mixed-species communities. Several oral bacterial species are amenable to genetic manipulation for molecular characterization of communication both among bacteria and between bacteria and the host, Due to the dynamics of growth and adherence, the bacterial populations in the oral cavity are constantly changing, even during the intervals between normal daily oral hygiene treatments. The various species within oral biofilms function as a coordinated community that uses intra- and interspecies communication.

Development of the oral microbial community involves competition as well as cooperation among the 500 species that compose this community, including the following: *Actinobacillus actinomycetemcomitans*, *Actinomyces israelii*, *Actinomyces naeslundii*, *Capnocytophaga gingivalis*, *Capnocytophaga ochracea*, *Capnocytophaga sputigena*, *Eikenella corrodens*, *Eubacterium* spp., *Fusobacterium nucleatum*, *Haemophilus parainfluenzae*, *Porphyromonas gingivalis*, *Prevotella denticola*, *Prevotella intermedia*, *Prevotella loescheii*, *Propionibacterium acnes*, *Selenomonas flueggei*, *Streptococcus gordonii*, *Streptococcus mitis*, *Streptococcus oralis*, *Streptococcus sanguis*, *Treponema* spp., and *Veillonella atypica*. Although *F. nucleatum* is often considered a periodontal pathogen, it may instead contribute to maintaining homeostasis and improving host defense against true pathogens.

Competitive and cooperative mechanisms may be central to successful mixed species colonization as well as the proper succession of genera known to occur on teeth in both health and disease. Within the oral cavity, bacteria form multispecies communities that are distinguishable primarily by their location (supragingival versus subgingival versus epithelial). The subgingival community has the highest species richness and the greatest capacity for pathogenic outcome, such as periodontal tissue destruction.

It has been shown in vivo that veillonellae are not capable of colonizing the tooth surface without streptococci as metabolic partners and that larger populations of veillonellae develop in coculture with streptococci that recognize them as a coaggregation partner than in coculture with streptococci with which they do not coaggregate.

While migraines and Alzheimer's Disease share certain similarities in terms of bacterial and nerve passages of material to the brain, it is as yet unknown if the spirochetes believed responsible for the majority of AD is also associated with migraines and cluster headaches. About 60 oral species of *Treponema* have been identified, and spirochetes constitute a large percentage of the total oral bacterial numbers. Accordingly, a large *T. denticola* population could benefit greatly through interaction with a small *P. gingivalis* population. A stimulatory effect of *P. gingivalis* supernatant on *T. denticola* growth points to a synergistic interaction between *P. gingivalis* and other anaerobic bacteria such as oral spirochetes, and may be increased growth and increased virulence of these potential periodontal pathogens.

One aspect of the present invention is to avoid a large population of spirochetes in the oral cavity and one way of doing so involves limiting the population of other bacteria that spirochetes depend upon to thrive and grow. Thus, one aspect of the present invention is directed to the limitation or destruction or the retarding of growth conditions for spirochetes, which includes the limitation of the presence of *P. gingivalis*. Subtle regulation of gene expression in any organism within a community may lead to significant changes in the organism's ability to participate in community activities, such as use of community-formed metabolic end products as nutrients. Thus, interference with the biofilms relied upon for spirochetes growth and maintenance is one aspect of the present invention, which may be achieved via the use of oral strips of the present invention that have structural features thereon that deter bacteria growth, and that may also have antibiotics as well as beneficial bacteria residing thereon, and alternatively or in addition to, may have xylitol on the strip.

One aspect of the present invention is to trigger small changes in a person's oral and/or gut microbiome such that they cause large shifts in population composition and metabolic output of mixed-species communities. In certain embodiments, this is accomplished by inactivation of a gene (via CRISPR-Cas or CRISPR-Cpf1) involved in mixed-species community formation to cause a subtle variation in an organism's phenotype only during critical transitions in population composition and have no effect on population composition before or after the transition.

In still further particular embodiments, the *Treponema denticola* genome is modified to target the expression of particular chromosomal integrons, as it is the only human-associated bacterial species that harbors chromosomal integrons, with no integrons in other *Treponema* species being found. For example, in one particular embodiment of the present invention, genes from *Treponema* are modified to excise one or more virulence factors to address the progression of diseases, such as Alzheimer's disease, dizziness, migraines and cluster headaches, by addressing the causative factors of such diseases in the oral cavity of the person, prior to the full-blown development of such diseases. Chronic periodontitis is an inflammatory disease that is caused by the accumulation of bacteria in the form of a biofilm in the periodontal pocket. It can be treated with oral hygiene in conjunction with β-lactam antibiotics. Many oral anaerobic bacteria associated with chronic periodontal diseases have developed resistance to β-lactam antibiotics by virtue of their production of β-lactamase enzymes. Using CRISPR-Cas techniques to delete virulence factors and to restore antibiotic sensitivity to permit use of known effective antibiotics, is one aspect of the present invention.

A high prevalence of β-lactamase-producing oral anaerobic bacteria has been found in patients with chronic periodontitis. As a large percentage of bacteria carry a gene that renders them resistant to β-lactam antibiotics, alternative antimicrobial agents should be employed in patients that are non-responsive to β-lactam antibiotics. Use of CRISPR-Cas systems to render particular bacteria susceptible to such antibiotics is one aspect of the present invention, as well as the purposeful exposure of a person's oral cavity (after existing bacterial flora has been substantially removed) to replace the flora with a CRISPR-Cas system modified bacteria culture such that the control over the oral population of bacteria can be achieved, such as by rendering such bacteria susceptible to antibiotics.

Yet another aspect of the present set invention is directed to the employment of phospholipid vesicles in addressing desired modifications to the human microbiome, and in particular to the oral microbiome. Bacterial membrane vesicles (MVs), released by many bacteria, mainly consist of the cell membrane and typically range from 20 to 400 nm in size. Bacterial MVs are involved in several biological functions, such as delivery of cargo, virulence and gene transfer. Although MV biogenesis and biological roles are yet to be fully understood, one aspect of the present invention relates to the genetic engineering of such MVs to tailor them for applications in drug delivery systems and nanobiocatalysts, MV vaccines, etc. MVs have been found to mediate diverse functions, including promoting pathogenesis, enabling bacterial survival during stress conditions and regulating microbial interactions within bacterial communities. Modification and increased expression of such vesicles, including the ability to employ CRISPR-Cas systems to affect the transfer of desired components to the oral cavity via such vesicles, is part of various embodiments of the present invention. The existence of membrane vesicles increases the complexity involved in the diffusion of secreted substances during microbial interactions and MV secretion has been observed in Gram-negative bacteria as well as in other prokaryotes, including Gram-positive bacteria and archaea. MVs contain proteins, DNA, RNA and quorum sensing signals, and these substances are transferred to cells. MVs have unique characteristics, including the fact that several chemical substances are highly concentrated in MVs, the interior substances in MVs are protected against environmental stresses, and MVs play a role in effectively delivering these substances to cells.

In one particular aspect of the present invention, MVs of human specific pathogens are employed to incapacitate the pathogenic nature of such bacteria. The association between MVs and eukaryotic cells has been studied in pathogenic bacteria, and MVs secreted from pathogens transfer virulent factors to cells. In particular, specific proteins localized on the surface of MVs increase the association with epithelial cells, believed to be due to increasing the association of MV lipopolysaccharide with cells.

Microbial predation using MVs occurs when virulent factors or peptidoglycan hydrolytic enzymes contained in MVs are transferred to other bacterial cells. It has been suggested that the mechanism of bacterial lysis via MVs secreted from Gram-negative bacteria differs in whether recipient cells are Gram-negative or positive. Thus, cell-to-cell communications in the oral cavity involve microbes intricately communicating through methods using MVs, thereby influencing interspecies networks, microbial community organization and ecosystem dynamics. Employment of the specially surfaced structured strips of the present invention may be used to alter the population of an individual's microbiome in a manner that can later the progression of bacterial related diseases, including migraines, cluster headaches and Alzheimer's. With respect to treatment, several embodiments employ Graphene oxide nanosheets, and especially in the form of the strips as described herein, to deliver an effective antibacterial material against dental pathogens, including especially *Treponema denticola*.

As discussed herein, there is an association with periodontitis and migraines. Thus, one aspect of certain embodiments of the present invention relate to a series of steps to be undertaken to address the killing and elimination of certain gram negative bacteria that are associated with periodontitis, followed by the purposeful application of a composition having beneficial bacteria that are adapted to growth so as to populate a person's mouth and thus prevent the reestablishment of harmful bacteria that could, if permitted to persist in a person's mouth, lead to various maladies, including periodontitis, Alzheimer's disease, cluster headaches and migraines. In particular embodiments, strips are employed that have at least one encapsulated drug containing capsule that when broken or fractured, can release a predetermined amount of a drug, such as one effective to reduce if not eliminate certain gram negative bacteria and/or spirochetes that are believed responsible for periodontal disease, and in one preferred embodiment involves the use of metronidazole, preferably encapsulated or imbued onto a bioadhesive strip of the present invention. Certain embodiments of the present invention employ oral pharmaceutical compositions that include metronidazole, especially contained within a release layer of a bioadhesive strip that dissolves or erodes in the oral cavity.

Thus, in certain embodiments, the present invention provides an ability of a patient to purposefully cause the rupture of an encapsulated packet or pocket (e.g. a space in a strip that captures the agent of choice, which is released upon the rupture of such packet/pocket) that is associated with a strip that is adapted to be placed in association with a person's gums, with the encapsulated material preferably being an antibiotic, e.g. metronidazole, adapted to kill gram negative bacteria, and especially microbes associated as a causative agent in periodontitis.

Metronidazole is a nitroimidazole antibiotic with antibacterial activity against obligate anaerobic bacteria and certain protozoan parasites. The usual oral antibacterial therapies for treating pathologies have often given contradictory results. For instance, excessive dilution of the active ingredient has been observed in the intestinal lumen. This dilution is believed to be due to the premature release of the antibacterial agent from the pharmaceutical form even before reaching the duodenum such as in the stomach and in the immediate vicinity of the patient's pyloric valve. Similarly, in the oral cavity, use of metronidazole in a systemic fashion has limited results, as it does not persist in a concentrated enough form to kill undesired microbes that are entrenched in the gum regions of a person's mouth. Thus, in various embodiments of the present invention, metronidazole is provided in adhesive strips that are configured for providing the oral cavity with a sufficiently high level and dosage of the drug to accomplish the desired killing of certain bacterial species, including particular spirochetes such as *T. denticola*.

In another particular aspect, a genetically modified microbe, such as a bacteria of the species *T. denticola* and/or *Prevotella*, includes an inducible promoter directing expression of an essential protein and/or is modified such that expression of virulence factors are substantially reduced or eliminated. In certain embodiments, a composition comprises one or more genetically modified microbes, such as a bacteria of the species *T. denticola* and/or *Prevotella*, each of which are genetically modified, and especially by employment of CRISPR-Cas or Cpf1 systems to attenuate virulence factors, etc. CRISPR-Cas or Cpf1 modified microbes in which expression of an endogenous pathogenic protein is substantially reduced or eliminated in the one or more genetically modified bacteria include an inducible promoter regulating the expression of a virulence factor for such microbe.

Still other embodiments are directed to the use of bacteriophages modified to attack particular bacteria, especially *T. denticola* and/or *Prevotella*, to reduce the populations of one or the other in the oral cavity. In accordance with the present invention, native bacterial adaptive immune systems can be modified to thwart the conventional ability to confer immunity against bacteriophage infection. The CRISPR-Cas sequences, which are present in approximately 40% of eubacterial genomes and nearly all archaeal genomes sequenced to date, is employed to reverse the resistance to various antimicrobial agents such as small molecule antibiotics and bacteriophages.

Thus in certain embodiments, the innovative method is directed to decreasing the relative representation of a specific strain of bacteria, preferably *T. denticola* and/or *Prevotella*, within a heterogenous population of oral bacteria, comprising contacting the heterogenous population of oral bacteria with a bacteriophage comprising a polynucleotide that expresses (a) an RNA-directed DNA-binding polypeptide comprising a nuclease module; and (b) a targeting module comprising a guide RNA, wherein the targeting module tethers the RNA-directed DNA-binding polypeptide to a target DNA sequence within, thereby producing a double-strand break within the target sequence, wherein the target sequence is unique to the specific strain of *T. denticola* and/or *Prevotella* bacteria.

In certain embodiments of the present invention, delivery of beneficial bacteria, after the removal of pathogenic bacteria and also after use of the strip treatments as described herein (e.g. including the administration of local antibiotics to oral tissues), is achieved in a manner that comports with where such bacteria are normally located in a person's body. For example, many of the bacteria that confer protection against autoimmune diseases and that are otherwise believed to promote health in humans, and as described herein, are normally resident in the human mouth. For instance, one of the FLVR bacteria recently touted as being beneficial in the prevention of disease, namely *Veillonella*, is commonly found in a person's mouth, mostly living on the tongue and saliva. In various embodiments, selected bacteria, such as *Veillonella*, is purposefully presented on an oral strip that adheres to the mucosal membrane of a person.

In various embodiments of the present invention, bacterial species to be exposed to a person's oral (or in other embodiments, gut) microbiome, include those specifically modified by employing the CRISPR-Cas and CRISPR-Cpf1 systems to render the virulence factors of various bacteria ineffective. CRISPR (Clustered Regularly Interspaced Short Palindromic Repeats) is a prokaryotic adaptive defense system that provides resistance against alien replicons such as viruses and plasmids. CRISPRs evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. In certain preferred embodiments, rather than using CRISPR-Cas, one employs the CRISPR-associated endonuclease Cpf1. e.g. a CRISPR from *Prevotella* and *Francisella* 1 (Cpf1) nuclease for CRISPR-based genome editing, and incorporating 20150252358 to Maeder by this reference).

CRISPR-Cpf1 is a class II CRISPR effector that is distinct from Cas9, and is a single RNA-guided endonuclease that uses T-rich PAMs and generates staggered DNA double stranded breaks instead of blunt ends. Its smaller protein size and single RNA guide requirement makes CRISPR applications simpler and with more precise control. The human gut is a rich habitat populated by numerous microorganisms, each having a CRISPR system. To comply with written description and enablement requirements, incorporated herein by the following references are the following patent publications: 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 2015/0132263 to Liu; and 2014/0068797 to Doudna; 2014/0255351 to Berstad et al.; 2015/0086581 to Li; 2016/0311913 to Sun; PCT/US2014/036849 and WO 2013/026000 to Bryan; 2018/0127490 and 2018/0111984 to Bigal, et al.; 2018/0092899 to Liu, et al.; 2017/0240625 to Zeller, et al.; 2017/0342141 to Russo, et al.; 2018/0134772 to Sharma et al.; 2017/0201455 to Soares, et al.; 2017/0348303 to Bosse, et al.; 2017/0298115 to Loomis, et al.; and 2012/0294822 to Russo, et. al. 2018/0016647 and 2018/0016647 to Van Sinderen, et al.; 2018/0100169 to Soucaille, et al.; 2017/0232043 to Falb et al. and 2015/0045546 to Siksnys et al.

In various aspects of the present invention, CRISPR is employed to modify aspects for both bacterial and helminthes gene expression such that undesired normally transcribed proteins are excised or precluded from being expressed, thus precluding the deleterious effects of such proteins. Thus, normally dangerous species of bacteria and helminthes (from a perspective of such bacteria or helminthes causing disease in a human) can be modified so that such undesired effects of bacterial and helminthes infection are disrupted or deleted or lessened in a fashion that still permits the beneficial aspects of bacterial and helminthes proteins to be maintained.

Various embodiments of the present invention combine each of the above referenced four FLVR bacteria and using CRIPR, pathogenic and/or toxic elements are excised to preclude detrimental health issues that would normally be encountered using one or more of such bacteria, while preserving the immune system attributes attained by the presence of such bacteria. Preferably, the CRISPR modified bacteria of the FLVR species are then combined in a formulation suitable for use as either an oral composition (preferably administered via the strips as described herein). In certain embodiments, treatment of newborns so as to promote beneficial gut and oral microbiomes is achieved via strips or a vaginal cream (for the mother) such that a newborn is first exposed to such bacteria when traveling down the birth canal.

In certain embodiments of the present invention, antibiotic resistance of certain bacteria is modulated by employment of CRISPR to insert into the genome of a bacteria antibacterial sensitivity such that it can selectively be killed, if necessary, after it is employed to trigger desired immune responses in a new born or other individual. Thus, the various bacterial and helminthes species mentioned herein that are included in an or added to an Amish-soil may, in certain embodiments, be extracted and modified using CRISPR methods to do one of several things, including adding antibiotic sensitivity to various species so that they can be employed for triggering immune responses of an individual, and then later killed or rendered ineffective by the use of targeted antibiotics or anti-helminthes drugs.

In particular embodiments, directed to a topical composition of a bacterial and/or helminthes containing composition, such composition includes cells that have been transformed by use of CRISPR to delete particular undesired attributes of wild-type species, including the expression of disease causing proteins. Thus, creams, ointments, etc. may be employed as a vaginal pre-birth composition so that a new born, traveling down the vaginal canal, is exposed to a plurality of beneficial bacteria and/or helminthes proteins and other constituents such that a new born innate immune response is triggered to protect the new born from developing the variety of allergic and autoimmune diseases as described herein. In still other embodiments, a suitable oral or mucosal agent is administered to an individual's microbiome to provide a way to alter the existing microbiome of the individual such that migraines and cluster headaches can be prevented.

The use of CRISPR to tailor bacterial and helminthes components to either add desired characteristics and/or to delete known deleterious aspects of such bacteria or helminthes, provides a novel system and method for treating a variety of diseases such that bacteria and helminthes that would normally be considered too dangerous to employ as an agent to treat allergic, autoimmune conditions, migraines, cluster headaches, etc. is now rendered available for such purposes.

In various embodiments, DNA is injected into bacteria to restore antibiotic sensitivity to drug-resistant bacteria, and to also prevent the transfer of genes that create that resistance among bacteria. The CRISPR-CAS system may also be employed to render certain bacteria sensitized to certain antibiotics such that specific chemical agents can selectively choose those bacteria more susceptible to antibiotics, see, e.g. U.S. Pat. Publication No. 2013/0315869 to Qimron, which is incorporated in its entirety by this reference.

The microbiome of an individual is disrupted by antibiotics and thus, the employment of CRISPR as a way to bypass common modes of multidrug resistance, while being selective for individual strains, is employed in various embodiments of the present invention to attain the benefits derived by the presence of particular bacteria and helminthes, including the triggering of desired immune development by newborns and other individuals, (e.g. those with multiple sclerosis, etc.) as well as in addressing the treatment and avoidance of migraines and cluster headaches. CRISPR-Cas systems employ CRISPR RNAs to recognize and destroy complementary nucleic acids. In various embodiments of the present invention, CRISPR-Cas systems are used as programmable antimicrobials to selectively kill bacterial species and strains such that desired selected targets can be focused on such that virtually any genomic location may be a distinct target for CRISPR-based antimicrobials, and that, in conjunction with an appropriate delivery vehicle, such as those employed by Bikard et al. and Citorik et al., one is able to effectively deploy a CRISPR-Cas system as an antimicrobial agent.

Another aspect of certain embodiments includes making synthetic CRISPR-containing RNAs that target genes of interest and using them with Cas enzymes. The specificity of CRISPR-Cas systems permits one to design methods to target a single bacterial species so that only essential genes from that one species is targeted and cut up. CRISPR-Cas systems are employed in various ways in the many embodiments of the present invention to retain the beneficial bacterial communities intact and to offer protection against undesired bacterial pathogens.

CRISPR has a certain protein in it called Cas9 that acts like a scissor as it recognizes specific sequences of DNA and cuts it enabling one to perform genome-editing of a bacterial genome in a person's microbiome. There exists another CRISPR system, CRISPR-Cpf1 that is even more preferred for use in microbial systems. Cpf1 is important in bacterial immunity and is well adapted to slice target DNAs. Cpf1 prefers a "TTN" PAM motif that is located 5' to its protospacer target—not 3', as per Cas9, making it distinct in having a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 merely requires a cRNA that is about 43 bases long—of which 24 nt is protospacer and 19 nt is the constitutive direct repeat sequence. In contrast, the single RNA that Cas9 needs is ~100 nt long.

The CRISPR system may be employed in various embodiments to strengthen antibiotics or to kill the bacteria altogether. By removing the bacteria's genes that make them antibiotic-resistant, CRISPR can boost the effectiveness of existing drugs. CRISPR can also be used to remove a bacteria's genes that make them deadly and facilitate RNA-guided site-specific DNA cleavage. Analogous to the search function in modem word processors, Cas9 can be guided to specific locations within complex genomes by a short RNA search string.

In certain embodiments, various particular bacterial species are focused on to delete or modulate their gene expressions, such species including the following: *Streptococcus; Escherichia coli, Streptococcus pyogenes*, and *Staphylococcus epidermidis*. This prokaryotic viral defense system has become one of the most powerful and versatile platforms for engineering biology.

In various embodiments, the CRISPR-Cas systems is employed to control the composition of the gut flora or oral microbiome, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas systems. Because of the sequence specificity of targeting, CRISPR-Cas systems may be used to distinguish strains separated by only a few base pairs. The specificity of targeting with CRISPR RNAs may be employed to readily distinguish between highly similar strains in pure or mixed cultures. Thus, in certain embodiments, varying the collection of delivered CRISPR RNAs is employed to quantitatively control the relative number of individual strains within a mixed culture in a manner to circumvent multidrug resistance and to differentiate between pathogenic and beneficial microorganisms.

In certain other aspects, particular embodiments of the present invention are directed to the use of CRISPR to excise certain prior infectious adenovirus DNA sequences that are considered responsible for the increased obesity of individuals harboring the same. Reference is made to Kovarik, U.S. Pat. No. 8,585,588, "Method and system for preventing virus-related obesity and obesity related diseases." After determining whether one has been infected with a particular virus, the viral DNA can then be excised via CRISPR-Cas to remove the previously inserted DNA, thus effectively reducing if not eliminating the adenovirus gene from the individual. Thereafter, to avoid being infected with such adenovirus again, practice of the method as set forth in U.S. Pat. No. 8,585,588 will lessen, if not prevent, reacquisition of such virus.

Controlling the composition of microbial populations is important in the context of desiring to expose individuals to particular species of bacterial and other microbes, helminthes, etc. and especially those that have not been previously exposed to antibiotics, antimicrobial peptides, and lytic bacteriophages. Use of CRISPR-Cas provides a generalized and programmable strategy that can distinguish between closely related microorganisms and allows for fine control over the composition of a microbial population for use in the present invention. Thus, the RNA directed immune systems in bacteria and archaea called CRISPR-Cas systems is employed in various embodiments of the present invention to selectively and quantitatively remove and/or alter individual bacterial strains based on sequence information to enable the fine tuning of exposure of desired antigens. Thus, such genome targeting using CRISPR-Cas systems allows one to specifically remove and/or alter individual microbial species and strains in desired ways.

In various embodiments, it is desirable to remove—using CRISPR-Cas systems—particular viable genes in pathogenic bacteria and/or other pathogenic portions (e.g. plasmids, etc. of such bacteria) —while sparing other desired commensal bacteria, in order to provide exposure to desired immune developing proteins.

In various embodiments, one of skill in the art will appreciate that removal or alteration of particular strains of bacteria may be achieved using both type I and type II CRISPR-Cas systems, given the distinction between these systems being that type I systems cleave and degrade DNA through the action of a 3'-to-5' exonuclease, whereas type II systems only cleave DNA. In still other embodiments, multiple guide RNAs can also be used to target several genes at once. The use of effector fusions may also expand the variety of genome engineering modalities achievable using Cas9. For example, a variety of proteins or RNAs may be tethered to Cas9 or sgRNA to alter transcription states of specific genomic loci, monitor chromatin states, or even rearrange the three-dimensional organization of the genome.

Because preferred embodiments relate to the modification of microbes—rather than to the human genome—and especially only those microbes that show tropism for humans, the unintended consequences of employing Crispr-Cas on organisms is lessened, if not eliminated. Moreover, use of CRISPR-Cas to also insert genes that have controllable elements such that the cells are killed by triggering the expression of such genes, is another way to reduce if not eliminate concerns about an unintended release of a modified organism. These types of controls are well known to those of skill in the art and have been long employed, for example, by those involved in creating genetically engineered organisms, such as by inserting genes so that organisms become susceptible to various conditions, such as temperature, antibiotic exposure, etc., such that microbes that may somehow escape desired conditions will not be viable. Particular embodiments of the present invention are directed to the employment of four specific bacterial genera—*Lachnospira, Veillonella, Faecalibacterium* and *Rothia*. Modifying the human genome, made possible by the CRIPSR technique, has its own wonderful upsides and equally daunting downsides. Permanent deletion of genes from the human genome is much more controversial than deletion of bacterial genes. Thus, one desirable aspect of the present invention is directed to the far less controversial modification of gut microbes resident in the human being to promote health and to trigger the desired immune responses as described herein.

*Faecalibacterium prausnitzii*, which represent more than 5% of the bacteria in the intestine, is encouraged to populate the guts of patients. Such enhanced growth of this bacterium may also be employed to combat certain forms of inflammatory bowel disease. In various embodiments of the present invention, *Enterococcus faecalis* is are subjected to CRISPR-Cas procedures to remove undesired virulence and pathogenicity factors, such as several genes isolated from resistant enterococci (agg, gelE, ace, cy1LLS, esp, cpd, fsrB) which encode virulence factors such as the production of gelatinase and hemolysin, adherence to caco-2 and hep-2 cells, and capacity for biofilm formation. Deletion and removal of certain antibiotic resistance, for example the acquisition of vancomycin resistance by enterococci, is desired also so as to properly and safely employ this bacteria in the present invention. In a particular embodiment, the addition of *E. faecalis* LAB3 1 is employed to trigger desired immune system responses.

CRISPR-Cas can be used on the various identified microbiome constituents to modify gene expression, including cutting of a gene, repress or activate a gene, etc. It can be employed to deliver desired regulators or any protein to a desired place on a genome of a microbe, thus permitting one to tailor the attributes of the microbiome of an individual to promote the health thereof, including the programmed triggering of particular immune responses in an infant. Because CRISPR-Cas acts before transcription occurs, it is able to be employed to target regulatory and other elements on the DNA of microbes that make up the microbiome. In certain embodiments, CRISPR-Cas is employed to deliver fluorescent markers to certain DNA sequences, thus permitting one to determine whether any particular sample has been treated in accordance with the present invention, thus ensuring, for example, identity of various materials, safety issues, types of enhanced soils, etc. This permits labeling of living cells with a desired color.

Many embodiments rely upon the ability to deliver agents via mucosal adhesive strips, such as described, for example, in U.S. Pat. No. 8,701,671, which is fully incorporated herein by this reference. In such a manner, one objective is to accept the beneficial traits of the microbiome's interaction with the human immune system while avoiding the infectious aspects of bacterial, viral and helminth aspects of such exposure to a human being. Thus, in various embodiments of the present invention, the engineering of communal bacteria with improved properties using a CRISPR/Cas system is employed.

Thus, in certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene.

There exist various concerns about how CRISPR-Cas systems and method will be employed with respect to attempting to improve human health through and using a technology that cuts sections of DNA out of a genome, effecting permanent changes to the human DNA. Indeed, many in the scientific community are considering whether a moratorium on the use of this powerful and yet simple technology should be implemented until such time as all the risks involved can be better assessed. In the context of the present invention, however, this particular issue is either absent or of lesser importance due to one focus of many embodiments being relegated to the modification of DNA of the microbe genomes, rather than the human genome. Thus, the present invention is one way in which the human health concerns can be benefited directly by the use of a DNA deletion system without affecting the long term and permanent deletion of human genes. It is not believed to be obvious, let alone intuitive, that human health can be benefited by such a DNA deletion system used in a fashion that affects only gut microbes in a human's system. Moreover, the use of such a DNA modification system for microbes, but not for the direct deletion of genes from a human, and the use of such a system prior to the exposure of a human to such modified microbes, has not previously been done, especially with the added step of modifying select microbes having immune beneficial attributes—and especially using modified microbes that one would otherwise have considered to be pathogenic.

Individuals who have regular contact with livestock, such as farmers and their wives, have bacterial communities dominated by *Prevotella*, a type of bacteria that is also abundant in the gut microbiota of cattle and sheep. *Prevotella* are among the most numerous microbes culturable from the rumen and hind gut of cattle and sheep. Percentages vary but *Prevotella* is often the most common bacterial genus in the cattle. While certain aspects of particular embodiments are directed to the *Prevotella* genus, others are more focused on particular species within such genus, namely *P. intermedia*. The present inventors contend that the contributions of microbes to multiple aspects of human physiology and neurobiology in health and disease have up until now not been fully appreciated.

*Treponema denticola* is an oral anaerobic spirochete closely associated with the pathogenesis of periodontal disease—and the present inventors believe it is associated with numerous systemic diseases, including Alzheimer's disease. The *T. denticola* major surface protein (MSP), involved in adhesion and cytotoxicity, and the dentilisin serine protease are key virulence factors of this organism. Thus, one aspect of the present invention relates to the use of CRISPR-Cas or Cpf1 to target these virulence factors and thus, excise them from *T. denticola* so as to render it susceptible to antibiotics so as to reduce its presence in the oral microbiome, thus advancing the prevention of not only migraines, cluster headeaches and dizziness, but for Alzheimer's disease as well. Periodontal diseases are polybacterially induced, multifactorial inflammatory processes of the tooth attachment apparatus and are the primary cause of tooth loss after the age of 35. The ability of such disease to escape detection and the failure of many to regularly visit a dentist to diagnose such a disease, leads to the prevalence of Alzheimer's disease as we see today. The elderly often show neglect of oral hygiene which can stimulate recurrent chronic oral infection, which promotes inflammation and then leads to confusion and dementia. Interfering with inflammation is thus one objective of the present invention and in certain embodiments, it is beneficial to combine anti-inflammatory agents with antibacterials.

The periodontopathogenic spirochete *T. denticola* possesses a number of virulence factors including motility, the ability to attach to host tissues, coaggregation with other oral bacteria, complement evasion mechanisms, and the presence of several outer sheath and periplasmic proteolytic and peptidolytic activities. Two components associated with the spirochetes' outer sheaths and extracellular vesicles are the major surface protein (also known as the major outer sheath protein [MSP]) and a serine protease, dentilisin, previously known as the chymotrypsin-like protease. Recent bioinformatics analysis reclassified dentilisin as a member of the subtilisin rather than the chymotrypsin family. Dentilisin is involved in the degradation of membrane basement proteins (laminin, fibronectin, and collagen IV), serum proteins (fibrinogen, transferrin, IgG, and IgA), including protease inhibitors ($\alpha$1-antitrypsin, antichymotrypsin, antithrombin, and antiplasmin), and bioactive peptides. Degradation of tight junction proteins by dentilisin seems to enable the penetration of epithelial cell layers by this oral spirochete. MSP is a major antigen with pore-forming activity. This abundant membrane protein mediates the binding of *T. denticola* to fibronectin, fibrinogen, laminin, and collagen, induces macrophage tolerance to further activation with lipopolysaccharide (LPS), and elicits cytotoxic effects in different cell types.

One object of the present invention is to employ LL-37 against *T. denticola*, especially employing the strips as set forth herein. Saliva inhibits dentilisin, attenuating its virulence properties but conserving LL-37 activity. Thus one aspect of the present invention is directed to the use of LL-37 to kill *T. denticola*. The human host defense peptide LL-37 is preferably administered via the strips of the present invention, especially those having encapsulated pockets of the agent such that administration thereof can be achieved by the patient upon tongue pressure being applied to a frangible shell present as part of the strip. Deficiency in the human host defense peptide LL-37 has previously been correlated with severe periodontal disease. *Treponema denticola* is an oral anaerobic spirochete closely associated with the pathogenesis of periodontal disease. *Treponema denticola* is an important periodontal pathogen capable of tissue invasion. Its chymotrypsin-like proteinase (CTLP) can degrade a number of basement membrane components in vitro, thus suggesting a contribution to tissue invasion by the spirochete. Periopathogen survival is dependent upon evasion of complement-mediated destruction. *Treponema denticola*, an important contributor to periodontitis, evades killing by the alternative complement cascade by binding factor H (FH) to its surface.

In the healthy subgingival crevice, *Treponema denticola* account for ~1% of the total bacteria. With the progression of periodontitis, the abundance of oral treponemes increases dramatically and can reach 40% of the total bacterial population. Disease severity correlates specifically with the outgrowth of *Treponema denticola* and other bacterial species of the red microbial complex.

*Treponema* denticolais is an oral spirochete and periopathogen that transitions from low abundance in healthy subgingival crevices to high abundance in periodontal pockets. The *T. denticola* response regulator AtcR harbors the relatively rare, LytTR DNA binding domain. LytTR domain containing response regulators control critical transcriptional responses required for environmental adaptation. The functional diversity of the proteins encoded by the putative AtcR regulon suggests that AtcR sits at the top of a regulatory cascade that plays a central role in facilitating *T. denticola*'s ability to adapt to changing environmental conditions and thrive in periodontal pockets.

While most bacteria, including spirochetes, employ two component regulatory (TCR) systems and cyclic nucleotides to regulate adaptive responses, certain embodiments of the present invention are directed to the *T. denticola* genetic regulatory system and signaling mechanisms to decrease the growth and maintenance thereof in the oral cavity.

One general take-away from the present invention relates to how best to adopt practices that establish and retain and maintain oral health such that individuals do not suffer from the array of different maladies that are now understood to be related, whether directly or indirectly, to oral health. For example, it is common for individuals to get their teeth cleaned a few times a year. Upon such a cleaning procedure, however, the dental surfaces are relatively "clean" of the biofilms that where established thereon since the last dental cleaning visit. Instead of proactively applying a beneficial composition of beneficial bacteria to the cleaned surfaces, however, it is common and typical practice to simply have the dental patient leave the dental office, after scheduling another 6 month visit, and thus leave the colonization of the dental surfaces up to the chance presence of bacteria that may then be present in the person's mouth or surrounding environments. Given the growing and recent knowledge of the nature of oral biofilms, populated by a myriad of bacteria of different but coexisting species of bacteria, it is one aspect of the present invention to purposefully contact a person's recently cleaned teeth with a composition that contains bacteria believed to be especially beneficial to the establishment of a "healthy" biofilm. This entails, in certain embodiments, a progressive and successive contact of a person's teeth with different bacteria, with the staging of contact with various bacteria based upon the known synergistic relationship between oral bacteria, and with the emphasis being to limit the most pathogenic bacteria known to cause some of the prevalent problems suffered by humans. Certain embodiments directed to oral care by altering the composition of oral biofilms so that the proportion of microorganisms, which are detrimental to oral health, are reduced while the proportion of health-promoting microorganisms are increased. There are several organisms that can actively protect the oral cavity against pathogenic species by reduction or prevention of bacterial adhesion to the surface of the teeth or oral surfaces, such bacteria including the genera *Neisseria, Rothia, Corynebacterium* and *Streptococcus*. Biofilms consist of microorganisms growing in close association embedded in an extracellular polymeric matrix, which allows them to cooperate in various ways and provides some protection against outside influences. The concentration of antimicrobial agents required to reach bactericidal activity against a biofilm is often much higher than would be required for planktonic bacteria. In certain embodiments, the number of bacteria such as *Prevotella, Veillonella, Porphyromonas, Atopobiurn, Selenomonas* and *Fusobacterium* are reduced, while the number of bacteria such as *Neisseria, Rothia, Corynebacterium* and *Streptococcus* are increased.

The limitation of the growth and establishment of a certain spirochete, namely, *Treponema denticola*, is a focus of various embodiments. The use of CRISPR-Cas and similar technologies to alter the genetic makeup of such spirochete so as to lessen its infectivity in various regards is yet another way to accomplish this objective. Excision or retardation of the various virulence factors for this bacteria are other ways in which such a goal can be achieved. Still other ways to accomplish this objective involves interfering with the admittedly complex interactions and associations of other bacteria responsible for the growth of spirochetes in the oral cavity. Thus, by directly addressing still other supporting bacteria, one is able to indirectly, but nonetheless effectively, limit the progression of spirochetes, and in particular, *Treponema denticola*, establishment and growth. By doing so, one is saved from the ravages of Alzheimer's disease, as well as the several other diseases that are noted as being related to the oral health of a person. Providing a tooth contacting substance at the time of a dental cleaning is preferred, as well as possible re-applications of compositions by the individual so as to establish a preferred buildup of a beneficial biofilm having particular bacteria constituents. Such formulations for beneficial oral cavity health may vary dependent upon many factors, such as the particular diet of the individual, the race of the individual, the age, etc. It is known that bacterial populations vary greatly between individuals, as well as within the same individual based on health and age. Thus, selection of particular compositions having a pre-determined composition of bacteria formats and variety are contemplated by the present invention.

Bacterial species are able to use various energy sources, including light and diverse organic and inorganic chemicals, for growth and metabolism. These energy sources are used to produce an electrochemical gradient that provides an electron donor for metabolism and allows maintenance of a membrane potential and proton motive force. The energetics of living systems are driven by electron transfer processes in which electrons are transferred from a substrate, which is thereby oxidized, to a final electron acceptor, which is thereby reduced. In certain embodiments, it is possible to control metabolism by linking biochemical processes to an external electrochemical system, with such linking of biochemical and electrochemical systems permitting the use of electricity as a source of electrons for biotransformation reactions. A reversible biochemical-electrochemical link allows for conversion of microbial metabolic and/or enzyme catalytic energy into electricity.

In certain other embodiments, sugar is used as a source of energy, notably glucose that is converted into different sugars via an enzymatic cascade to provide necessary energy to create an electrochemical gradient. This, in turn, is used to power an enzyme that synthesizes adenosine triphosphate (ATP). In contrast to natural catabolic pathways for cellular glucose oxidation, a preferred embodiment does not rely on ATP as an energy carrier. Instead, two redox enzymes oxidize glucose, generating reduced nicotinamide adenine dinucleotide (NADH) as the sugar is broken down. Another series of enzymes (as many as ten additional enzymes) further breakdown the sugars and feed them back to the redox enzymes to produce more NADH, with water and carbon dioxide being the only by-products. NADH is a reducing agent and acts as an electron shuttle that carries electrons in living cells from one molecule to another. NADH first transfers the electrons stripped from the glucose to a mediator with the help of an enzyme. The mediator then delivers these electrons to the battery's electrode, rendering it available to power an electronic device. Such a battery mimics the way a living cell transfers electrons from one molecule to another to generate power, it runs on renewable sugars, and has a high-energy storage density, rechargeable providing an additional sugar solution. Malodextrin—a polymer made up of glucose subunits—may be employed together with particular different enzymes able to strip electrons from a single glucose molecule, thus harnessing the generated energy to power an electrical device.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method for increasing beneficial bacteria and decreasing pathogenic bacteria in the oral cavity of a subject, comprising, facilitating the growth of desired bacteria in a human's mouth by using a bioadhesive strip, said strip having a first and second side, said first side having at least one encapsulated feature containing at least one beneficial bacteria, and the second side having a bioadhesive that is adapted to bind to a mucosal membrane for at least 1 hour while inside a person's mouth, said strip comprising bioluminescent material to facilitate a user's ability to view when viewing in a mirror the placement of the strip in one's mouth, wherein said strip has compounds residing thereon to facilitate the growth of desired bacteria beneficial to a person's health, and wherein said at least one bacteria has one of a pathogenic or toxic element excised using a clustered regularly interspaced short palindromic repeats (CRISPR)-CRISPR associated protein (Cas) system or a CRISPR from *Prevotella* and *Francisella* 1 (Cpf1) system.

2. The method as set forth in claim 1, wherein said strip is dissolvable in a person's mouth.

3. The method as set forth in claim 1, wherein the bioluminescent material comprises one of luciferin, luciferase and aequorin.

4. The method as set forth in claim 1, wherein said strip includes xylitol.

5. The method of claim 1, wherein said strip further comprises breath freshening components.

6. The method of claim 1, wherein light emanating from the bioluminescent material decreases the growth of pathogenic bacteria populations and reduces biofilm formation.

7. The method of claim 1, wherein light emanating from the bioluminescent material induces nitric oxide release from cellular sources.

8. The method of claim 1, wherein the bioluminescent material provides light having a wavelength of 400-410 nm that reduces *Porphyromonas gingivalis* growth inside the subject's oral cavity.

9. A method to facilitate the growth of desired bacteria on a human's mucosal membrane by using a bioadhesive strip, comprising:

providing to an individual in need thereof a bioadhesive strip, said strip having a first and second side, said first side having at least one encapsulated feature containing at least one bacteria that has one of a pathogenic or toxic element excised using a clustered regularly interspaced short palindromic repeats (CRISPR)-CRISPR associated protein (Cas) system or a CRISPR from *Prevotella* and *Francisella* 1 (Cpf1) system and the second side having a bioadhesive that is adapted to bind to a mucosal membrane for at least 1 hour.

10. The method as set forth in claim 9, wherein the mucosal membrane is in a person's mouth.

11. The method as set forth in claim 9, wherein said strip is dissolvable in a person's mouth.

12. The method as set forth in claim 9, wherein the strip comprises one of luciferin, luciferase and aequorin.

13. The method as set forth in claim 9, wherein said strip includes xylitol.

14. The method of claim 9, wherein said strip further comprises breath freshening components.

15. The method of claim 9, wherein the strip reduces *Porphyromonas gingivalis* growth inside the subject's oral cavity.

* * * * *